United States Patent
Gellert et al.

(10) Patent No.: US 12,297,289 B2
(45) Date of Patent: May 13, 2025

(54) ANTI-MUC1 ANTIBODY

(71) Applicant: GLYCOTOPE GMBH, Berlin (DE)

(72) Inventors: Johanna Gellert, Berlin (DE); Anke Flechner, Berlin (DE); Doreen Weigelt, Berlin (DE); Antje Danielczyk, Berlin (DE)

(73) Assignee: GLYCOTOPE GMBH, Berlin (DE)

( * ) Notice: Subject to any disclaimer, the term of this patent is extended or adjusted under 35 U.S.C. 154(b) by 1024 days.

(21) Appl. No.: 17/055,303

(22) PCT Filed: May 17, 2019

(86) PCT No.: PCT/EP2019/062756
§ 371 (c)(1),
(2) Date: Nov. 13, 2020

(87) PCT Pub. No.: WO2019/219889
PCT Pub. Date: Nov. 21, 2019

(65) Prior Publication Data
US 2021/0221910 A1    Jul. 22, 2021

(30) Foreign Application Priority Data

May 18, 2018 (EP) ..................... 18173253

(51) Int. Cl.

| | |
|---|---|
| C07K 16/30 | (2006.01) |
| A61K 31/4745 | (2006.01) |
| A61K 39/00 | (2006.01) |
| A61K 39/395 | (2006.01) |
| A61K 47/54 | (2017.01) |
| A61K 47/65 | (2017.01) |
| A61K 47/68 | (2017.01) |
| A61P 35/00 | (2006.01) |
| A61P 35/02 | (2006.01) |

(52) U.S. Cl.
CPC ...... *C07K 16/3092* (2013.01); *A61K 31/4745* (2013.01); *A61K 39/39558* (2013.01); *A61K 47/545* (2017.08); *A61K 47/65* (2017.08); *A61K 47/68037* (2023.08); *A61K 47/6851* (2017.08); *A61P 35/00* (2018.01); *A61P 35/02* (2018.01); *A61K 2039/505* (2013.01); *C07K 2317/14* (2013.01); *C07K 2317/24* (2013.01); *C07K 2317/41* (2013.01); *C07K 2317/55* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,931,275 A | 6/1990 | Shinitzky et al. |
| 4,943,533 A | 7/1990 | Mendelsohn et al. |
| 5,480,968 A | 1/1996 | Kraus et al. |
| 5,506,343 A | 4/1996 | Kufe |
| 5,547,933 A | 8/1996 | Lin |
| 5,596,088 A | 1/1997 | Boucher et al. |
| 5,677,171 A | 10/1997 | Hudziak et al. |
| 5,683,674 A | 11/1997 | Taylor-Papadimitriou et al. |
| 5,739,277 A | 4/1998 | Presta et al. |
| 5,795,779 A | 8/1998 | Mccormick et al. |
| 5,804,187 A | 9/1998 | Do Couto et al. |
| 5,821,337 A | 10/1998 | Carter et al. |
| 5,834,476 A | 11/1998 | Terasawa et al. |
| 5,837,673 A | 11/1998 | Tsujihara et al. |
| 5,888,773 A | 3/1999 | Jost et al. |
| 5,892,043 A | 4/1999 | Tsujihara et al. |
| 5,948,646 A | 9/1999 | Srivastava |
| 5,961,979 A | 10/1999 | Srivastava |
| 5,968,511 A | 10/1999 | Akita et al. |
| 6,168,793 B1 | 1/2001 | Srivastava |
| 6,172,213 B1 | 1/2001 | Lowman et al. |
| 6,214,345 B1 | 4/2001 | Firestone et al. |
| 6,291,671 B1 | 9/2001 | Inoue et al. |
| 6,315,997 B1 | 11/2001 | Do Couto et al. |
| 6,465,220 B1 | 10/2002 | Hassan et al. |
| 6,602,684 B1 | 8/2003 | Umana et al. |
| 6,811,996 B1 | 11/2004 | Inoue et al. |
| 6,835,807 B1 | 12/2004 | Susaki et al. |
| 6,964,292 B2 | 11/2005 | Meyer et al. |
| 6,984,384 B1 | 1/2006 | Subjeck et al. |
| 7,041,818 B2 | 5/2006 | Susaki et al. |
| 7,268,120 B1 | 9/2007 | Horton et al. |
| 7,449,184 B2 | 11/2008 | Allison et al. |
| 7,585,491 B2 | 9/2009 | Govindan |

(Continued)

FOREIGN PATENT DOCUMENTS

| | | |
|---|---|---|
| CA | 2927832 A1 | 11/2011 |
| CA | 2815154 A1 | 2/2012 |

(Continued)

OTHER PUBLICATIONS

Japanese Office Action issued in connection with JP Appl. Ser. No. 2020-564656 dated May 9, 2023.

(Continued)

*Primary Examiner* — Daniel C Gamett
(74) *Attorney, Agent, or Firm* — Foley & Lardner LLP

(57) ABSTRACT

The present disclosure pertains to novel antibodies directed against the cancer antigen MUC1. In particular, an antibody with improved antigen binding was obtained by deleting a glycosylation site in the CDR-H2 of a known anti-MUC1 antibody.

37 Claims, 11 Drawing Sheets

Specification includes a Sequence Listing.

(56) References Cited

U.S. PATENT DOCUMENTS

| | | |
|---|---|---|
| 7,595,192 B2 | 9/2009 | Goletz et al. |
| 7,833,979 B2 | 11/2010 | Sullivan et al. |
| 7,837,980 B2 | 11/2010 | Alley et al. |
| 7,999,083 B2 | 8/2011 | Govindan et al. |
| 8,017,388 B2 | 9/2011 | Goletz et al. |
| 8,088,357 B2 | 1/2012 | Goletz et al. |
| 8,226,945 B2 | 7/2012 | Ebens et al. |
| 8,268,319 B2 | 9/2012 | Govindan |
| 8,283,161 B2 | 10/2012 | Goletz et al. |
| 8,394,607 B2 | 3/2013 | Ebens et al. |
| 8,425,912 B2 | 4/2013 | Govindan |
| 8,524,865 B2 | 9/2013 | Ebens et al. |
| 8,592,165 B2 | 11/2013 | Goletz et al. |
| 8,609,370 B2 | 12/2013 | Goletz et al. |
| 8,617,846 B2 | 12/2013 | Goletz et al. |
| 8,741,291 B2 | 6/2014 | Bhat et al. |
| 8,741,365 B2 | 6/2014 | Goletz et al. |
| 8,779,102 B2 | 7/2014 | Goletz et al. |
| 8,802,820 B2 | 8/2014 | Chamberlain et al. |
| 8,907,071 B2 | 12/2014 | Sullivan et al. |
| 8,968,741 B2 | 3/2015 | Ebens et al. |
| 9,051,356 B2 | 6/2015 | Goletz et al. |
| 9,051,365 B2 | 6/2015 | Johnson et al. |
| 9,051,370 B2 | 6/2015 | Goletz et al. |
| 9,217,038 B2 | 12/2015 | Goletz et al. |
| 9,345,794 B2 | 5/2016 | Goletz et al. |
| 9,359,439 B2 | 6/2016 | Goletz et al. |
| 9,494,587 B2 | 11/2016 | Goletz et al. |
| 9,505,848 B2 | 11/2016 | Davis et al. |
| 9,732,160 B2 | 8/2017 | Rohlff et al. |
| 9,808,537 B2 | 11/2017 | Masuda et al. |
| 9,845,361 B2 | 12/2017 | Goletz et al. |
| 9,850,312 B2 | 12/2017 | Agatsuma et al. |
| 9,872,924 B2 | 1/2018 | Naito et al. |
| 10,195,288 B2 | 2/2019 | Masuda et al. |
| 10,227,417 B2 | 3/2019 | Agatsuma et al. |
| 10,280,230 B2 | 5/2019 | Goletz et al. |
| 10,383,878 B2 | 8/2019 | Hettmann et al. |
| 10,524,738 B2 | 1/2020 | Olsen |
| 11,872,289 B2 | 1/2024 | Gellert et al. |
| 2002/0132771 A1 | 9/2002 | Madiyalakan |
| 2003/0115614 A1 | 6/2003 | Kanda et al. |
| 2003/0148931 A1 | 8/2003 | Takahashi et al. |
| 2003/0166513 A1 | 9/2003 | Imura et al. |
| 2004/0029127 A1 | 2/2004 | Postaire et al. |
| 2004/0185053 A1 | 9/2004 | Govindan |
| 2004/0265998 A1 | 12/2004 | Goletz et al. |
| 2005/0123536 A1 | 6/2005 | Law et al. |
| 2005/0187378 A1 | 8/2005 | Kim |
| 2005/0203010 A1 | 9/2005 | Kim |
| 2005/0228007 A1 | 10/2005 | Jagtap et al. |
| 2005/0271671 A1 | 12/2005 | Griffiths |
| 2005/0276812 A1 | 12/2005 | Ebens, Jr. et al. |
| 2006/0018899 A1 | 1/2006 | Kao et al. |
| 2006/0029129 A1 | 2/2006 | Hannuksela |
| 2006/0051353 A1 | 3/2006 | Colombel et al. |
| 2006/0127419 A1 | 6/2006 | Goletz et al. |
| 2006/0193865 A1 | 8/2006 | Govindan |
| 2006/0251668 A1 | 11/2006 | Goletz et al. |
| 2006/0292129 A1 | 12/2006 | Goletz et al. |
| 2006/0292643 A1 | 12/2006 | Goletz et al. |
| 2007/0015239 A1 | 1/2007 | Bihoreau et al. |
| 2007/0071764 A1 | 3/2007 | Sullivan et al. |
| 2007/0116704 A1 | 5/2007 | Goletz et al. |
| 2008/0050310 A1 | 2/2008 | Ebens et al. |
| 2008/0131363 A1 | 6/2008 | Govindan et al. |
| 2008/0161245 A1 | 7/2008 | Kratz et al. |
| 2008/0226619 A1 | 9/2008 | Rubinstein et al. |
| 2008/0226681 A1 | 9/2008 | Goletz et al. |
| 2008/0226682 A1 | 9/2008 | Brake et al. |
| 2008/0305044 A1 | 12/2008 | Mcdonagh et al. |
| 2009/0046556 A1 | 2/2009 | Vlutters |
| 2009/0110632 A1* | 4/2009 | Young .............. A61P 25/00 424/94.1 |
| 2009/0181016 A1 | 7/2009 | Lenz |
| 2009/0274713 A1 | 11/2009 | Chari et al. |
| 2009/0286258 A1 | 11/2009 | Kaur et al. |
| 2009/0291093 A1 | 11/2009 | Govindan |
| 2010/0028947 A1 | 2/2010 | Goletz et al. |
| 2010/0068181 A1 | 3/2010 | Paliwal et al. |
| 2010/0120816 A1 | 5/2010 | Fontana et al. |
| 2010/0158952 A1 | 6/2010 | Goletz |
| 2010/0303837 A1 | 12/2010 | Goletz et al. |
| 2011/0045587 A1 | 2/2011 | Sullivan et al. |
| 2011/0059076 A1 | 3/2011 | Mcdonagh et al. |
| 2011/0070248 A1 | 3/2011 | Ichikawa et al. |
| 2011/0129570 A1 | 6/2011 | Goletz |
| 2011/0229406 A1 | 9/2011 | Hettmann et al. |
| 2011/0293513 A1 | 12/2011 | Govindan et al. |
| 2011/0319590 A1 | 12/2011 | Goletz et al. |
| 2012/0121615 A1 | 5/2012 | Flygare et al. |
| 2012/0128676 A1 | 5/2012 | Goletz et al. |
| 2012/0128678 A1 | 5/2012 | Aburatani et al. |
| 2012/0149877 A1 | 6/2012 | Goletz et al. |
| 2012/0171201 A1 | 7/2012 | Sapra |
| 2012/0201809 A1 | 8/2012 | Bhat et al. |
| 2012/0328634 A1 | 12/2012 | Govindan |
| 2013/0089872 A1 | 4/2013 | Nakamura et al. |
| 2013/0123178 A1 | 5/2013 | Dimarchi et al. |
| 2013/0216561 A1 | 8/2013 | Govindan |
| 2014/0004078 A1 | 1/2014 | Govindan |
| 2014/0099259 A1 | 4/2014 | Goletz et al. |
| 2015/0005474 A1 | 1/2015 | Goletz et al. |
| 2015/0297748 A1 | 10/2015 | Masuda et al. |
| 2015/0352224 A1 | 12/2015 | Naito et al. |
| 2015/0368363 A1 | 12/2015 | Goletz et al. |
| 2015/0374790 A1 | 12/2015 | Liu et al. |
| 2016/0279259 A1 | 9/2016 | Masuda et al. |
| 2016/0287722 A1 | 10/2016 | Govindan |
| 2016/0297890 A1 | 10/2016 | Agatsuma et al. |
| 2017/0021031 A1 | 1/2017 | Hettmann et al. |
| 2019/0151328 A1 | 5/2019 | Hettmann et al. |
| 2019/0216851 A1 | 7/2019 | Xiao et al. |
| 2019/0343953 A1 | 11/2019 | Goletz et al. |
| 2019/0359731 A1 | 11/2019 | Goletz et al. |
| 2020/0131275 A1 | 4/2020 | Goletz et al. |
| 2021/0107961 A1 | 4/2021 | Gellert et al. |
| 2021/0221910 A1 | 7/2021 | Gellert et al. |

FOREIGN PATENT DOCUMENTS

| | | |
|---|---|---|
| CA | 2859255 A1 | 6/2013 |
| CN | 1227499 A | 9/1999 |
| CN | 1764478 A | 4/2006 |
| CN | 101023100 A | 8/2007 |
| CN | 101490087 A | 7/2009 |
| CN | 102481364 A | 5/2012 |
| CN | 102574926 A | 7/2012 |
| CO | 20200013664 A2 | 12/2020 |
| DE | 43 29 004 | 3/1995 |
| EP | 0 117 060 A2 | 8/1984 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 1 167 537 A1 | 1/2002 |
| EP | 1 176 195 A1 | 1/2002 |
| EP | 1 333 032 | 8/2003 |
| EP | 1 371 735 A1 | 12/2003 |
| EP | 1 900 750 A1 | 3/2008 |
| EP | 1 911 766 A1 | 4/2008 |
| EP | 1 920 781 A1 | 5/2008 |
| EP | 2 281 844 A1 | 2/2011 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| JP | 05-059061 A | 3/1993 |
| JP | 06-087746 A | 3/1994 |
| JP | 08-337584 A | 12/1996 |
| JP | 10-095802 A | 4/1998 |
| JP | H11-071280 A | 3/1999 |
| JP | 11-092405 A | 4/1999 |
| JP | 2002-060351 A | 2/2002 |

(56) References Cited

FOREIGN PATENT DOCUMENTS

| | | |
|---|---|---|
| JP | 2005-503789 A | 2/2005 |
| JP | 2005-511627 A | 4/2005 |
| JP | 2006-511526 A | 4/2006 |
| JP | 2007-527872 A | 10/2007 |
| JP | 2007-530675 A | 11/2007 |
| JP | 2008-521828 A | 6/2008 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-500703 A | 1/2013 |
| JP | 2013-515675 A | 5/2013 |
| JP | 2013-534535 A | 9/2013 |
| JP | 2013-534906 A | 9/2013 |
| JP | 2017-503784 A | 2/2017 |
| KR | 1020010052385 A | 6/2001 |
| KR | 1020110044808 A | 4/2011 |
| LU | 92659 B1 | 8/2016 |
| RU | 2303069 C2 | 7/2007 |
| RU | 2404810 C2 | 7/2008 |
| RU | 2450008 C2 | 7/2010 |
| RU | 2016144178 A | 5/2018 |
| TW | 1232930 | 5/2005 |
| TW | 1232930 B | 5/2005 |
| TW | 200817434 A | 4/2008 |
| TW | 202003583 A | 1/2020 |
| WO | WO-92/15682 A1 | 9/1992 |
| WO | WO-93/13806 A1 | 7/1993 |
| WO | WO-93/20841 | 10/1993 |
| WO | WO-94/29469 A2 | 12/1994 |
| WO | WO-95/15769 A1 | 6/1995 |
| WO | WO-96/40210 A1 | 12/1996 |
| WO | WO-97/00957 A1 | 1/1997 |
| WO | WO-97/30087 A1 | 8/1997 |
| WO | WO-97/40182 A1 | 10/1997 |
| WO | WO-97/46260 A1 | 12/1997 |
| WO | WO-99/29834 A1 | 6/1999 |
| WO | WO-00/25825 A1 | 5/2000 |
| WO | WO-00/41576 A1 | 7/2000 |
| WO | WO-00/52135 A2 | 9/2000 |
| WO | WO-00/61739 A1 | 10/2000 |
| WO | WO-01/00244 A2 | 1/2001 |
| WO | WO-01/12217 | 2/2001 |
| WO | WO-01/75110 A2 | 10/2001 |
| WO | WO-02/00734 A1 | 1/2002 |
| WO | WO-02/30954 A1 | 4/2002 |
| WO | WO-02/44217 | 6/2002 |
| WO | WO-03/013602 A1 | 2/2003 |
| WO | WO-03/015826 A1 | 2/2003 |
| WO | WO-03/016329 A2 | 2/2003 |
| WO | WO-03/016466 A2 | 2/2003 |
| WO | WO-03/023023 A1 | 3/2003 |
| WO | WO-03/035636 A2 | 5/2003 |
| WO | WO-03/035686 A2 | 5/2003 |
| WO | WO-03/035835 A2 | 5/2003 |
| WO | WO-03/043583 A2 | 5/2003 |
| WO | WO-03/044051 A1 | 5/2003 |
| WO | WO-03/074566 A2 | 9/2003 |
| WO | WO-03/074679 A2 | 9/2003 |
| WO | WO-03/100060 A2 | 12/2003 |
| WO | WO-2004/009632 A2 | 1/2004 |
| WO | WO-2004/018659 A2 | 3/2004 |
| WO | WO-2004/050707 A2 | 6/2004 |
| WO | WO-2004/065423 A2 | 8/2004 |
| WO | WO-2005/016455 A2 | 2/2005 |
| WO | WO-2005/016962 A2 | 2/2005 |
| WO | WO-2005/017130 A2 | 2/2005 |
| WO | WO-2005/032454 A3 | 4/2005 |
| WO | WO-2005/040221 A1 | 5/2005 |
| WO | WO-2005/080585 A1 | 9/2005 |
| WO | WO-2005/102387 A2 | 11/2005 |
| WO | WO-2005/108423 A1 | 11/2005 |
| WO | WO-2005/112919 A2 | 12/2005 |
| WO | WO-2006/012616 A2 | 2/2006 |
| WO | WO-2006/065533 A2 | 6/2006 |
| WO | WO-2006/092230 A2 | 9/2006 |
| WO | WO-2006/125207 A2 | 11/2006 |
| WO | WO-2007/005786 A2 | 1/2007 |
| WO | WO-2007/034210 A1 | 3/2007 |
| WO | WO-2007/034210 A1 | 3/2007 |
| WO | WO-2007/077028 A2 | 7/2007 |
| WO | WO-2007/124992 A1 | 11/2007 |
| WO | WO-2008/028686 A2 | 3/2008 |
| WO | WO-2008/055702 A1 | 5/2008 |
| WO | WO-2008/055703 A2 | 5/2008 |
| WO | WO-2008/100624 A2 | 8/2008 |
| WO | WO-2008/101177 A2 | 8/2008 |
| WO | WO-2008/116219 A2 | 9/2008 |
| WO | WO-2008/119567 A2 | 10/2008 |
| WO | WO-2008/144891 A1 | 12/2008 |
| WO | WO-2009/149185 A2 | 12/2009 |
| WO | WO-2010/050528 A1 | 5/2010 |
| WO | WO-2011/011474 A1 | 1/2011 |
| WO | WO-2011/012309 A1 | 2/2011 |
| WO | WO-2011/021397 A1 | 2/2011 |
| WO | WO-2011/068845 A1 | 6/2011 |
| WO | WO-2011/080796 A1 | 7/2011 |
| WO | WO-2011/089004 A1 | 7/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/020065 A1 | 2/2012 |
| WO | WO-2012/064733 A2 | 5/2012 |
| WO | WO-2013/068946 A2 | 5/2013 |
| WO | WO-2013/077458 A1 | 5/2013 |
| WO | WO-2013/163229 A1 | 10/2013 |
| WO | WO-2013/188740 A1 | 12/2013 |
| WO | WO-2014/057687 A1 | 4/2014 |
| WO | WO-2014/061277 A1 | 4/2014 |
| WO | WO-2014/075788 A1 | 5/2014 |
| WO | WO-2014/107024 A1 | 7/2014 |
| WO | WO-2014/111509 A2 | 7/2014 |
| WO | WO-2015/014879 A1 | 2/2015 |
| WO | WO-2015/095418 A1 | 6/2015 |
| WO | WO-2015/111509 A1 | 7/2015 |
| WO | WO-2015/115091 A1 | 8/2015 |
| WO | WO-2015/116753 A1 | 8/2015 |
| WO | WO-2015/155998 A1 | 10/2015 |
| WO | WO-2015/159076 A1 | 10/2015 |
| WO | WO-2016/135079 A1 | 9/2016 |
| WO | WO-2016/146894 A1 | 9/2016 |
| WO | WO-2018/138113 A1 | 8/2018 |
| WO | WO-2018/178046 A1 | 10/2018 |
| WO | WO-2018/178047 A1 | 10/2018 |
| WO | WO-2018/178122 A1 | 10/2018 |
| WO | WO-2018/178123 A1 | 10/2018 |
| WO | WO-2019/166617 A1 | 9/2019 |

OTHER PUBLICATIONS

Feng. "Stressed apoptotic tumor cells express heat shock proteins and elicit tumor-specific immunity," Blood, 97:3505-3512 (2001).
Irazoqui et al., "Thomsen-Friedenreich Disaccharide Immunogenicity," Current Cancer Drug Targets, 2003, vol. 3, pp. 433-443.
U.S. Appl. No. 16/971,756, filed Aug. 21, 2020, Gellert et al.
International Preliminary Report on Patentability and Written Opinion issued in corresponding International Patent Application No. PCT/EP2019/062758, dated Nov. 24, 2020.
International Searching Authority, "International Search Report," issued in connection with International Patent Application No. PCT/EP2019/062758, dated Jul. 31, 2019.
International Searching Authority, "Written Opinion," issued in connection with International Patent Application No. PCT/EP2019/062758, dated Jul. 31, 2019.
Nakada et al., "Novel antibody drug conjugates containing exatecan derivative-based cytotoxic payloads," Bioorganic & Medicinal Chemistry Letters, vol. 26, Issue 6, Mar. 15, 2016, pp. 1542-1545.
Ogitani et al., "DS-8201a, A Novel HER2-Targeting ADC with a Novel DNA Topoisomerase I inhibitor, Demonstrates a Promising

(56) References Cited

OTHER PUBLICATIONS

Antitumor Efficacy with Differentiation from T-DM1," Clinical Cancer Research, vol. 22, No. 20, Oct. 15, 2016, pp. 5097-5108.
"Sequence 628 from Patent WO 2005/016962," (2005) XP002430727.
A) Esmo, 4745, "A Double-blind, placebo-controled, randomized, phase 2 study to evaluate the efficacy and safety of witch maintenance therapy with the anti-TA-MUC1 antibody PankoMab-GEX after chemotherapy in patients with recurrent epithelial ovarian carcinoma", 2017.
a) Human MUC-1 Antibody, MAB6298, Clone 604804.
B) Annals of Oncology, "Preliminary results in colorectal cancer (CRC) patients enrolled in the GATTO study, a phase I study of Tomuzotuximab in combination with Gatipotuzumab in patients with EGFR positive solid tumors", 2019, SO-010.
b) Anti-MUC1 antibody, [HMFG1 (aka 1.10.F3)] ab70475.
c) Anti-MUC1 antibody, [C595(NCRC48)] ab28081.
d) Anti-MUC1 antibody [EPR1023] ab109185.
Acchione et al., Impact of linker and conjugation chemistry on antigen binding, Fc receptor binding and thermal stability of model antibody-drug conjugates, mAbs, 2012, pp. 362-372.
Adams et al., "Humanization of a recombinant monoclonal antibody to produce a therapeutic HER dimerization inhibitor, pertuzumab," Cancer Immunol. Immunother. 55:717-727 (2006).
Adams, et al, "Enhanced Tumor Specificity of 741F8-1 (sFv')2, an Anti-c-erbB-2 Single-Chain Fv Dimer, Mediated by Stable Radioiodine Conjugation," Journal of Nuclear Medicine, 1995, vol. 36, pp. 2276-2281.
Additional experimental data, filed in EP2073842B1, (Annex 1 ), 7 pages (D34) (Feb. 6, 2012).
Advantages achieved with antibodies obtainable by the claimed production method—induction of target cell lysis, filed in EP2073842B1, (Annex 2), 4 pages (D35) (Jan. 14, 2011).
Advisory Action on U.S. Appl. No. 10/524,738 dated Jan. 29, 2009.
Advisory Action on U.S. Appl. No. 10/568,098 dated Jan. 14, 2010.
Advisory Action on U.S. Appl. No. 10/568,098 dated Oct. 7, 2009.
Advisory Action on U.S. Appl. No. 12/514,248 dated Jun. 27, 2013.
Agrawal, et al. "Cancer-associated MUC1 mucin inhibits human T-cell proliferation, which is reversible by IL-2.", Nall. Med., 4(1):43-9 (1998).
Albert, "Dendritic cells acquire antigen from apoptotic cells and induce class I-restricted CTLs," Nature, 392:86-89 (1998).
Alimandi et al., "Cooperative signaling of ErbB3 and ErbB2 in neoplastic transformation and human mammary carcinomas," Oncogene 10:1813-1821 (1995)—9 Pages.
Alley, S., et al., "Antibody-drug conjugates; targeted drug delivery for cancer", Current Opinion in Chemical Biology, No. 14, (2010), pp. 5-13.
Allison A. et al., "The role of cytokines in the action of immunological adjuvants," Vaccine Design the Role of Cytokine Networks. Gregoriadis ed., NATO ASI Series A: Life Sciences, vol. 293, pp. 1-9, Plenum Press, NY (1997).
Allowance dated Jul. 4, 2017, in JP 2016-117096.
Allowance issued in connection with Taiwanese Patent Application No. 104103127,dated Apr. 11, 2018.
Almagro, Juan C. et al., "Humanization of antibodies," Frontiers in Bioscience, vol. 13:1619-1633 (2008).
Alter et al., "Targeted IL-15-based Protein Fusion Complexes as Cancer Immunotherapy Approaches," Journal o Immunological Sciences, vol. 2(1):15-18 (2018).
Amit, M. et al., "Derivation and spontaneous differentiation of human embryonic stem cells", Journal of Anatomy, vol. 200: 225-232 (2002).
Anderson. "Human Gene Therapy". Science, vol. 256, 1992, pp. 808-813.
Australian Intellectual Property Office, "Examination Report No. 2 for Standard Patent Application," Australian Patent Application No. 2014371934, dated Sep. 13, 2019.
Baca et at, "Antibody Humanization Using Monovalent Phage Display," The Journal of Biological Chemistry, vol. 272, No. 16, Issue of Apr. 18, pp. 10678-10684 (1997).

Bagshawe, et al., "Antibody-Directed Enzyme Prodrug Therapy (ADEPT) for Cancer", Expert Opin. Biol. Ther., 2004, vol. 4, pp. 1777-1789.
Bain et al., "Structural Basis for Distinct Binding Properties of the Human Gaiectins to Thomsen-Friedenreich Antigen," PLoS One, Sep. 2011. vol. 6, Issue 9:e25007 (10 pgs).
Baldus, Stephan E. et al., "Coexpression of MUC1 Mucin Peptide Core and the Thomsen-Friedenreich Antigen in Colorectal Neoplasms," Cancer, vol. 82:1019-1027 (1998).
Barginear et al., "Trastuzumab-DM1: A Review of the Novel Immuno-Conjugate for HER2-Overexpressing Breast Cancer", The Open Breast Cancer Journal, Dec. 31, 2009 1:25-30.
Barok et al, "Trastuzumab-DM1 is highly effective in preclinical models of HER2-positive gastric cancer", Cancer Letters, 2011, vol. 306, No. 2, pp. 171-179.
Baselga et al., "Phase II Study of Weekly Intravenous Recombinant Humanized Anti-p185, Monoclonal Antibody in Patients with HER2/neu-Overexpressing Metastatic Breast Cancer," J. Clin. Oncol. 14(3):737-744 (Mar. 1996).
Basu et al., "The Epithelial/Carcinoma Antigen EGP-1 Recognized by Monoclonal Antibody RS ?- 3G11, is Phosphorylated on Serine 303," Int. J. Cancer 62(4):4 72-479 (1995).
Baumeister and Goletz, "Voll Funktionsfahige Humane Dendritische Zelllinie," Laborwelt [online], vol. 6, 2005, url:http:/, www.nemod. com/downloads/nemoddc%20IN%20laborwelt%207.2.05.pdf.
Baumeister et al., "Glyco-optimisation of biotherapeutics," Manufacturing Chemist, Dec. 2011, pp. 35-37.
Baumeister, "A novel human expression system for production of higher active biotherapeutics with optimised glycosylation," PharmaChem, 2006, vol. 5, No. 4, pp. 21-24.
Baumeister, H., "Glycoengineering-a Technology for Production of Glycoproteins," Journal of Biotechnology, Nov. 2004, pp. 10-11.
Baumeister, Hans et al., "GlycoExpress: A novel expression for the optimal glycosylation of biotherapeutics," Speciality Chemicals Magazine, pp. 46-48 (2005).
Beck et al., "The Next Generation of Antibody-Drug Conjugates Comes of Age," Discovery Medicine, Oct. 16, 2010, 10(53):329-339.
Behrens et al., Methods for site-specific drug conjugation to antibodies, mAbs, 2014, vol. 6, No. 1, pp. 46-53.
Benoist, H. et al., "Studies on the Susceptibility to NK-Mediated Lysis and the Simultaneous Expression of Various Surface Molecules in Anthracyclin-Treated K562 Cells and in Four K562 Cell Clones," Immunology Letters, vol. 34, pp. 45-55 (1992).
Berd, "Autologous hapten-modified melanoma vaccine as postsurgical adjuvant treatment after resection of nodal metastases," J. Clin. Oncol., 15:2359-2370 (1997).
Berthier-Vergnes. "Induction of IgG Antibodies Directed to a M.sub.r 31,000 Melanoma Antigen in Patients Immunized with Vaccinia Virus Melanoma Oncolysates," Cancer Res. 54:2433-2439 (1994).
Bibeau et al., "Impact of Fc{gamma}RIIa-Fc{gamma}RIIIa polymorphisms and KRAS mutations on the clinical outcome of patients with metastatic colorectal cancer treated with cetuximab plus irinotecan," J. Clin. Oncol. 27(7):1122-9, (2009).
Binder, "Cutting Edge: Heat Shock Protein gp96 Induces Maturation and Migration of CD11 c* Cells In Vivo," J. Immunol.; 165:6029-6035 (2000).
Blok et al., "Cytoplastic Overexpression of HER2: a Key Factor in Colorectal Cancer", Clinical Insights: Oncology, vol. 7, 2013 pp. 41-51.
Bluemel, C. et al., "Epitope distance to the target cell membrane and antigen size determine the potency of T cell-mediated lysis by BiTE antibodies specific for a large melanoma surface antigen," Cancer Immunol. Immunother., vol. 59 (8):1197-1209 (2010).
Boel, et al., "Functional Human Monoclonal Antibodies of All Isotypes Constructed from Phage Display Library-Derived Single-Chain Fv Antibody Fragments", J. Immunol. Methods, vol. 239, pp. 153-166, 2000.
Bohm et al., "Carbohydrate Recognition on MUC1-Expressing Targets Enhances Cytoxicity of a T cell Subpopulation", Scandinavian Journal of Immunology, vol. 46. No. 1, pp. 27-34. XP-002323076 (1997).

(56) References Cited

OTHER PUBLICATIONS

Bomford et al., "The control of the antibody isotype responses to recombinant human immunodeficiency virus gp120 antigen by adjuvants," Aids Res. Hum. Retroviruses, 8:1765 et seq. (1992).
Bonig et al. "Gylcosylated vs non-glycosylated granulocyte colony-stimulating factor (G-CSF)—results of a prospective randomised mononcentre study," Bone Marrow Trans. 25: 259-264 (2001).
Bourdon, "Inhibition of Tumoral Graft Growth by Pretreatment with Normal or Heat-modified Tumoral Cells," Ann. Immunology 1, 43-63 (1981).
Boyd, P.N. et al., "The effect of the removal of sialic acid, galactose and total carbohydrate on the functional activity of Campath-1 H," Molecular Immunology, vol. 23(17/18) pp. 1311-1318 (1995).
Brechbiel, et al., "Synthesis of 1 (p-Isothiocyanatobenzyl) Derivatives of DTPA and EDTA Antibody Labeling and Tumor-Imaging Studies", Inorg Chem, vol. 25, pp. 2772-2781, 1986.
Brummelkamp, et al. "A System for Stable Expression of Short Interfering RNAs in Mammalian Cells". Science, vol. 296, 2002, pp. 550-553.
Burgess, et al., "Possible dissociation of the heparin-binding and mitogenic activities of the heparin-binding (acidic fibroblast) growth factor-1 from its receptor binding activities by site directed mutagenesis of a single lysine residue.", Journal of Cell Biology, 1990. Vol. 111, pp. 2129-2138.
Burke et al., "Design, Synthesis, and Biological Evaluation of Antibody—Drug Conjugates Comprised of Potent Camptothecin Analogues," Bioconjugate Chemistry, Jun. 17, 2009, 20(6):1242-1250.
Burris, III et al., "Phase 11 Study of the Antibody Drug Conjugate Trastuzumab-DM1 for the Treatment of Human Epidermal Growth Factor Receptor 2 (HER2)—Positive Breast Cancer After Prior HER2-Directed Therapy," J. Clin. Oncol. 29(4):398-405 (Feb. 2011).
Butschak, G., et al., "Isolation and Characterization of Thomsen-Friedenreich-Specific Antibodies From Human Serum," Tumor Biology, vol. 23, No. 3, pp. 113-122 (2002).
Byrne, Barry et al., "Sialic acids: carbohydrate moieties that influence the biological and physical properties of biopharmaceutical proteins and living cells," Drug Discovery Today, vol. 12(7/8):319-326 (2007).
Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Cant, D. et al., "Glycosylation and functional activity of anti-D secreted by two human lymphoblastoid cell lines," Cytotechnology, vol. 15(1-3), pp. 223-228. (1994).
Cao et al., "Immunodetection of Epithelial Mucin (MUC1, MUC3) and Mucin-associated Glycotopes (TF, Tn, and sialosyl-Tn) in Benign and Malignant Lesions of Colonic Epithelium: Apolar Localization Corresponds to Malignant Transformation", VirchowsArchiv, vol. 431, No. 3, pp. 159-166, Xp-002323077, (1997).
Cao, Y. et al., "Expression of CD175 (Tn), CD175s (Sialosyl-Tn) and CD176 (Thomsen-Friedenreich Antigen) on Malignant Human Hematopoietic Cells," International Journal of Cancer, vol. 123, pp. 89-99 (2008).
Cao, Yi et al., "Binding patterns of 51 monoclonal antibodies to peptide and carbohydrate epitopes of the epithelial mucin (MUC1) on tissue sections of adenolymphomas of the parotid (Warthin's tumours): role of epitope masking by glycans," Histochem Cell Biol, vol. 115:349-356 (2001).
Cao, Yi et al., "Expression of MUC1, Thomsen-Friedenreich antigen, Tn, sialosyl-Tn, and alpha2,6-linked sialic acid in hepatocellular carcinomas and preneoplastic hepatocellular lesions," Virchows Arch, vol. 434:503-509 (1999).
Cao, Yi et al., "Expression of MUC1, Thomsen-Friedenreich-related antigens, and cytokeratin 19 in human renal cell carcinomas and tubular clear cell lesions," Virchows Arch, vol. 436:119-126 (2000).
Cao, Yi et al., "Immunohistochemical Characterization of a Panel of 56 Antibodies with Normal Human Small Intestine, Colon, and Breast Tissues," Tumor Biol., vol. 19(Suppl. 1):88-99 (1998).
Cao, Yi et al., "Mucins (MUC1 and MUC3) of Gastrointestinal and Breast Epithelia Reveal Different and Heterogeneous Tumor-associated Aberrations in Glycosylation," The Journal of Histochemistry & Cytochemistry, vol. 45(11 ):1547-1557 (1997).
Carbone, M. et al., "Multistep and Multifactorial Carcinogenesis: When Does a Contributing Factor Become a Carcinogen?," Seminars in Cancer Biology, vol. 14, pp. 399-405 (2004).
Cardillo, T., "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Casset, et al., "A peptide mimetic of an anti-CD4 monoclonal antibody by rational design", Biochemical and Biophysical Research Communications, 2003. vol. 307, pp. 198-205.
Cavaliere, "Selective heat sensitivity of cancer cells. Biochemical and clinical studies," Cancer 20:1351-1381 (1967).
Chames et al., "Bispecific antibodies for cancer therapy: the light at the end of the tunnel?", MAbs, 2009, vol. 1, No. 6, pp. 537-547.
Characterization of the claimed host cell lines and associated advantages when using these host cells for manufacturing glycoproteins, filed in EP2073842B1, (Annex 1 ), 4 pages (D36) (Jan. 14, 2011).
Check, "Protection against transplanted and spontaneous lymphoma by inoculation of heat-altered syngeneic tumor cells in splenectomized mice," Cancer, 34:197-203 (1974).
Chen Z. et al., "Efficient Antitumor Immunity Derived From Muturation of Dendritic Cells That had Phagocytosed Apoptotic/Necrotic Tumor Cells," International Journal of Cancer, vol. 93. No. 4, pp. 539-548 (2001).
Chen, Y., et al., "Selection and analysis of an optimized anti-VEGF antibody: crystal structure of an affinity-matured Fab in complex with antigen.", Journal of Molecular Biology, 1999. vol. 293, pp. 865-881.
Chinese Office Action issued to corresponding App. No. 201480071134.0—DTD Aug. 20, 2019 (5 pages).
Chinese Office Action issued to corresponding Application No. 201580019138.9 dated Nov. 8, 2019 (4 pages).
Chinese Search Report dated Jun. 24, 2020 for corresponding Application No. 108114649.
Chothia, et al., "Canonical Structures for the Hypervariable Regions of Immunoglobulins", J. Mol. Biol., vol. 196, pp. 901-917, 1987.
Chothia, et al., "Conformations of Immunoglobulin Hypervariable Regions", Nature, vol. 342, pp. 877-883, 1989.
Chothia, et al., "Structural Repertoire of the Human VH Segments", J. Mo/. Biol., vol. 227, pp. 799-817, 1992.
Chothia, et al., "The Predicted Structure of Immunoglobulin D1 .3 and its Comparison with the Crystal Structure", Science, vol. 233, pp. 755-758, 1986.
Clark, Mike, "Antibody humanization: a case of the 'Emperor's new clothes'?" Immunology Today, vol. 21(8):397-402 (2000).
Clausen, H., et al., "Monoclonal Antibodies Directed to the Blood Group a Associated Structure Galactosyl—A Specificity and Relation to the Thomsen-Friedenreich Antigen," Molecular Immunology, vol. 25, No. 2, pp. 199-204 (1988).
Clayman (ed.). The American Medical Association Encyclopedia of Medicine at 573-574, 576 and 1034 (1989).
Co, Man Sung et al., "Humanized antibodies for therapy," Nature, vol. 351:501-502 (1991).
Colombian Reconsideration Petition dated Mar. 15, 2018 in corresponding application No. NC2016/0000187.
Confirmation of Withdrawal of Application, European Application No. EP 06 090 171.7, dated Mar. 28, 2008, 1 page. (D8).
Confirmation of Withdrawal of Application, European Patent Application, EP 06 090 190. 7, dated Apr. 15, 2008, 1 page. (D9).
Constantinou, Antony et al., "Modulation of Antibody Pharmacokinetics by Chemical Polysialylation," Bioconjugate Chem., vol. 19:643-650 (2008).
Coussens et al., "Tyrosine Kinase Receptor with Extensive Homology to EGF Receptor Shares Chromosomal Location with neu Oncogene," Science 230(4730):1132-1139 (Dec. 1985).

(56) References Cited

OTHER PUBLICATIONS

Couto, Joseph R. et al., "Designing Human Consensus Antibodies with Minimal Positional Templates," Cancer Research, vol. 55:(Suppl.):5573s-5977s (1995).

Cox et al., "Adjuvants—A classification and review of their modes of action," Vaccine, vol. 15, pp. 248 et seq., (1997).

Cox et al., "Development of an Influenza-ISCOM.™ Vaccine," in Vaccine Design at pp. 33-49 (1997).

Croce, M.V., et al., "The Use of Carbohydrate Antigens for the Preparation of Vaccines for Therapy in Breast Cancer," Drugs of Today, vol. 38, No. 11, pp. 759-768 (2002).

Cryz, Jr., S.J., Immunotherapy and Vaccines, edited by Stanley J. Cryz, pp. 3-11, VCH, Weinheim, Germany (1991).

CV and Publications of Stephan Hinderlich filed in EP2073842B1, 3 pages (2016).

Czuczman, M. et al., "Treatment of Patients with Low-Grade B-Cell Lymphoma with the Combination of Chimeric Anti-CD20 Monoclonal Antibody and CHOP Chemotherapy," Journal of Clinical Oncology, vol. 17, No. 1, pp. 268-276 (1999).

Dai, J. et al., "Effect of desialylation on binding, affinity, and specificity of 56 monoclonal antibodies against MUC1 mucin," Tumor Biology, 1998, vol. 19 supp. 1, pp. 100-110.

Dall'Acqua, William F. et al., "Antibody humanization by framework shuffling," Methods, vol. 36:43-60 (2005).

Dall'Olio, et al., "Expression of beta-galactoside alpha 2,6-sialyltransferase does not alter the susceptibility of human colon cancer cells to NK-mediated cell lysis." Glycobiology_ 7:507-513 (1997).

Damle, Nitin K., "Tumour-targeted chemotherapy with immunoconjugates of calicheamicin," Expert Opin. Biol. Ther. 4(9):1445-1452 (2004)—8 Pages.

Danielezyk et al., "PankoMab: a potent new generation anti-tumor MUC1 anitbody", Cancer Immun Immunother, 2006, 55(11), pp. 1337-1347.

De Jager, R., et al., "DX-8951f: summary of phase I clinical trials", Annals New York Academy of Sciences, pp. 260-273.

De Pascalis, R. et al., "Grafting of "abbreviated" complementarity-determining regions containing specificity-determining residues essential for ligand contact to engineer a less immunogenic humanized monoclonal antibody.", Journal of Immunology, 2002. vol. 169, p. 3076-3084.

Decision to Grant issued Oct. 18, 2016, in Japanese Patent Application No. 2016-166850.

Defazio et al., "Expression of c-erbB Receptors, Heregulin and Oestrogen Receptor in Human Breast Cell Lines," Int. J. Cancer 87:487-498 (2000)—12 Pages.

Delwel, G. et al., "Expression and function of the cytoplasmic variants of the integrin alpha 6 subunit in transfected K562 cells. Activation-dependent adhesion and interaction with isoforms of laminin," The Journal of Biological Chemistry, vol. 268 (34), pp. 25865-25875 (1993).

Dermer, GB. Another Anniversary for the War on Cancer. Bio/Technology. 1994, vol. 12, p. 320.

Di Fiore et al., "erbB-2 Is a Potent Oncogene When Overexpressed in NIH/3T3 Cells," Science 237:178-182 (Jul. 1987).

Dian et al, "Staining of MUC1 in ovarian cancer tissues with PankoMab-GEX detecting the tumour-associated epitope, TA-MUC1, as compared to antibodies HMFG-1 and 115D8", Histol Histopathol, 2013, vol. 28, pp. 239-244.

Dian et al., "Evaluation of Novel Anti-Mucin 1 (MUC1) Antibody PankoMab as a Potential Diagnostic Tool in Human Ductal Breast Cancer; Comparison with Two Established Antibodies", Onkologie, 2009, vol. 32, pp. 238-244.

Dickson, "Hyperthermia in the treatment of cancer," Lancet, 1:202-205 (1979).

Dictionary of Immunology, pp. 3, 7, 46, 87-88, 94, 97, 105,116.

Dixon, "Evaluation of the CASP2 docking section", Proteins, 1997; Suppl 1, pp. 198-204).

Dorai, H., et al., "The Effect of Dihydrofolate Reductase-Mediated Gene Amplification on the Expression of Transfected Immunoglobulin Genes," Journal of Immunology (Baltimore, Md. 1950), Dec. 15, 1987, vol. 139, No. 12, pp. 4232-4241.

Dosio, F., et al., "Antibody-targeted leucinostatin A", Journal of Controlled Release, No. 32, (1994), pp. 37-44.

Dressel, "Heat Shock Protein 70 Is Able to Prevent Heat Shock-Induced Resistance of Target Cells to CTL," J. Immunol., 164:2362-2371 (2000).

Ducry, L., et al., "Antibody-Drug Conjugates: Linking Cytotoxic Payloads to Monoclonal Antibodies", Bioconjugate Chem., No. 21, (2009), pp. 5-13.

Duk et al., "Purification of Human Anti-TF (Thomsen-Friedenrelch) and Anti-Tn Antibodies by Affinity Chromatography on Glycophorin a Derivatives and Characterization of the Antibodies by Microtiter Plate ELISA", Archivum Immunologiae et TherapiaeExperimentalis, vol. 46, No. 2, pp. 69-77, XP-008045186, (1998).

El Sewedy et al., "Cloning of the Murine Trop2 Gene: Conservation of a PIP2-Binding Sequence in the Cytoplasmic Domain of Trop-2," Int. J. Cancer 75(2):324-330 (1998).

Elbashir, et al. "Duplexes of 21-nucleotide RNAs mediate RNA interference in cultured mammalian cells". Nature, vol. 411, 2001, pp. 494-498.

Endo, Tamao et al., "Glycosylation of the Variable Region of Immunoglobulin G-Site Specific maturation of the Sugar Chains," Molecular Immunology, vol. 32(13):931-940 (1995).

Engebraaten, O. et al., "Systemic immunotoxin treatment inhibits formation of human breast cancer metastasis and tumor growth in nude rats," International Journal of Cancer, vol. 88(6):970-976 (2000).

English-language translation of International Search Report issued in International Patent Application No. PCT/JP2015/002020 mailed Jul. 20, 2015—4 Pages.

Esteva et al., "A Phase II Study of Intravenous Exatecan Mesylate (DX-8951f) Administered Daily for 5 Days Every 3 Weeks to Patients with Metastatic Breast Carcinoma", American Cancer Society,2003,900-907.

Euhus, et al., "Appraisal of Anti-Idiotypic Antibodies in the Treatment of Solid Tumors in Humans", Surgery, Gynecology and Obstetrics, 1992, vol. 175(1 ), pp. 89-96.

European Office Action dated Jul. 20, 2011 for European Patent Application No. 09 745 554.7-1221.

European Patent Application 07 818 090.8, Annex 1, 4 pages, dated Jan. 14, 2011.

European Patent Application 07 818 090.8, Annex 1, Characterization of the Claimed Host Cell Lines and Associated Advantages When Using These Host Cells for Manufacturing Glycorpoteins, 4 pages, dated Jan. 14, 2011.

European Patent Application 07 818 090.8, Annex 2, 7 pages, dated Feb. 6, 2012.

European Patent EP2073842B1, "Data obtained by the opponent on the lines NM-H9D8-E6 and NM-H9D8-E6012," filed Feb. 16, 2015, pp. 1-22 (2015).

European Patent Office communication for European Patent Application No. 07 818 090.8-2406 dated Nov. 23, 2012 (5 pgs).

European Patent Office, "Extended European Search Report," issued in connection with European Patent Application No. 19206764.3., dated Feb. 4, 2020.

European Search Report for Application No. 11 17 6193.8, dated Apr. 16, 2012.

European Search Report for Application No. 11 17 6197.9, dated Apr. 12, 2012.

European Search Report for Application No. 11 17 6200.1, dated Apr. 12, 2012.

Experimental Test of the Cells DSM ACC 2807 (NM-H9D8-E6) and DSM ACC 2856 (NM-H9D8-E6Q12) filed in EP2073842B1 (D25) on Feb. 16, 2015, 22 pages.

Fan et al., "Reactivity of a humanized antibody (PankoMab) towards a tumor-related MUC1 epitope (TA-MUC1) with various human carcinomas", Pathology, 2010, vol. 206, pp. 585-589.

Faulk et al., "Antigens of human trophoblasts: A working hypothesis for their role in normal and abnormal pregnancies," Proc. Natl. Acad. Sci. USA 75(4):1947-1951 (1978).

(56) References Cited

OTHER PUBLICATIONS

Fendly et al., "Characterization of Murine Monoclonal Antibodies Reactive to Either the Human Epidermal Growth Factor Receptor or HER2/neu Gene Product," Cancer Research 50:1550-1558 (1990).

Ferencik, M. Handbook of Immunochemistry, p. 115-116. Chapman & Hall (1993).

Fernandes, D. et al., "Demonstrating comparability of antibody glycosylation during biomanufacturing," Eur Biopharmaceutical Rev., 106-110 (Summer 2005).

Fiebig, H.H., et al., "Clonogenic assay with established human tumor xenografts: correlation of in vitro to in vivo activity as a basis for anticancer drug discovery", European Journal of Cancer, 2004. vol. 40, pp. 802-820.

Fiedler et al., "A phase I study of PankoMab-GEX, a humanised glyco-optimised monoclonal antibody to a novel tumour-specific MUC1 glycopeptide epitope in patients with advanced carcinomas", Eur J Cancer, 2016, vol. 63, pp. 55-63.

Final Office Action issued in U.S. Appl. No. 15/221,851 mailed Nov. 13, 2017.

Final Office Action on U.S. Appl. No. 10/524,738 dated Aug. 4, 2008.

Final Office Action on U.S. Appl. No. 10/568,098 dated Jul. 23, 2009.

Final Office Action on U.S. Appl. No. 12/440,562 dated Oct. 13, 2011.

Final Office Action on U.S. Appl. No. 12/514,200 dated Feb. 22, 2013.

Final Office Action on U.S. Appl. No. 12/514,248 dated Apr. 11, 2013.

Final Office Action on U.S. Appl. No. 12/514,248 dated Apr. 20, 2016.

Final Office Action on U.S. Appl. No. 12/991,827 dated Nov. 19, 2013.

Final Office Action on U.S. Appl. No. 13/302,698 dated May 10, 2013.

Fogolin et al. "Choice of the adequate quantification method for recombinant human GM-CSF produced in different host systems," Electronic J. of Biotech. 5: 243-250 (2002).

Fong et al., "High expression of TROP2 correlates with poor prognosis in pancreatic cancer," Br. J. Cancer 99(8):1290-1295 (2008).

Fong et al., "TROP2: a novel prognostic marker in squamous cell carcinoma of the oral cavity," Mod. Pathol. 21(2):186-191 (2008).

Fornaro et al., "Cloning of the Gene Encoding Trop-2, a Cell-Surface Glycoprotein Expressed by Human Carcinomas," Int. J. Cancer 62(5):610-618 (1995).

Franco, A., "CTL-Based Cancer Preventive/Therapeutic Vaccines for Carcinomas: Role of Tumour-Associated Carbohydrate Antigens," Scandinavian Journal of Immunology, vol. 61, No. 5, pp. 391-397 (2005).

Freshney, R.I., Culture of Animal Cells, A Manual of Basic Technique, Alan R. Liss, Inc., 1983, New York. Page 4.

Fujiwara, "Establishment of a tumor-specific immunotherapy model utilizing TNP-reactive helper T cell activity and its application to the autochthonous tumor system," J. Immunol. 133:509-514 (1984).

Fukuda, M. et al. "Structures of novel sialyated O-linked oligosaccharides isolated from human erythrocyte glycophorins," The Journal of Biological Chemistry, 262(25):11952-11957 (1987).

Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).

Galluci, "Danger signals: SOS to the immune system," Curr. Opin. Immunol. 13:114-119 (2001 ).

Galluci, "Natural adjuvants: Endogenous activators of dendritic cells," Nat. Med. 11:1249-1255 (1991).

Geneseq, "DHFR-Synuclein Fusion Protein GST-ATSalpha Seq. ID No. 81," (2005) XP002430726.

Giovanella. "Effects of Elevated Temperatures and Drugs on the Viability of L 1210 Leukemia Cells," Cancer Res., 30:1623-1631 (1970).

Glycotope, "Turning Glycomics into Health," Biotech Business Opportunities in Germany, Bio 2006 Annual Convention in Chicago, 12 pages, (2006).

Goletz et al., "Binding patters of 33 TD-4(MUC1) Antibodies Towards Single-Chain Fragments and Peptides Mimicking the conformation of the MUC1 PDTRP Epitope", Tumor Biology, vol. 21, No. Supplement 1, Sep. 2000 , p. 142, XP008034905.

Goletz et at, "Bacterial-Derived Thomsen-Friedenreich Antigen Activates Specific T Cells via Presentation on Dendritic Cells," Glycobiology, Nov. 2011, 21/11 :1525 abstract Only.

Goletz, "Commensal Bacteria Expressing the Carbohydrate Human Tumour-Specific Antigen Gal.beta.1-3GaINAc. alpha.- (Thomsen-Friedenreich) as a Potential Tumour Vaccine," Glycobiology, Nov. 2011, 21/11 :1524 abstract only.

Goletz, S., "Turning Glycomics into Health," (2006) XP00243302.

Goletz, S., et al., "Thomsen-Friedenreich Antigen: The Hidden Tumor Antigen," Advances in Experimental Medicine and Biology, vol. 535, pp. 147-162 (2003).

Goletz, Steffen et al., "Selection of Large Diversities of Antiidiotypic Antibody Fragments by Phage Display," J_ Mal. Biol., vol. 315: 1087-1097 (2002).

Goletz, Steffen et al., "Structure Analysis of Acetylated and Non-acetylated O-Linked MUC1-Glycopeptides by Post-source Decay Matrix-assisted Laser Desorption/Ionization Mass Spectrometry," Rapid Communications in Mass Spectrometry, vol. 11:1387-1398 (1997).

Gollasch et al., "Identification of Immunogenic Peptide-Mimics for the Thomsen-Friedenreich-Glycoantigen"; Annals of Hematology, Berlin, DE, vol. 77, No. suppl. 2. p. S84, XP-000960533, (1998).

Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.

Gonzales, Noreen R. et al., "Minimizing the Immunogenicity of Antibodies for Clinical Application," Tumor Biol., vol. 26:31-43 (2005).

Gossow et al., "Systems for identifying new drugs are often faulty", Methods in Enzymology, 203:99-121 (1991).

Gough, M.J. et al., "Macrophages Orchestrate the Immune Response to Tumor Cell Death," Cancer Research 61, pp. 7240-7247 (2001).

Graus-Porta et al., "ERbB-2, the preferred heterodimerization partner of all ErbB receptors, is a mediator of lateral signaling," EMBO J. 16(7):1647-1655 (1997).

Gravalos et al., "HER2 in gastric cancer: a new prognostic factor and a novel therapeutic target," Ann. Oncol. 19:1523-1529 (2008).

Green, et al., "Activation-Induced Cell Death in T Cells", Immunological Reviews, 2003, vol. 193, pp. 70-81.

Grunberg, Elke et al., "Effects of Differentiation Inducers on Cell Phenotypes of Cultured Nontransformed and Immortalized Mammary Epithelial Cells: A Comparative Immunocytochemical Analysis," Tumor Biol., vol. 21 :211-223 (2000).

Gura, T., Systems for identifying new drugs are often faulty, Science, 1997, vol. 1997, vol. 128, pp. 1041-1042.

Hajirezaei, M. et al., "Cloning and expression of the functional human anti-vascular endothelial growth factor (VEGF) using the pcDNA3.1 vector and the human chronic myelogenous leukemia cell line K562," Protein J., vol. 33 (1), pp. 100-109 (2014).

Hardwick et al., "Immunohistochemical detection of p53 and c-erbB-2 in oesophageal carcinoma; no correlation with prognosis," Eur. J. Surg. Oncol. 23:30-35 (1997).

Henderson et al., "Occurrence of the humor tumor-specific antigen structure Gal.beta.1-3GaINAc.alpha.-(Thomsen-Friedenreich) and related structures on gut bacteria: Prevalence, immunochemical analysis and structural confirmation." vol. 21, No. 10.pp. 1277-1289 (2011 ).

Hermanson, G.T, Bioconjugate Techniques, pp. 56-136, pp. 456-493, Academic Press (1996).

Herrera et al., "Efficiency of Erythropoietin's Signal Peptide for HIVmn Expression", Biochem. Biophys. Res. Com. vol. 273, pp. 557-559, 2000.

(56) References Cited

OTHER PUBLICATIONS

Heubelin et al., "TA-MUC1 as detected by the fully humanized, therapeutic antibody Gatipotzumab predicts poor prognosis in cervical cancer", J Cancer Res Clinical Oncol, 2018, vol. 144, pp. 1899-1907.
Heublein et al., "Potential Interplay of the Gatipotuzumab Epitope TA-MUC1 and Estrogen Receptors in Ovarian Cancer", International Journal of Molecular Sciences, 2019, vol. 20, 295, pp. 1-14.
Hinoda, Y. et al., "Primary Structure of the Variable Regions of a Monoclonal Antibody MUSE11 Recognizing the Tandem Repeat Domain of a Mucin Core Protein, MUC1 ," Journal of Clinical Laboratory Analysis, vol. 7, pp. 100-104 (1993).
Hinoda, Y. et al.. "Circulating tumor-associated antigens detected by monoclonal antibodies against the polypeptide core of mucin: comparison of antigen MUSE11 with CA15-3," Gastroenterologia Japonica, 1992, vol. 27 No. 3, pp. 390-395.
Holm, P., et al., "Functional mapping and single chain construction of the anti-cytokeratin 8 monoclonal antibody TS1.", Molecular Immunology, 2007. vol. 44, pp. 1075-1084.
Hong, Y. et al. "Lec3 Chinese Hamster Ovary Mutants Lack UPD-N-acetylglucosamine 2-EPimerase Activity Because of Mutations in the Epimerase Domain of the Gne Gene," J. Biol. Chem 278(52):53045-53054 (2003).
Horm, T.M., et al., "MUC1 and metastatic cancer: Expression, function and therapeutic targeting," Cell Adhesion and Migration, vol. 7(2):187-198 (2013).
Hosse, RJ et al. "A new generation of protein display scaffolds for molecular recognition", Protein Science, 2006, vol. 15, pp. 14-27.
Hossler, P. et al., "Optimal and consistent protein glycosylation in mammalian cell culture," Glycobiol., vol. 19(9): 936-949 (2009).
Hsieh, et al., "Controlling Chemical Reactivity with Antibodies", Science, vol. 260, pp. 337-339 (1993).
Huang et al., "Heat-induced Gene Expression as a Novel Targeted Cancer Gene Therapy Strategy," Cancer Research 60:3435-3439 (2000).
Huang, L. et al., "Impact of variable domain glycosylation on antibody clearance: An LC/MS characterization," Anal Biochem., vol. 349:197-207 (2006).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
Hufton, S et al. "Development and application of cytotoxic T lymphocyte-associated antigen 4 as a protein scaffold for the generation of novel binding ligands." FEBS Letters, vol. 475 , Issue 3, pp. 225-231.
Hwang, William Ying Khee et al., "Immunogenicity of engineered antibodies," Methods, vol. 36:3-10 (2005).
Hwang, William Ying Khee et al., "Use of human germline genes in a CDR homology-based approach to antibody humanization," Methods, vol. 36:35-42 (2005).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
Ichiyama, "Induction of Non-HLA Restricted Anti-Tumor Effector Cells with Strong Cytoxic Activity Using MUC1/B7 Cotransfected K562 Cells," Cell Resource Center for Biomedical Research, Institute of Development, Aging, and Cancer, Tohoku University, Sendai, Japan, vol. 51, No. 3-4, pp. 93-110, XP-001182213 (2000).
Indian Office Action issued in the corresponding Indian Patent Application Ser. No. 201647013640, dated Jul. 19, 2019.
Inoue, K., et al., "CM-Dextran-Polyalcohol-Camptothecin Conjugate", Polymer Drugs in the Clinical Stage, (2003), pp. 145-153.
International Preliminary Report on Patentability and Written Opinion for Application No. PCT/EP2011/063791, 8 pages, dated Feb. 12, 2013.
International Preliminary Report on Patentability for Application No. PCT/EP2010/004663, dated Jan. 31, 2012.
International Preliminary Report on Patentability for Application No. PCT/EP2011/063791, dated Feb. 12, 2013.
International Preliminary Report on Patentability for Application No. PCT/EP2018/057846, dated Oct. 1, 2019.
International Preliminary Report on Patentability for Application No. PCT/EP2019/055125, dated May 13, 2019.
International Preliminary Report on Patentability on PCT/DE2004/000132 dated Jan. 21, 2005 with English language Translation.
International Preliminary Report on Patentability on PCT/EP2007/007877 dated Mar. 10, 2009.
International Preliminary Report on Patentability on PCT/EP2018/051652, dated Jul. 30, 2019.
International Preliminary Report on Patentability, PCT/EP2018/057721, dated Oct. 1, 2019.
International Search Report and Written Opinion for Application No. PCT/EP2011/063791, dated Jan. 18, 2012 (17 pages).
International Search Report and Written Opinion for Application No. PCT/EP2018/057846, dated Jun. 6, 2018.
International Search Report and Written Opinion for Application No. PCT/EP2019/055125, dated May 13, 2019.
International Search Report and Written Opinion for corresponding Application No. PCT/JP2018/007152 dated Apr. 24, 2018.
International Search Report and Written Opinion issued in International Patent Application No. PCT/JP2017/036215 dated Nov. 21, 2017 (19 pages).
International Search Report and Written Opinion on PCT/EP2018/051652, dated Mar. 19, 2018, 13 pages.
International Search Report and Written Opinion, PCT/EP2018/057721, dated Jun. 28, 2018, 11 pages.
International Search Report for Application No. PCT/EP2010/004663, dated Dec. 17, 2010.
International Search Report for corresponding Application No. PCT/JP2014/006421 mailed Mar. 17, 2015.
International Search Report for PCT Application No. PCT/EP2005/01593 (WO 2005/080585) dated Jul. 15, 2005.
International Search Report for PCT Application No. PCT/EP2007/007877 (WO 2008/028686 A3) dated Apr. 18, 2008.
International Search Report for PCT Application No. PCT/EP2007/009765 (WO 2008/055702 A1) dated Apr. 15, 2008, 7 pages.
International Search Report for PCT Application No. PCT/EP2007/009766 (WO 2008/055703 A2) dated Oct. 7, 2008, 7 pages.
International Search Report for PCT/DE2003/003994 (WO2004/050707) dated Aug. 10, 2004.
International Search Report for PCT/EP03/09140, (WO/2004/018659) dated Feb. 9, 2004, 8 pages.
International Search Report for PCT/EP2004/009281, (WO/2005/017130) dated Apr. 15, 2005.
International Search Report for PCT/JP2013/006069, dated Dec. 17, 2013.
International Search Report for PCT/JP2013/006178, dated Dec. 17, 2013.
International Search Report issued in International Patent Application No. PCT/JP2015/000355 mailed Apr. 21, 2015.
International Search Report on PCT/DE2004/000132 dated Sep. 23, 2004.
Interview summary dated Mar. 28, 2017, in CA 2885800.
Interview Summary on U.S. Appl. No. 10/568,098 dated Apr. 28, 2011.
Interview Summary on U.S. Appl. No. 10/568,098 dated May 5, 2011.
Isner, et al. "Clinical evidence of angiogenesis after arterial gene transfer of phVEGFI 65 in patient with ischaemic limb". The Lancet, vol. 348, 1996, pp. 370-374.
Iwahashi, Makoto et al., "CDR substitutions of a humanized monoclonal antibody (CC49): contributions of individual CDRs to antigen binding and immunogenicity," Molecular Immunology, vol. 36:1079-1091 (1999).
Jackson et al., "In vitro antibody maturation. Improvement of a high affinity, neutralizing antibody against IL-1 beta," J Immunol 154(7):3310-9 (1995).

(56) References Cited

OTHER PUBLICATIONS

Jacobs, C. L., et al., "Substrate specificity of the sialic acid biosynthetic pathway," Biochemistry, 40:12864-12874 (2001).
Jager, G. et al., "Treatment of Extranodal Marginal Zone B-Cell Lymphoma of Mucosa-Associated Lymphoid Tissue Type with Cladribine: A Phase II Study," Journal of Clinical Oncology, vol. 20, Issue 18, pp. 3872-3877 (2002).
Janne, P., et al., "Phase 1 study of the Anti-HER3 Antibody Drug Conjugate U3-1402 in Metastic or Unresectable EGFR-mutant NSCLC.", Journal of Thoracic Oncology, vol. 12, no. 11, Supp. Supplement 2, p. S2290, abstract No. P3.04-013, Nov. 2017 (3 pages).
Jefferis, R. et al., Glycosylation of Recombinant Antibody Therapeutics, Biotechnology Prog., vol. 21(1), pp. 11-16 (2005).
Jefferis, Roy, "Glycosylation of Antibody Therapeutics: Optimisation for Purpose," Methods in Molecular Biology, Recombinant Proteins From Plants, L. Faye (Ed.), Chapter 13, vol. 483:223-238 (2009).
Jenkins, N et al., "Getting the glycosylation right: implications for the biotechnology industry," Nat Biotechnology, vol. 14: 975-981 (1996).
Jensen, K.B. et al., "Functional improvement of antibody fragments using a novel phage coat protein III fusion system," Biochemical and Biophysical Research Communications, 2002, vol. 298, pp. 566-573.
Jescheke et al., "Determination of MUC1 in Sera of Ovarian Cancer Patients and in Sera of Patients with Benign Changes of the Ovaries with CA15-3, CA27.29, and PankoMab", Anticancer Research, 2012, vol. 32, pp. 2185-2190.
Jeschke, U. et al., "Expression of the Thomsen-Friedenreich Antigen and of its Putative Carrier Protein Mucin 1 in the Human Placenta and in Trophoblast Cells In Vitro," Histochemistry and Cell Biology, vol. 117, No. 3, pp. 219-226 (2002).
Jeschke, Udo et al., "The Human Endometrium Expresses the Glycoprotein Mucin-1 and Shows Positive Correlation for Thomsen-Friedenreich Epitope Expression and Galectin-1 Binding," Journal of Histochemistry & Cytochemistry, vol. 57(9):871-881 (2009).
Johnson, George et al., "Kabat Database and its applications: 30 years after the first variability plot," Nucleic Acids Research, vol. 28(1):214-218 (2000).
Jones, M. et al. "Characterization of the cellular uptake and metabolic conversion of acetylated N-acetylmannosamine (ManNAc) analogues to sialic acids," Biotechnology and Bioengineering, 85(4):394-405 (2004).
Joto, N., et al., "DX-8951F, A water-soluble camptothecin analog exhibits potent antitumor activity against a human lung cancer call line and its SN-38 resistant variant", Japan J. Cancer, No. 72, (1997), pp. 680-686.
Kalka-Moll, W et al., "Zwitterionic Polysaccharides Simulate T Cells by MHC Class II-Dependent Interactions," The Journal of Immunology, vol. 169, pp. 6149-6153 (2002).
Kanda Yutaka, et al., "Comparison of Cell Lines for Stable Production of Fucose-Negative Antibodies with Enhanced ADCC," Biotechnology and Bioengineering, Jul. 2006, vol. 94, No. 4, pp. 680-688.
Kaneko, Y., et al., "Anti-Inflammatory Activity of Immunogloubulin G Resulting from FC Sialylation," Science, American Association for the Advancement of Science, Aug. 2006, vol. 313, No. 5787, pp. 671-673.
Kang et al., "Engineering multivariant antibodies to target heregulin induced HER3 signaling in breast cancer cells", mAbs, Mar./Apr. 2014, vol. 6, No. 2, pp. 340-353.
Kaptain et al., "Her-2/neu and Breast Cancer," Diagn. Mol. Pathol. 10(3):139-152 (2001).
Karapetis et al., "Impact of FcγRIIa-FcγRIIIa Polymorphisms and KRAS Mutations on the Clinical Outcome of Patients with Metastatic Colorectal Cancer Treated with Cetuximab Plus Irinotecan," N. Engl. Med., 2008, Oct. 23; vol. 359, No. 17, pp. 1757-1765. doi: 10.1056/NEJMoa0804385.
Karsten et al. "Binding patterns of DTR-specific antibodies reveal a glycosylation-conditioned tumor-specific epitope of the epithelial mucin (MUC1)", Glycobiology, 2004, vol. 14, No. 8, pp. 681-692.
Karsten et al., "Enhanced Binding of Antibodies to the DTR Motif of MUC1 Tandem Repeat Peptide is Mediated by Site-Specific Glycosylation", Cancer Research, American Association for Cancer Research, Baltimore, MD, US, vol. 58, No. 12, pp. 2541-2549, XP-002112486, (Jun. 15, 1998).
Karsten, et al., "A New Monoclonal Antibody (A78-G/A7) to the Tomsen-Friedenreich Pan-Tumor Antigen", Hybridoma, vol. 14, No. 1, 1995, pp. 37-44, XP009034408.
Karsten, Uwe et al., "What Makes MUC1 a Tumor Antigen?" Tumor Biology, 26(4):217-220 (2005).
Karunagaran et al., "ErbB-2 is a common auxiliary subunit of NDF and EGF receptors: implications for breast cancer," EMBO J. 15(2):254-264 (1996).
Kashmiri, S.V.S. et al., "Development of a minimally immunogenic variant of humanized anti-carcinoma monoclonal antibody CC49," Critical Reviews in Oncology/Hematology, vol. 38:3-16 (2001).
Kashmiri, Syed V.S. et al., "SDR grafting—a new approach to antibody humanization," Methods, vol. 36:25-34 (2005).
Kawakami et al—"The anti-HER3 antibody patritumab abrogates cetuximab resistance mediated by heregulin in colorectal cancer cells", Oncotarget, vol. 5, No. 23, Dec. 5, 2014, 11847-11856—10 pages.
Keppler, O. et al. "UDP-GlcNAc 2-Epimerase: A Regulator of Cell Surface," Science 284:1372-1376 (1999).
Kettleborough, Catherine A. et al., "Humanization of a mouse monoclonal antibody by CDR-grafting: the importance of framework residues on loop conformation," Protein Engineering, vol. 4(7):773-783 (1991).
Kinoshita et al., "Glycosylation at the Fab portion of myeloma immunoglobulin G and increased fucosylated biantennary sugar chains: structural analysis by high-performance liquid chromatography and antibody-lectin enzyme immunoassay using Lens culinaris agglutinin," Cancer Research 51(21):5888-5892 (1991).
Klaamas, K., et al., "Expression of Tumor-Associated Thomsen-Friedenreich Antigen (T Ag) in Helicobacter Pylori and Modulation of T Ag Specific Immune Response in Infected Individuals," Immunological Investigations, vol. 31, No. 3/4, pp. 191-204 (2002).
Ko, et al., "Affinity Maturation of Monoclonal Antibody 1E11 by Targeted Randomization in CDR3 Regions Optimizes Therapeutic Antibody Targeting of HER2-Positive Gastric Cancer," PLoS One, 20(7):e0134600, p. 1-16, (2015).
Korkaya et al., "HER2 regulates the mammary stem/progenitor cell population driving tumorigenesis and invasion," Oncogene 27:6120-6130 (2008).
Kostelny, Sheri A. et al., "Humanization and Characterization of the Anti-HLA-DR Antibody 1D10," Int. J. Cancer, vol. 93:556-565 (2001).
Kotera, Y. et al., "Comparative Analysis of Necrotic and Apoptotic Tumor Cells as a Source of Antigen(s) in Dendritic Cell-Based Immunization," Cancer Research, vol. 61, No. 22, pp. 8105-8109 (2001).
Kozak, et al., "Nature of the Bifunctional Chelating Agent Used for Radioimmunotherapy with YTTRIUM-90 Monoclonal Antibodies: Critical Factors in Determining in vivo Survival and Organ Toxicity", Cancer Res., vol. 49, pp. 2639-2644, 1989.
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kuemmel et al., "TA-MUC1 epitope in non-small cell lung cancer", Lung Cancer, 2009, vol. 63, pp. 98-105.
Kumazawa, E. et al., "Antitumor activity of DX-8951f: a new camptothecin derivative", Expert Opinion Invest. Drugs, No. 7(4), (1998), pp. 625-632.

(56) References Cited

OTHER PUBLICATIONS

Kumazawa, E., et al., "DE-310 a novel macromolecular carrier system or the camptothecin analog DX-8951f: Potent antitumor activities in various murine tumor models", Cancer Sci, vol. 95, No. 2, (Feb. 2004) pp. 168-175.
Kumazawa, E., et al., "Potent and broad antitumor effects of DX-8951f, a water-soluble camptothecin derivative, against various human tumors xenografted in nude mice", Cancer Chemother Pharmacol, No. 42, (1998), pp. 210-220.
Kunz, "Synthetic Glycopeptides for the Development of Tumour-selective Vaccines", Journal of Peptide Science: an Official Publication of the European Peptide Society, vol. 9, No. 9, pp. 563-573, XP-00845163, (Sep. 2003).
Kurtenkov, O., et al., "Better Survival of Helicobacter Pylori Infected Patients With Early Gastric Cancer Is Related to a Higher Level of Thomsen-Friedenreich Antigen-Specific Antibodies," Immunological Investigations, vol. 32, No. 1-2, pp. 89-93(2003).
Lamminmaki et al. (JBC 2001, 276:36687-36694).
Langer, Robert, "New Methods of Drug Delivery," Science, 249(4976): 1527-1533 (1990).
Lazar, E., et al., "Transforming growth factor alpha: mutation of aspartic acid 4 7 and leucine 48 results in different biological activities.", Molecular and Cellular Biology, 1988. vol. 8, pp. 1247-1252.
Leffell, Mary S., "An Overview of the Immune System: The Molecular Basis for Immune Responses", Human Immunology Handbook, 1:1-45 (1997).
Lensink et al., "Docketing and scoring protein complexes: CAPRI 3d Edition", Proteins, 69(4):704-18 (2007) doi: 10.1002/prot. 21804.
Leung, Shui-On et al., "Construction and Characterization of a Humanized, Internalizing, B-Cell (CD22)-Specific, Leukemia/Lymphoma Antibody, LL2," Molecular Immunology, vol. 32(17/18):1413-1427 (1995).
Leung, Shui-on et al., "Engineering a Unique Glycosylation Site for Site-Specific Conjugation of Haptens to Antibody Fragments," The Journal of Immunology, vol. 154:5919-5926 (1995).
Leung, Shui-on et al., "The Effects of Domain Deletion, Glycosylation, and Long IgG3 Hinge on the Biodistribution and Serum Stability Properties of a Humanized IgGx Immunoglobulin hLL2, and Its Fragments," Clinical Care Research, vol. S:3106s-3117s (1999).
Li, Jia et al., "Where Do We Place PankoMab in the Reagents Used to Study the MUC1 Superfamily/" Onkologie, vol. 32:235-237 (2009).
Liao, et al., "Design of Transgenes for Efficient Expression of Active Chimeric Proteins on Mammalian Cells", Biotehnol Bioeng, vol. 73, pp. 313-323, 2000.
Libyh, et al., "A Recombinant Human scFv Anti-RH(D) Antibody with Multiple Valences Using a C-Terminal Fragment of C4-Binding Protein", Blood, 90(10), pp. 3978-3983, 1997.
Libyh, M. Tonye et al., "A recombinant human scFv anti-Rh(D) antibody with multiple valances using a C-terminal fragment of C4-binding protein," Blood, Nov. 15, 1997, vol. 90, No. 10, pp. 3978-3983.
Lifely, M.R., et al., "Glycosylation and Biological Activity of CAMPATH-1 H expressed in Different Cell Lines and Grown Under Different Culture Conditions," Glycobiology, vol. 5(8), pp. 813-822 (1995).
Linardou. Abstract. "Deoxyribonuclease I (DNAse I). A Novel Approach for Targeted Cancer Therapy," Cell Biophys., vol. 24-25, 243-248 (1994).
Linnenbach et al., "Sequence investigation of the major gastrointestinal tumor-associated antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
Lipscomb, M. et al., "Effect of production method and gene amplification on the glycosylation pattern of a secreted reporter protein in CHO cells," Biotechnol Prog., vol. 21: 40-49 (2005).

Liu et al., "A Novel Fusion of AIT-803 (Interleukin (IL)-15 Superagonist) with an Anti-body Demonstrates Antigen-specific Antitumor Responses," JBC, vol. 291(46):23869-23881 (2016).
Loo et al., "Development of an Fc-Enhanced Anti-B7-H3 Monoclonal Antibody with Potent Antitumor Activity," Clinical Cancer Research, vol. 18, No. 4, Jul. 15, 2012, pp. 3834-3845.
Lozzio and Lozzio, "Human Chronic Myelogenous Leukemia Cell-Line with Positive Philadelphia Chromosome," Blood 45(3):321-334 (1975).
Luftig, R.B., Microbiology and Immunology, pp. 228-229, Lippincott-Raven Pub, Phila. (1998).
Luo, Guang X. et al., "Humanization of an anti-ICAM-1 antibody with over 50-fold affinity and functional improvement," Journal of Immunological Methods, vol. 275:31-40 (2003).
Maccallum, R.M., et al., "Antibody-antigen interactions: contact analysis and binding site topography.", Journal of Molecular Biology, 1996. vol. 262, pp. 732-745.
Mach, "Cytokine-secreting tumor cell vaccines," Curr. Opin. Immunol. 12, 571-575 (2000).
Maclean, G.D., et al., "Active Immunization of Human Ovarian Cancer Patients Against a Common Carcinoma (Thomsen-Friedenreich) Determinant Using a Synthetic Carbohydrate Antigen," Journal of Immunotherapy, vol. 1, pp. 292-305 (1992).
Mantey, L. R., et al., "Efficient biochemical engineering of cellular sialic acids using an unphysiological sialic acid precursor in cells lacking UPD-N-acetylglucosamine 2-epimerase," FEBS Letters, 503:80-84 (2001).
Mariuzza et al., "The structural basis of antigen-antibody recognition", Annu. Rev. Biophys. Biophys. Chem. 1987, vol. 16, pp. 139-159.
Marshall, "Gut-Derived Organisms for Milk Fermentations," Centre for Sciences of Food and Nutrition, Oxford Polytechnic, Headington. Oxford OX30BP, UK, pp. 548-553, (1991).
Martin, et al., "Structural Families in Loops of Homologous Proteins: Automatic Classification, Modelling and Application to Antibodies", J. Mol. Biol., vol. 263, pp. 800-815, 1996.
Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.
Matsumoto-Takasaki et al., "Isolation and characterization of anti-T-antigen single chain antibodies from a phage library," BioScience Trends 3(3):87-95 (2009).
Matsuzaki, T., et al., "Antitumor Effect of Intrapleural Administration of Lactobacillus casei in Mice," Cancer Immunology Immunotherapy, vol. 26, No. 3, pp. 209-214 (1988).
Matzinger, P., "Tolerance, Danger, and the Extended Family," Annual Review in Immunology. vol. 12. pp. 991-1045 (1994).
Mazmanian, S. et al. "The Love-Hate Relationship Between Bacterial Polysaccharides and the Host Immune System.", Nature Reviews. vol. 6. pp. 849-858 (2006).
McDonagh et al., "Engineered antibody-drug conjugates with defined sites and stoichiometries of drug attachment," Protein Engineering, Design & Selection, 2006, 19(7):299-307.
Meibohm, "Pharmacokinetics and Pharmacodynamics of Biotech Drugs," Wiley-VHC, 2006, Chapter 3, p. 45-91).
Melcher, "Tumor immunogenicity is determined by the mechanism of cell death via induction of heat shock protein expression.", Nat Med. 4:581-587 (1998).
Melcher. "Apoptosis or necrosis for tumor immunotherapy: what's in a name?", J. Mol. Med. 77:824-833 (1999).
Millward, Thomas A. et al., "Effect of constant and variable domain glycosylation on pharmacokinetics of therapeutic antibodies in mice," Biologicals, vol. 36:41-47 (2008).
Mise, "Effect of Heat Treatment on Tumor Cells and Antitumor Effector Cells.", Cancer Res., vol. 50, pp. 6199-6202 (1990).
Mitchell, M. et al., "Active Specific Immunotherapy for Melanoma: Phase I Trial of Allogeneic Lysates and a Novel Adjuvant." Cancer Research. vol. 48. pp. 5883-5893 (1988).
Mitsui, I., "A New Water-Soluble Camptothecin Derivative, DX-8951f, Exhibits Potent Antitumor Activity against Human Tumors in vitro and in vivo", Japan J. Cancer Res. No. 86, (Aug. 1995), pp. 776-782.

(56) References Cited

OTHER PUBLICATIONS

Mivechi, "Heat Sensitivity, Thermotolerance, and Profile of Heat Shock Protein Synthesis of Human Myelogenous Leukemias," Cancer Research 49:1954-1958 (1989).
Moghaddas et al., "Whether HER2-positie non-breast cancers are candidates for treatment with Ado-trastuzumab emtansine?", J. Res Parm Pract, vol. 5(4), 2016 pp. 227-233.
Moller, Heicko et al., "NMR-based determination of the binding epitope and conformational analysis of MUC-1 glycopeptides and peptides bound to the breast cancer-selective monoclonal antibody SM3," European Journal of Biochemistry, 269(5):1444-1455 (2002).
Mondovi, "Increased immunogenicity of Ehrlich ascites cells after heat treatment.", Cancer. (30)4:885-888 (1972).
Mony, J. et al., "Ani-PD-L1 prolongs survival and triggers T cell but not humoral anti-tumor immune responses in a human MUC1-expressing preclinical ovarian cancer model," Cancer Immunology Immunotherapy, vol. 64, No. 9, pp. 1095-1108 (2015).
Morea, Veronica et al., "Antibody Modeling: Implications for Engineering and Design," Methods, vol. 20:267-279 (2000).
Mori, K. et al., "Engineering Chinese Hamster Ovary Cells to Maximize Effector Function of Produced Antibodies Using FUT8 siRNA," Biotechnology and Bioengineering, vol. 88 (7) pp. 901-908 (2004).
Morrison, et al., "Complement Activation and Fc Receptor Binding by IgG", Protein Engineering of Antibody Molecules for Prophylactic and Therapeutic Applications in Man, 1993, Mike Clark, Ed., pp. 101-113.
MSNBC News Services, Mixed results on new cancer drug. Nov. 9, 2000.
Mühlmann et al., "TROP2 expression as prognostic marker for gastric carcinoma," J. Clin. Pathol. 62(2):152-158 (2009).
Muramatsu et al., "Glycoprotein-Bound Large Carbohydrates of Early Embryonic Cells: Structural Characteristic of the Glycan Isolated from F9 Carcinoma Cells." J. Biochem. 94:799-810 (1983).
Mylonas, Ioannis et al., "Mucin 1, Thomsen-Friedenreich Expression and Galectin-1 Binding in Endometrioid Adenocarcinoma: An Immunohistochemical Analysis," Anticancer Research, vol. 27:1975-1980 (2007).
Nagahira, Kazuhiro et al., "Humanization of a mouse neutralizing monoclonal antibody against tumor necrosis factor-alpha (TNF-alpha)," Journal of Immunological Methods, vol. 222:83-92 (1999).
Naidu et al., "Expression of c-erbB3 protein in primary breast carcinomas," British Journal of Cancer 78(10): 1385-1390 (1998)—6 Pages.
Naito et al., "Generation of Novel Anti-MUC1 Monoclonal Antibodies with Designed Carbohydrate Specificities Using MUC1 Glycopeptide Library", ACS Omega, 2017, vol. 2, pp. 7493-7505.
Natali, et al., Heterogeneity in the expression of HLA and tumor-associated antigens by surgically removed and cultured breast carcinoma cells. Cancer Res 1983; 43:660-668.
Nath et al., "MUC1: a multifaceted oncoprotein with key role in cancer progression", Trends Mol. Med., 2014, vol. 20, No. 6, pp. 332-342.
NCI Drug Dictionary anti-TA-MUC1 monoclonal antibody PankoMab filed in EP2073842B1, 1 page.
Nicaise, Met al. "Affinity transfer by CDR grafting on a nonimmunoglobulin scaffold.", Protein Science (2004), vol. 13, pp. 1882-1891.
Nimmerjahn, F. et al., "Agalactosylated IgG antibodies depend on cellular Fc receptors for in vivo activity," PNAS, vol. 104(20): 8433-8437 (2017).
Ning et al., "TROP2 expression and its correlation with tumor proliferation and angiogenesis in human gliomas," Neurol. Sci. 34(10):1745-1750 (2013).
Non-Final Office Action in U.S. Appl. No. 10/540,479, filed Oct. 8, 2013.
Non-Final Office Action in U.S. Appl. No. 10/540,479 dated Oct. 8, 2013.
Non-Final Office Action in U.S. Appl. No. 10/524,738, filed Dec. 14, 2006.
Non-Final Office Action in U.S. Appl. No. 10/536,834 dated Feb. 19, 2009.
Non-Final Office Action issued in U.S. Appl. No. 14/435,114 mailed Jul. 21, 2016.
Non-Final Office Action issued in U.S. Appl. No. 14/436,458 mailed Jul. 19, 2016.
Non-Final Office Action issued in U.S. Appl. No. 15/180,203 mailed Jul. 25, 2016.
Non-Final Office Action issued in U.S. Appl. No. 15/221,851 mailed Jul. 7, 2017.
Non-Final Office Action issued Oct. 21, 2016, in U.S. Appl. No. 15/187,179.
Non-Final Office Action on U.S. Appl. No. 10/524,738 dated Aug. 10, 2007.
Non-Final Office Action on U.S. Appl. No. 10/524,738 dated Feb. 6, 2008.
Non-Final Office Action on U.S. Appl. No. 10/536,834 dated Aug. 5, 2010.
Non-Final Office Action on U.S. Appl. No. 10/536,834 dated Feb. 2, 2011.
Non-Final Office Action on U.S. Appl. No. 10/536,834 dated Nov. 10, 2009.
Non-Final Office Action on U.S. Appl. No. 10/568,098 dated Jan. 27, 2009.
Non-Final Office Action on U.S. Appl. No. 10/568,098 dated May 9, 2008.
Non-Final Office Action on U.S. Appl. No. 10/568,098 dated Sep. 29, 2010.
Non-Final Office Action on U.S. Appl. No. 10/589,447 dated Apr. 9, 2012.
Non-Final Office Action on U.S. Appl. No. 10/589,447 dated Aug. 26, 2011.
Non-Final Office Action on U.S. Appl. No. 10/589,447 dated Feb. 25, 2013.
Non-Final Office Action on U.S. Appl. No. 10/589,447 dated Feb. 3, 2011.
Non-Final Office Action on U.S. Appl. No. 12/440,562 dated Jul. 15, 2014.
Non-Final Office Action on U.S. Appl. No. 12/440,562 dated Oct. 28, 2010.
Non-Final Office Action on U.S. Appl. No. 12/514,200 dated Sep. 18, 2012.
Non-Final Office Action on U.S. Appl. No. 12/514,248 dated Dec. 26, 2014.
Non-Final Office Action on U.S. Appl. No. 12/514,248 dated Sep. 21, 2012.
Non-Final Office Action on U.S. Appl. No. 12/991,827 dated Mar. 18, 2013.
Non-Final Office Action on U.S. Appl. No. 13/208,253 dated Feb. 3, 2012.
Non-Final Office Action on U.S. Appl. No. 13/302,698 dated Nov. 7, 2012.
Non-Final Office Action on U.S. Appl. No. 14/102,214 dated Jan. 13, 2015.
Non-Final Office Action on U.S. Appl. No. 14/102,214 dated Jul. 22, 2015.
Non-Final Office Action on U.S. Appl. No. 14/703,498 dated Feb. 7, 2018.
Non-Final Office Action on U.S. Appl. No. 14/703,498 dated Jul. 26, 2017.
Non-Final Office Action on U.S. Appl. No. 14/703,498 dated Nov. 18, 2016.
Notice of Allowance in U.S. Appl. No. 10/540,479 dated Mar. 3, 2014.
Notice of Allowance issued in U.S. Appl. No. 15/187,179 mailed Aug. 25, 2017.
Notice of Allowance issued in U.S. Appl. No. 15/187,179 mailed May 18, 2017.
Notice of Allowance issued in U.S. Appl. No. 15/221,851 mailed Jun. 13, 2018.
Notice of Allowance on U.S. Appl. No. 10/524,738 dated May 19, 2009.

(56) References Cited

OTHER PUBLICATIONS

Notice of Allowance on U.S. Appl. No. 10/536,834 dated Aug. 25, 2011.
Notice of Allowance on U.S. Appl. No. 10/568,098 dated May 12, 2011.
Notice of Allowance on U.S. Appl. No. 10/589,447 dated Aug. 7, 2013.
Notice of Allowance on U.S. Appl. No. 12/440,562 dated Feb. 6, 2015.
Notice of Allowance on U.S. Appl. No. 12/514,200 dated Jun. 21, 2013.
Notice of Allowance on U.S. Appl. No. 12/514,248 dated Jul. 1, 2016.
Notice of Allowance on U.S. Appl. No. 12/991,827 dated Jan. 30, 2014.
Notice of Allowance on U.S. Appl. No. 13/208,253 dated Jun. 18, 2012.
Notice of Allowance on U.S. Appl. No. 13/302,698 dated Aug. 23, 2013.
Notice of Allowance on U.S. Appl. No. 14/102,214 dated Jan. 20, 2016.
Notice of Allowance on U.S. Appl. No. 14/703,498 dated Aug. 27, 2018.
Notice of Allowance on U.S. Appl. No. 14/703,498 dated Jan. 7, 2019.
Notice of Grounds for Rejection issued in connection with Korean Patent Application No. 10-2016-7015961, dated May 1, 2018.
Notice of Opposition filed in European Patent No. EP2073842B1, English Translation, dated Sep. 29, 2015, 184 pages.
Notice of Panel Decision from Pre-Appeal Brief Review on U.S. Appl. No. 10/568,098 dated Feb. 25, 2010 (2 pages).
Novina, et al. "siRNA-directed inhibition of HIV-1 infection". Nature Medicine, vol. 8, No. 7, 2002, pp. 681-686.
Nuttall, et al., "Design and Expression of Soluble CTLA-4 Varable Domain as a Scaffold for the Display of Functional Polypeptides", Proteins, vol. 36, pp. 217-227, 1999.
Nygren, et al., "Scaffolds for Engineering Novel Binding Sites in Proteins", Cur. Opin. Struc. Biol., vol. 7, pp. 463-469, 1997.
Ochi et al., "A possible mechanism for the long-lasting antitumor effect of the macromolecular conjugate DE-310: mediation by cellular uptake and drug release of its active camptothecin analog DX-8951," Cancer Chemotherapy and Pharmacology, Apr. 1, 2005, 55(4):323-332.
Office Action dated Dec. 6, 2016, in Japanese Application No. 2016-540705.
Office Action dated May 15, 2017, in TW 102136742.
Office Action dated Nov. 1, 2016, in Chinese Application No. 201380053256.2.
Office Action issued Apr. 22, 2016, in Singapore Patent Application No. 11201502887W.
Office Action issued in Colombia Application No. NC2016/0000187 dated May 9, 2017.
Office Action issued in connection with Canadian Patent Application No. 2,939,802, dated Apr. 13, 2018.
Office Action with Search Report dated Aug. 29, 2017, in RU 2015113767.
Ogitani et al., "Wide application of a novel topoisomerase I inhibitor-based drug conjugation technology," Bioorganic & Medicinal Chemistry Letters, vol. 26, 2016, 5069-5072.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
Oguma et al., Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26.

Ohmachi et al., "Clinical Significance of TROP2 Expression in Colorectal Cancer," Clin. Cancer Res. 12(10):3057-3063 (May 15, 2006).
Ohyama, et al. "Dual roles of sialyl Lewis X oligosaccharides in tumor metastasis and rejection by natural killer cells". The EMBO Journal, vol. 18, No. 6, 1999, pp. 1516-1525.
Ohyama, et al. "Natural killer cells attack tumor cells expressing high levels of sialyl Lewis x ollgosaccharides", PNAS, vol. 99, No. 21, 2002, pp. 13789-13794.
Olsvik, O. et al., "Magnetic Separation Techniques in Diagnostic Microbiology," Clinical Microbiology Reviews, vol. 7, No. 1, pp. 43-54 (1994).
Opposition dated May 3, 2017, against CO NC2016/0000187, with partial English translation.
Ouagari, et al. "Glycophorin A Protects K562 Cells from Natural Killer Cell Attack". The Journal of Biological Chemistry, vol. 270, No. 45, 1995, pp. 26970-26975.
Owens, et al. "Identification of two short internal ribosome entry sites selected from libraries of random oligonucleotides". PNAS, vol. 98, No. 4, 2001, pp. 1471-1476.
Pace, et al., "How to measure and predict the molar absorption coefficient of a protein," Protein Science, 1995, 4(11):2411-2423.
Paddison, et al. "Short hairpin RNAs (shRNAs) induce sequence-specific silencing in mammalian cells". Genes & Development, vol. 16, 2002, pp. 948-958.
Padlan et al., Structure of an antibody-antigen complex: crystal structure of the HyHEL-10 Fab-lysozyme complet, Proc. Natl. Acad. Sci, Aug. 1989, 86:5938-5942.
Pahlsson, et al., "Biochemical characterization of the O-glycans on recombinant glycophorin as expressed in Chinese hamster ovary cells.", Glycoconj. J., 11 :43-50 (1994).
Panka, D. et al., "Variable Region Framework Differences Result in Decreased or Increased Affinity of Variant Anti-Digoxin Antibodies," PNAS, vol. 85, No. 9, pp. 3080-3084 (1988).
PankoMab HEK / H9D8: Overlay chromatograms filed in EP2073842B 1 (D31) 3 pages (2016).
Pascal is, R. et al., "Grafting of 'Abbreviated' Complementarity-Determining Regions Containing Specificity—Determining Residues Essential for Ligand Contact to Engineer a Less Immunogenic Humanized Monoclonal Antibody," The Journal of Immunology, vol. 169, pp. 3076-3084 (2002).
Paul, W. E. (Ed.), Fundamental Immunology, p. 1007-1009, Raven Press, NY (1989).
Peach RJ et al. "Complementarity determining region 1 (CDR1)- and CDR3-analogous regions in CTLA-4 and CD28 determine the binding to 87-1." Journal of Experimental Medicine, vol. 180, 2049-2058.
Peters, L. et al., "Preparation of Immuno-Therapeutic Autologous Tumor Cell Vaccines from Solid Tumors," Cancer Research, vol. 39, pp. 1353-1360 (1979).
Phillips. T ., Analytical Techniques in Immunochemistry. pp. 307-310. Marcel Dekker. NY (1992).
Plowman et al., "Molecular cloning and expression of an additional epidermal growth factor receptor-related gene," Proc. Natl. Acad. Sci. USA 87:4905-4909 (Jul. 1990)—5 Pages.
Presta, L. "Selection, Design, and engineering of therapeutic antibodies," Molecular mechanisms in allergy and clinical immunology, J Allergy Clin Immunol., vol. 116:731-736 (2005).
Price et al. "Effect of heat and glutaraldehyde upon the immunogenicity of Meth A sarcoma cells." Br. J. Cancer 40:663-665 (1979).
Price M. et al., Summary Report on the ISOBM TD-4 Workshop: Analysis of 56 Monoclonal Antibodies against the MUC1 Mucin Tumor Biology Karger, Basel, CH, vol. 19, No. Suppl1, Dec. 1998 (Dec. 1998), pp. 1-20, XP002112482.
Printout of the page of the ATCC site "General information" for the line K562 bearing the No. ATCC CCL-243, Apr. 8, 2015, 1 page.
Product Sheet ATCC—293 [HEK-293] (ATCC CRL-1573TM) filed in EP2073842B1 (D29) 3 pages (2016).
Queen, Cary et al., "A humanized antibody that binds to the interleukin 2 receptor," Proc. Natl. Acad. Sci. USA, vol. 86:10029-10033 (1989).

(56) References Cited

OTHER PUBLICATIONS

Raju et al., "Glycoengineering of Therapeutic Clycoproteins: In Vivo Galactosyation and Sialylation of Glycoproteisn with Terminal N-Acetylgulocosamine and Galactose Residues," Biochemistry, pp. 8868-8876 (2001).
Raju, T. S. et al., "Species-specific variation in glycosylation of IgG: evidence for the species-specific sialylation and branch-specific galactosylation and importance for engineering recombinant glycoprotein therapeutics," Glycobiology, vol. 10(5), pp. 477-486 (2000).
Raska et at., "Glycosylation Patterns of HIV-1 gp120 Depend on the Type of Expressing Cells and Affect Antibody Recognition." Journal of Biological Chemistry. vol. 285. No. 27. Jul. 2, 2010. pp. 20860-20869.
Ravn at al.. "Thomsen-Friedertreich disaccharide as antigen for in vivo tumor targeting with multivalent scFvs." Cancer Immunol Immunother (2007) 56:1345-1357.
Reitman, et al., "Mouse lymphoma cell lines resistant to pea lectin are defective in fucose metabolism," The Journal of Biological Chemistry, 255(20):9900-9906 (1983).
Report on experimental tests of the cells DSM ACC 2807 (NM-H9D8-E6) and ; DSM ACC 2856 (NM-H9D8-E6Q12) filed in EP2073842B1 11 pages (2016).
Restifo, "Building better vaccines: how apoptotic cell death can induce inflammation and activate innate and adaptive immunity.", Curr. Opin. Immunol. 12:597-603 (2000).
Restriction Requirement on U.S. Appl. No. 10/524,738 dated Oct. 5, 2006.
Restriction Requirement on U.S. Appl. No. 10/536,834 dated Jun. 23, 2008.
Restriction Requirement on U.S. Appl. No. 12/514,200 dated Nov. 30, 2011.
Restriction Requirement on U.S. Appl. No. 13/302,253 dated Nov. 16, 2011.
Richter, D.U. et al., "Expression of the Thomsen-Friedenreich (TF) Antigen in the Human Placenta," Anticancer Research, vol. 20:5129-5134 (2000).
Riechmann, Lutz et al., "Reshaping human antibodies for therapy," Nature, vol. 332:323-327 (1988).
Riemer, AB et al., "Induction of IgG antibodies against the GD2 carbohydrate tumor antigen by vaccination with peptide mimotopes.", European Journal of Immunology. 36(5):1267-1274 (2006).
Ripani et al., "Human Trop-2 is a Tumor-Associated Calcium Signal Transducer," Int. J. Cancer 76(5):671-676 (1998).
Ripka, J., et al., "Lectin-Resistant CHO Cells: Selection of Four New Pea Lectin-Resistant Phenotypes," Somatic Cell and Molecular Genetics, vol. 12 (1), pp. 51-62(1986).
Roguska, Michael A. et al., "A comparison of two murine monoclonal antibodies humanized by CDR-grafting and variable domain resurfacing," Protein Engineering, vol. 9(10):895-904 (1996).
Roguska, Michael A. et al., "Humanization of murine monoclonal antibodies through variable domain resurfacing," Proc. Natl. Acad. Sci. USA, vol. 91 :969-973 (1994).
Romani et al., "Proliferating dendritic cell progenitors in human blood.", J. Exp. Med., vol. 180, pp. 83-93 (1994).
Rooman, et al., "Amino Acid Sequence Templates Derived from Recurrent Turn Motifs in Proteins: Critical Evaluation of Their Predictive Power", Protein Eng., vol. 3, pp. 23-27, 1989.
Rosebrough, S.F. et al., "Isothiocyanate-Trigalactose: Application for Antibody-Targeted Delivery of Diagnostic and Therapeutic Agents," Cancer Biotherapy & Radiopharmaceuticals, vol. 15(5):507-515 (2000).
Rosok, M., et al., "A Combinatorial Library Strategy for the Rapid Humanization of Anticarcinoma BR96 Fab." The Journal of Biological Chemistry, vol. 271 (37):22611-22618 (1996).
Rowinsky, Preclinical and Clinical Development of Exatecan(DX-8951f), Camptothecins in Cancer Therapy, 2005, pp. 317-318.
Rudikoff, S., et al., "Single amino acid substitution altering antigen-binding specificity", Proceedings of the National Academy of Sciences, 1982. vol. 79, pp. 1979-1983.

Running Deer, A. et al., "High-level Expression of Proteins in Mammalian Cells Using Transcription Regulatory Sequences from the Chinese Hamster EF-1alpha Gene," Biotechnol. Prag., vol. 20 (3), pp. 880-889 (2004).
Russian Office Action dated Mar. 5, 2019 in corresponding application No. 2016143351.
Russian Office Action dated Oct. 11, 2018 in corresponding application No. 2016123597.
Saerens D et al., "Identification of a Universal VHH Framework to Graft Non-canonical Antigen- binding Loops of Camel Single-domain Antibodies." Journal of Molecular Biology, vol. 352, Issue 3, Sep. 23, 2005, pp. 597-607.
Saldanha, Jose W. et al., "A single backmutation in the human kIV framework of a previously unsuccessfully humanized antibody restores the binding activity and increases the secretion in cos cells," Molecular Immunology, vol. 36:709-719 (1999).
Samali et al., "Thermotolerance and Cell Death are Distinct Cellular Responses to Stress: Dependence on Heat Shock Proteins," FEBS Letters 461(3):306-310 (1999).
Sandhu, Jasbir Singh, "A rapid procedure for the humanization of monoclonal antibodies," Gene, vol. 150:409-410 (1994).
Santegoets, S. et al., "In Vitro Priming of Tumor-Specific Cytotoxic T Lymphocytes Using Allogeneic Dendritic Cells Derived from the Human MUTZ-3 Cell Line," Cancer Immunology Immunotherapy, vol. 55, No. 12, pp. 1480-1490 (2006).
Sato, Koh et al., "Humanization of a Mouse Anti-Human Interleukin-6 Receptor Antibody Comparing Two Methods for Selecting Human Framework Regions," Molecular Immunology, vol. 31(5):371-381 (1994).
Sato, Koh et al., "Humanization of an anti-human IL-6 mouse monoclonal antibody glycosylated in its heavy chain variable region," Hum. Antibod. Hybridomas, vol. 7:175-183 (1996).
Sato, Koh et al., "Reshaping a Human Antibody to Inhibit the Interleukin 6-dependent Tumor Cell Growth," Cancer Research, vol. 53:851-856 (1993).
Sauter et al., "Consequences of Cell Death: Exposure to Necrotic Tumor Cells, but Not Primary Tissue Cells or Apoptotic Cells, Induces the Maturation of Immunostimulatory Dendritic Cells," Journal of Experimental Medicine, vol. 191, No. 3,pp. 423-433 (2000).
Savvidou, et al., "Possible role for peptide-oligosaccharide interactions in differential oligosaccharide processing at asparagine-107 of the light chain and asparagine-297 of the heavy chain in a monoclonal IgG," Biochemistry, 1984, vol. 23, pp. 3736-3740.
Scallon, Bernard J. et al., "Higher levels of sialylated Fc glycans in immunoglobulin G molecules can adversely impact functionality," Molecular Immunology, vol. 44:1524-1534 (2007).
Scheibel, T., et al., "Contribution of N- and C-terminal domains to the function of Hsp90 in *Saccharomyces cerevisiae*", Molecular Microbiology, 1999. vol. 34, pp. 701-713.
Schild, "gp96—the immune system's Swiss army knife," Nat. Immunol. 1:100-101 (2000).
Schlaeth et al., "Fc-engineered EGF-R antibodies mediate improved antibody-dependent cellular cytotoxicity (ADCC) against KRAS-mutated tumor cells," Cancer Sci. 101(5):1080-8. doi: 10.1111/j.1349-7006.2010.01505.x. Epub Jan. 20, 2010.
Schlapschy, Martin et al., "Functional humanization of an anti-CD30 Fab fragment for the immunotherpy of Hodgkin's lymphoma using an in vitro evolution approach," Protein Engineering, Design & Selection, vol. 17 (12):847-860 (2004).
Schlom, Jeffrey, "Monoclonal Antibodies: They're More and Less Than You Think," Molecular Foundation of Oncology, Samuel Broder (Ed.), William & Wilkins, Baltimore, Chapter 6, pp. 95-134 (1991).
Schneider, et al., "Thermostability of Membrane Protein Helix-Helix Interaction Elucidated by Statistical Analysis", FEBS Lett, 2002, vol. 532, pp. 231-236.
Schneider, F. et al., "Overexpression of Sialyltransferase CMP-Sialic Acid: Gal.beta.1,3BaINAc-R.alpha.6-Sialyltransferase is Related to Poor Patient Survival in Human Colorectal Carcinomas," Cancer Research, vol. 61, No. 11, pp. 4605-4611 (2001).
Selawry, "Hyperthermia in Tissue-cultured Cells of Malignant Origin," Cancer Res., 17:785-791 (1957).

(56) References Cited

OTHER PUBLICATIONS

Sensi, "Clonal Expansion of Lymphocytes in Human Metastases after Treatment With a Hapten-modified Autologous Tumor Vaccine," Clin. Invest. 99:710-717 (1997).
Senter, P., et al., "The discovery and development of brentuximab vedotin for use in relapsed Hodgkin lymphoma and systemic anaplastic large cell lymphoma", Nature Biotechnology, vol. 30, No. 7, (Jul. 2012), pp. 631-637.
Sergina, N.V., et al. "Escape from HER-family tyrosine kinase inhibitor therapy by the kinase-inactive HER3", Nature, vol. 445, pp. 437-441, 2007 (6 pages).
Shaif-Muthana, "Dead or Alive: Immunogenicity of Human Melanoma Cells When Presented by Dendritic Cells," Cancer Res., 60:6441-6447 (2000).
Shen et al., Conjugation site modulates the in vivo stability and therapeutic activity of antibody-drug conjugates, Nature Biotechnology, 2012, vol. 30, pp. 184-189.
Shields, RL et al., "Lack of fucose on human IgG1 N-linked oligosaccharide improves binding to human Fcgamma RIII and antibody-dependent cellular toxicity," The Journal of Biological Chemistry, vol. 277 (30) pp. 26733-26740 (2002).
Shinkawa, T. et al. "The Absence of Fucose but Not the Presence of Galactose or Bisecting N-Acetylglucosamine of Human IgG1 Complex-type Oligosaccharides Shows the Critical Rile of Enhancing Antibody-dependent Cellular Cytotoxicity," The Journal of Biological Chemistry, 278(5):3466-3473 (2003).
Shiose et al., "Relationship between Drug Release of DE-310, Macromolecular Prodrug of DX-8951f, and Chathespins Activity in Several Tumors," Biol. Pharm. Bull., 2007, 30(12):2365-2370.
Shiose et al., "Systematic Research of Peptide Spacers Controlling Drug Release from Macromolecular Prodrug System, Carboxymethyldextran Polyalcohol-Peptide-Drug Conjugates," Bioconiugate Chem., Jan. 1, 2009, 20(1):60-70.
Sievers et al, Antibody-Drug Conjugates in Cancer Therapy, Annual Review of Medicine, 2013, vol. 64, No. 1, pp. 15-29.
Sigma-Aldrich catalog, "Granulocyte Macrophage Colony—Stimulating Factor Human", downloaded 2011, 2 pages.
Singer, Irwin I. et al., "Optimal Humanization of 1 B4, an Anti-CD18 Murine Monoclonal Antibody, Is Achieved by Correct Choice of Human V-Region Framework Sequences," The Journal of Immunology, vol. 150(7):2844-2857 (1993).
Sivanandham, et al. "Cancer Vaccines: Clinical Applications". Principles and Practice of the Biologic Therapy of Cancer, Third Edition, S. Rosenberg, 2000, pp. 632-647, Lippincott Williams & Wilkins, Philadelphia, PA.
Skerra, "Engineered Protein Scaffolds for Molecular Recognition", J. Mol. Recog., vol. 13, pp. 167-187, 2000.
Skerra, A et al. "Alternative non-antibody scaffolds for molecular recognition." Current Opinion in Biotechnology, 2007, vol. 18, pp. 295-303.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Nonclinical Studies Addressing the Mechanism of Action of Trastuzumab (Herceptin)," Semin. Oncol. 26(4) Suppl. 12: 60-70 (Aug. 1999).
Sliwkowski et al., "Coexpression of erbB2 and erbB3 Proteins Reconstitutes a High Affinity Receptor for Heregulin." J. Biol. Chem. 269(20):14661-14665 (1994).
Slovin, S.F., et al., "Thomsen-Friedenreich (TF) Antigen as a Target for Prostate Cancer Vaccine: Clinical Trial Results With TF cluster (c)-KLH Plus QS21 Conjugate Vaccine in Patients With Biochemically Relapsed Prostate Cancer," Cancer Immunology Immunotherapy, vol. 54, No. 7, pp. 694-702 (2005).
Snippe et al., "Adjuvant Directed Immune Specificity at the Epitope Level. Implications for Vaccine Development. A Model Study Using Semliki Forest Virus Infection of Mice," Vaccine Design: The Role of Cytokine Networks, pp. 155-166 (1997).

Soepenberg et al., "Liquid chromatographic assays for DE-310, a novel camptothecin analog, and two major enzymatic products in human matrices," Journal of Chromatography B, 2004, 799:15-22.
Soepenberg, O., et al., "Phase I and Pharmacokinetic Study of DE-310 in Patients with Advanced Solid Tumors", Clinical Cancer Research, vol. 11, (Jan. 15, 2005) pp. 703-711.
Sola, Ricardo J. et al., "Glycosylation of Therapeutic Proteins, An Effective Strategy to Optimize Efficacy," Biodrugs, vol. 24(1):9-21 (2010).
Somersan S. et al., "Primary Tumor Tissue Lysates Are Enriched in Heat Shock Proteins and Induce the Maturation of Human Dendritic Cells, "Journal of Immunology, vol. 167, No. 9, pp. 4844-4852 (2001).
Sorensen, Anne Louise et al., "Chemoenzymatically synthesized multimeric Tn/STn MUC1 glycopeptides elicit cancer-specific anti-MUC1 antibody responses and override tolerance," Glycobiology, 16(2):96-107 (2005).
Soulieres et al., "KRAS mutation testing in the treatment of metastatic colorectal cancer with anti-EGFR therapies," Curr Oncol. Suppl 1(Suppl 1):S31-40 (2010) doi: 10.3747/co.v17is1.614.
Springer, et al., "Immunoreactive T and Tn epitopes in cancer diagnosis, prognosis, and immunotherapy." J. Mol. Med., 75:594-602 (1997).
Springer, G.F., et al., "Origin of Anti Thomsen Friedenreich and TN Agglutinins in Man and in White Leghorn Chicks," British Journal of Haematology, vol. 47, No. 3, pp. 453-460 (1981).
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Stimmel, et al., "YTTRIUM-90 Chelation Properties of Tetraazatetraacetic Acid Macrocycles, Diethylenetriaminepentaacetic Acid Analogues, and a Novel Terpyridine Acyclic Chelator", Bioconjug Chem., vol. 6, pp. 219-225, 1995.
Stork et al., "N-Glycosylation as Novel Strategy to Improve Pharmacokinetic Properties of Bispecific Single-chain Diabodies," The Journal of Biological Chemistry, vol. 283, No. 12, Mar. 21, 2008, pp. 7804-7812.
Supplemental Examiner's Amendment on U.S. Appl. No. 12/440,562, filed Mar. 20, 2015.
Supplementary European Search Report dated Aug. 11, 2017, in EP 15776810.2.
Supplementary European Search Report dated Aug. 9, 2017, in EP 15743738.5.
Supplementary European Search Report dated May 10, 2017 in EP 14874745.4.
Supplementary European Search Report dated May 13, 2016, in EP 13847461.4.
Supplementary European Search Report dated May 6, 2016, in EP 13845596.9.
Suzuki, T. et al., "A Comparison of the Genotoxicity of Ethylnitrosourea and Ethyl Methanesulfonate in lacZ Transgenic Mice (Muta.™. Mouse)," Mutation Research, vol. 395, pp. 75-82 (1997).
Tachibana et al., "Altered Reactivity of Immunoglobulin Produced by Human-Human Hybridoma Cells Transfected by pSV2-neo gene," Cytotechnology, 1991, vol. 6, pp. 219-226.
Taiwanese Office Action dated Jul. 20, 2018 in corresponding application No. 104111534.
Takahashi et al., "Antitumor Effects of the Intravesical Instillation of Heat Killed Cells of the Lactobacillus casei Strain Shirota on the Murine Orthotopic Bladder Tumor MBT-2," Journal of Urology, vol. 166, No. 6, pp. 2506-2511 (2001).
Takano, Y., et al., "Lymph Node Metastasis-Related Carbohydrate Epitopes of Gastric Cancer With Submucosal Invasion," Surgery Today 2000, vol. 30, No. 12, pp. 1073-1082 (2000).
Takiguchi, S., et al., "Antitumor Effect of DX-895, a Novel Camptothecin Analog, on Human Pancreatic Tumor Cells and Their CPT-11-resistant Variants Cultured in vitro and Xenografted into Nude Mice", Japan J. Cancer Res., No. 88, (Aug. 1997), pp. 760-769.
Tame, "Scoring functions: a view from the bench," J. Comput. Aided Mol. Des., 13(2):99-108 (1999).

(56) References Cited

OTHER PUBLICATIONS

Thatcher, N. et al., "Anti-T Antibody in Malignant Melanoma Patients, Influence of Response Survival Following Chemotherapy—Changes in Serum Levels Following C parvum, BCG Immunization," Cancer, vol. 46, No. 6, pp. 1378-1382 (1980).
Todryk. "Heat shock protein 70 induced during tumor cell killing induces Th1 cytokines and targets immature dendritic cell precursors to enhance antigen uptake." The Journal of Immunology, 163:1398-1408 (1999).
Tsurushita, et al., "Design of humanized antibodies: From anti-Tac to Zenapax," Methods, 36(1):69-83 (2005).
U.S. Office Action dated Apr. 5, 2019 in U.S. Appl. No. 15/821,697.
U.S. Patent and Trademark Office, "Non-Final Office Action", issued in connection with U.S. Appl. No. 15/821,662, dated Jan. 17, 2018.
U.S. Patent and Trademark Office, "Notice of Allowance", issued in connection with U.S. Appl. No. 15/821,662, dated Nov. 2, 2018.
Umana, P. et al., "Engineered glycoforms of an antineuro-blastoma IgG1 with optimized antibody-dependent cellular cytotoxic activity," Nature Biotechnology, vol. 17:176-180 (1999).
Vajdos, F.F., et al., "Comprehensive functional maps of the antigen-binding site of an anti-ErbB2 antibody obtained with shotgun scanning mutagenesis", Journal of Molecular Biology, 2002. vol. 320, pp. 415-428.
Van Der Heyde, H. et al., "Platelet depletion by anti-CD41 (alphaIIb) mAb injection early but not late in the course of disease protects against Plasmodium berghei pathogenesis by altering the levels of pathogenic cytokines," Blood, vol. 105(5) pp. 1956-1963 (2005).
Van Rinsum, et al., "Specific inhibition of human natural killer cell-mediated cytotoxicity by sialic acid and sialo-oligosaccharides." Int. J. Cancer, 38:915-922 (1986).
Verma, et al. "Gene therapy—promises, problems and prospects". Nature, vol. 389, 1997, pp. 239-242.
Vermes, "A novel assay for apoptosis. Flow cytometric detection of phosphatidylserine expression on early apoptotic cells using fluorescein labelled Annexin V," J. Immunol. Meth., 184:39-51 (1995).
Viswanatha, K. et al. "Engineering sialic acid synthetic ability into insect cells: identifying metabolic bottlenecks and devising strategies to overcome them," Biochemistry 42(51):15215-15225 (2003).
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Voshol, H et al., "Cell Surface Glycoconjugates as Possible Targets for Human Natural Killer Cells: Evidence Against the Involvement of Glycolipids an N-Linked Carbohydrate Chains," Gylcobiology, vol. 3, No. 1, pp. 69-76 (1993).
Wacker, C., et al., "Glycosylation profiles of therapeutic antibody pharmaceuticals," European Journal of Pharmaceutics and Biopharmaceutics, 2011, vol. 79, pp. 503-507.
Wang et al., "Identification of Trop-2 as an oncogene and an attractive therapeutic target in colon cancers," Mol. Cancer Ther. 7(2):280-285 (Feb. 2008).
Wang, Q. et al., "Second-Generation Adenovirus Vectors," Nature Medicine, vol. 2, No. 6, pp. 714-716 (1996).
Wang, Zhuozhi et al., "Humanization of a mouse monoclonal antibody neutralizing TNF-alpha by guided selection," Journal of Immunological Methods, vol. 241:171-184 (2000).
Weikert, S., et al., "Engineering Chinese hamster ovary cells to maximize sialic acid content of recombinant glycoproteins," Nature Biotechnology, vol. 17, pp. 1116-1121 (Nov. 1999).
Wells, "Heat shock proteins, tumor immunogenicity and antigen presentation: an integrated view," Immunol. Today, 21:129-132 (2000).
Wente, M., et al., "DE-310, a Macromolecular prodrug of the topoisomerase-I-inhibitor exatecan (DX-8951), in patients with operable solid tumors", Investigational New Drugs, No. 23, (2005) pp. 339-347.
Werkmeister, J. et al., "Modulation of K562 Cells with Sodium Butyrate. Association of Impaired NK Susceptibility with Sialic Acid and Analysis of Other Parameters," International Journal of Cancer, vol. 32, pp. 71-78 (1983).
Westlin, W. et al., Alleviation of myocardial stunning by leukocyte and platelet depletion, Circulation, vol. 80 (6) pp. 1828-1836 (1989).
White, et al., "Antibody-targeted immunotherapy for treatment of malignancy," Ann. Rev. Med., 52:125-145 (2001).
Wiest et al., "Expression of the Tumor-associated Mucin 1 Epitope Analyzed with the Humanized PankoMab-GEX Antibody in Malignant and Normal Tissues of the Head and Neck", Anticancer Research, 2016, vol. 36, pp. 3179-3184.
Winkler, et al., "Changing the antigen binding specificity by single point mutations of an anti-p24 (HIV-1) antibody," J Immunol 165(8):4505-4514 (2000).
Wright, Ann et al., "Antibody variable region glycosylation: position effects on antigen binding and carbohydrate structure," The EMBO Journal, vol. 10(10):2717-2723 (1991).
Written Opinion on PCT/DE2004/000132 dated Sep. 21, 2004.
Written Opinion on PCT/EP2007/007877 dated Apr. 18, 2008.
Wu, et al., "Conformation of Complementarity Determining Region L 1 Loop in Murine IgGA Light Chain Extends the Repertoire of Canonical Forms", J. Mol. Biol., vol. 229, pp. 597-601, 1993.
Wu, H. et al., "Humanization of a Murine Monoclonal Antibody by Simultaneous Optimization of Framework and CDR Residues," Journal of Molecular Biology, vol. 294, Issue 1, pp. 151-162 (1999).
Yamane-Ohnuki, N. et al., Establishment of FUT8 Knockout Chinese Hamster Ovary Cells: An Ideal Host Cell Line for Producing Completely Defucosylated Antibodies With Enhanced Antibody-Dependent Cellular Cytotoxicity, biotechnology and Bioengineering, vol. 87(5), pp. 614-622 (2004).
Yang, Xiao-Dong et al., "Development of ABX-EGF, a fully human anti-EGF receptor monoclonal antibody, for cancer therapy," Critical Reviews in Oncology/Hermatology, vol. 38:17-23 (2001).
Yano et al., "Comparison of HER2 gene amplification assessed by fluorescence in situ hybridization and HER2 protein expression assessed by immunohistochemistry in gastric cancer," Oncol. Rep. 15:65-71 (2006).
Yonesaka, K., "Anti-HER3 Antibody Patritumab Overcoes Resistance to EGFR Inhibitor in Non-small Cell Lung Cancer", The Japan Lung Cancer Society, vol. 55, pp. 948-955, 2015 (8 pages).
Yonesaka, K., et al., "Anti-HER3 monoclonal antibody patritumab sensitizes refractory non-small cell lung cancer to the epidermal growth factor receptor inhibitor erlotinib", Oncogene vol. 35, pp. 878-886, 2016 (10 pages).
Yoshima et al., "Heat Shock Factor 1 Mediates Hemin-induced hsp70 Gene Transcription in K562 Erythroleukemia Cells," J Biol. Chem. 273(39):25466-25471 (1998).
Yoshimura, M et al., "Bisecting N-Acetylglucosamine on K562 Cells Suppresses Natural Killer Cytotoxicity and Promotes Spleen Colonization," Cancer Res., vol. 56:412-418 (1996).
Yu, J-Y. et al., "RNA Interference by Expression of Short-Interfering RNAs and Hairpin RNAs in Mammalian Cells," Proceedings of the National Academy of Sciences, vol. 99, No. 9, pp. 6047-6052 (2002).
Zarbock, A. et al., "Complete reversal of acid-induced acute lung injury by blocking of platelet-neutrophil aggregation," The Journal of Clinical Investigation, vol. 116 (12), pp. 3211-3219 (2006).
Zhang, et al., "Stable expression of human alpha-2,6-sialyltransferase in Chinese hamster ovary cells: functional consequences for human erythropoietin expression and bioactivity," Biochimica et Biophysica Acta, 1998, vol. 1425, pp. 441-452.
Zhang, S. et al., "Selection of Tumor Antigens as Targets for Immune Attack Using Immunochemistry: II. Blood Grou-Related Antigens," International Journal of Cancer, vol. 73, pp. 50-56 (1997).
Zhu et al., "Novel human interleukin-15 agonists," The Journal of Immunology (183):3598-3607 (2009).
A. Parslow et al., "Antibody-Drug Conjugates for Cancer Therapy," Biomedicines, 4, 14, 2016 (17 pages).
B. Kong et al., "Experimental study of single-chain antibody-directed ovarian epithelial cancer for targeted gene transfer," Progress in Modern Obstetrics and Gynecology, Dec. 31, 2000, pp. 324-327.

(56) References Cited

OTHER PUBLICATIONS

G. Rivalland, B. Loveland, P. Mitchell, "Update on Mucin-1 immunotherapy in cancer: a clinical perspective," Expert Opinion in Biological Therapy, 15:12, 2015, pp. 1773-1787.
H. Vezina et al., "Antibody-Drug Conjugates as Cancer Therapeutics: Past, Present, and Future," Journal of Clinical Pharmacology, vol. 57, No. S10, Supplemental Article, Oct. 2017, pp. S11-S24.
J. Taylor-Papadimitriou et al., "MUC1 and cancer," Biochimica et Biophysica Acta 1455, 1999, pp. 301-313.
Office Action and Search Report issued in corresponding Chinese Patent Application 201980033159.4, dated Aug. 4, 2023.
Y. Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, 2016, pp. 1039-1046.
Decision to Grant issued in connection with Russian Appl. No. 2020141767 dated Aug. 1, 2023.
Final Rejection issued in connection with JP Appl. Ser. No. 2020-564569 dated Sep. 4, 2022.
Office Action and Search Report dated Dec. 22, 2021 issued in corresponding Russian Patent Application No. 2020141760 (15 pages, English translation included).
Danielczyk et al., "PankoMab: a potent new generation anti-tumour MUC1 antibody," Cancer Immunology, Immunotherapy, vol. 55, 2006, pp. 1337-1347.
Wright et al., "Antibody variable region glycosylation: Position effects on antigen binding and carbohydrate structure," The EMBO Journal, vol. 10, No. 10, 1991, pp. 2717-2723.
International Searching Authority, "International Search Report," issued in connection with International Patent Application No. PCT/EP2019/062756, dated Jul. 2, 2019.
International Searching Authority, "Written Opinion," issued in connection with International Patent Application No. PCT/EP2019/062756, dated Jul. 2, 2019.
Ibrahim et al., "Randomized Phase II Trial of Letrozole plus Anti-MUC1 Antibody AS1402 in Hormone Receptor-Positive Locally Advanced or Metastatic Breast Cancer," Clinical Cancer Research, vol. 17, No. 21, Nov. 1, 2011, pp. 6822-6830.
Thie et al., "Rise and Fall of an Anti-MUC1 Specific Antibody," PLoS One, vol. 6, Issue 1, Jan. 2011, e15921, 19 pages.
Harris, Reed J., "Processing of C-terminal lysine and arginine residues of proteins isolated from mammalian cell culture," Journal of Chromatography A, vol. 705, Issue 1, Jun. 23, 1995, pp. 129-134.
Johnson et al., "Cation exchange-HPLC and mass spectrometry reveal C-terminal amidation of an IgG1 heavy chain," Analytical Biochemistry, vol. 360, Issue 1, Jan. 1, 2007, pp. 75-83.
Lu J. et al.: "Linkers Having a Crucial Role in Antibody-Drug Conjugates", Int. J. Mol. Sci., 2016, v. 17 (4): 561.
Office Action issued in related Columbian Patent Application No. NC2020/0014435, dated Jan. 27, 2023.
Office Action and Search Report issued in related Russian Patent Application No. 2020141767 dated Oct. 7, 2022.
Office Action issued in corresponding Colombian Patent Application No. NC2023/0006574 dated Jun. 23, 2023 (23 pages).
Edwards et al., "The Remarkable Flexibility of the Human Antibody Repertoire; Isolation of Over One Thousand Different Antibodies to a Single Protein, BLyS", Journal of Molecular Biology, 2003, pp. 103-118.
Extended European Search Report issued in connection with EP Appl. No. 23174276.8 dated Oct. 23, 2023.
Goel et al., "Plasticity within the Antigen-Combining Site May Manifest as Molecular Mimicry in the Humoral Immune Response", The Journal of Immunology Dec. 15, 2004; 173(12), pp. 7358-7367.
Janeway et al., "Immunobiology The Immune System In Health and Disease", 3rd edition, Garland Publishing Inc., 1997, pp. 3:1-3:11.
Kanyavuz et al., "Breaking the law: unconventional strategies for antibody diversification", Nature Reviews Immunology, Jun. 2019, vol. 19, pp. 355-368.
Lescar et al., "Crystal Structure of a Cross-reaction Complex between Fab F9.13. 7 and Guinea Fowl Lysozyme", The Journal of Biological Chemistry, vol. 270, No. 30. Issued of Jul. 30, 1995, pp. 18067-18076.
Lloyd et al., "Modelling the human immune response: performance of a 10" human antibody repertoire against a broad panel of therapeutically relevant antigens", Protein Engineering, Design & Selection, vol. 22 No. 3, 2009, pp. 159-168.
Stryer, L., Biochemistry, 4th edition, W. H. Freeman and Company, 1995, pp. 18-23.
Office Action issued in corresponding Colombian Patent Application No. NC2023/0006574 dated Feb. 9, 2024 (23 pages).
Berraondo et al., "Cytokines in clinical cancer immunotherapy", Br J Cancer., Nov. 9, 2018, vol. 120, pp. 6-15.
Office Action issued in corresponding Philippines Patent Application No. 1/2020/551969 dated Sep. 24, 2024 (7 pages).
Hamblett et al., "Effects of Drug Loading on the Antitumor Activity of a Monoclonal Antibody Drug Conjugate", Clinical Cancer Research, vol. 10, No. 20, Oct. 15, 2004, pp. 7063-7070.
Jefferis, Roy, "Glycosylation as a strategy to improve antibody-based therapeutics", Nat Rev Drug Discov., vol. 8, No. 3, Mar. 2009, pp. 226-234.
Mirsky et al., "Antibody-Specific Model of Amino Acid Substitution for Immunological Inferences from Alignments of Antibody Sequences", Mol. Biol. Evol., Dec. 21, 2014, vol. 32, No. 3, pp. 806-819.
Office Action issued in corresponding Philippines Patent Application No. 1/2020/551970 dated Jul. 4, 2024 (7 pages).

* cited by examiner

Figure 1 - continued
B
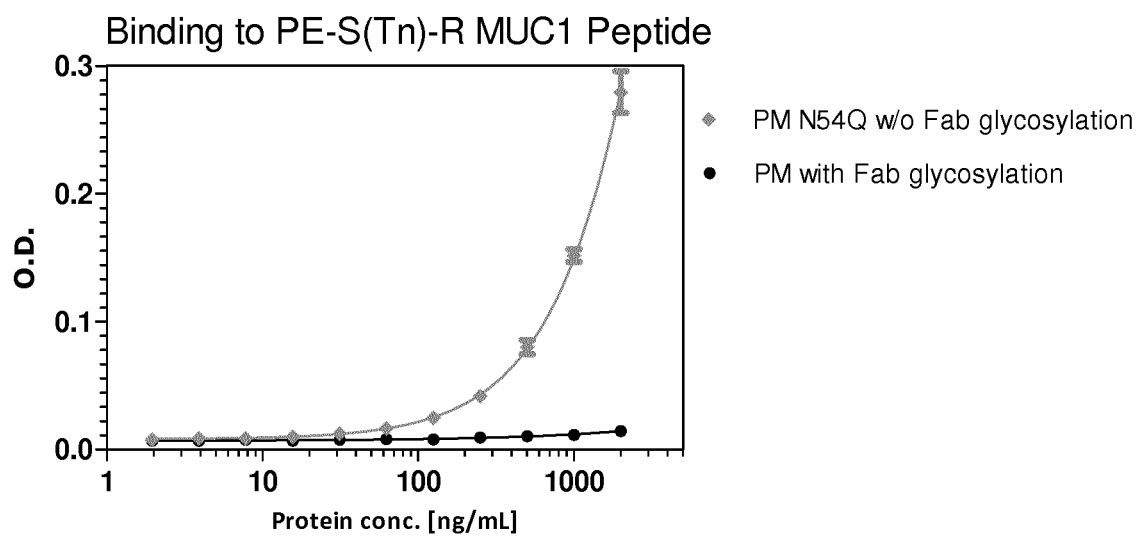
C
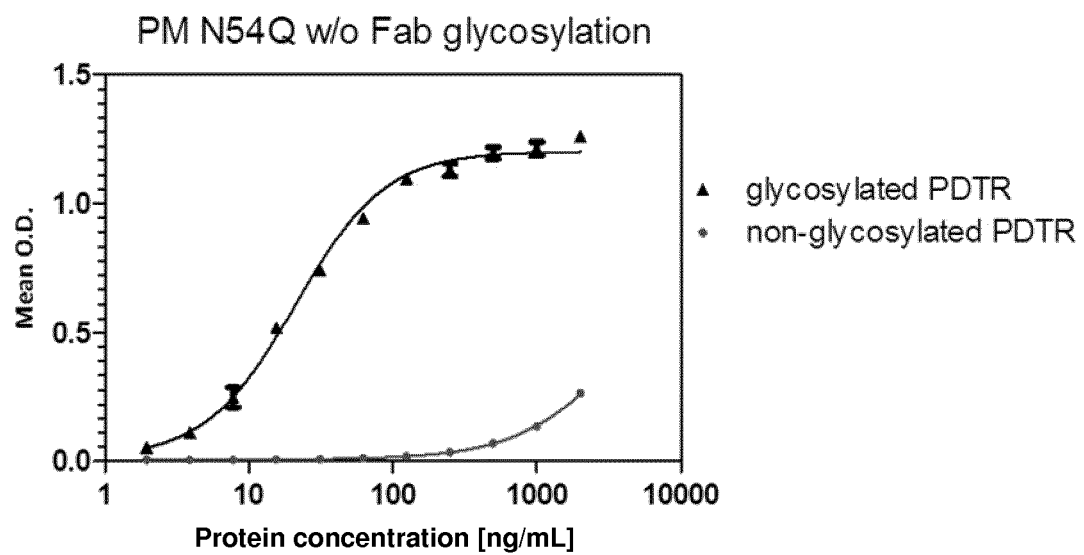

Figure 1 - continued
D
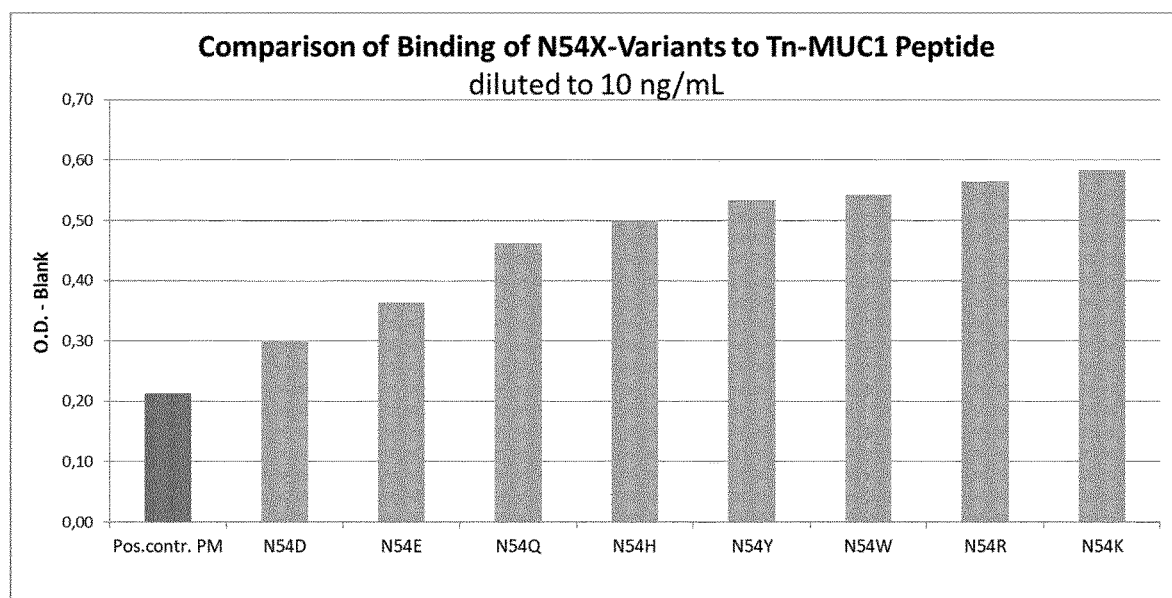

Figure 1 - continued
E
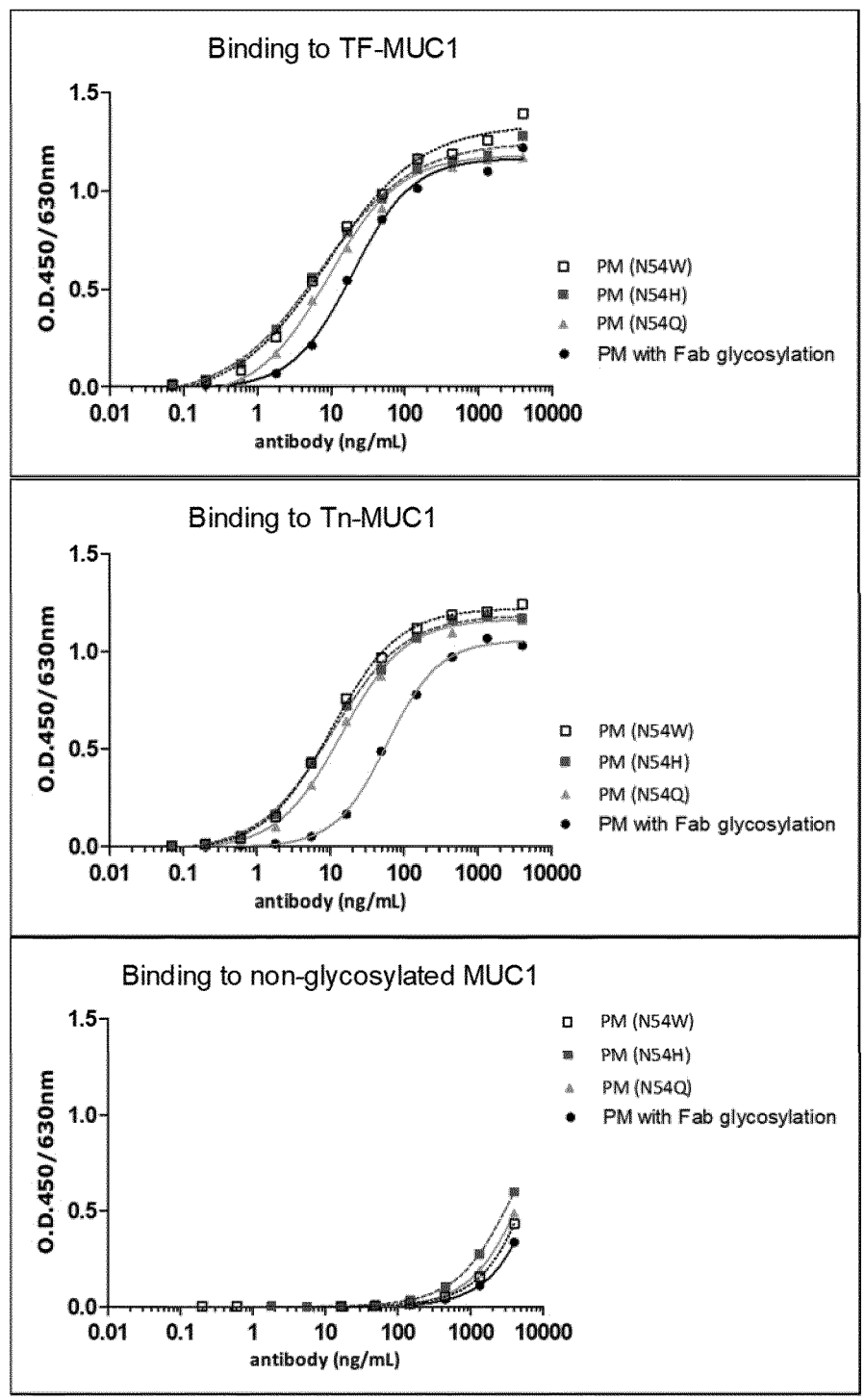

Figure 1 - continued
F
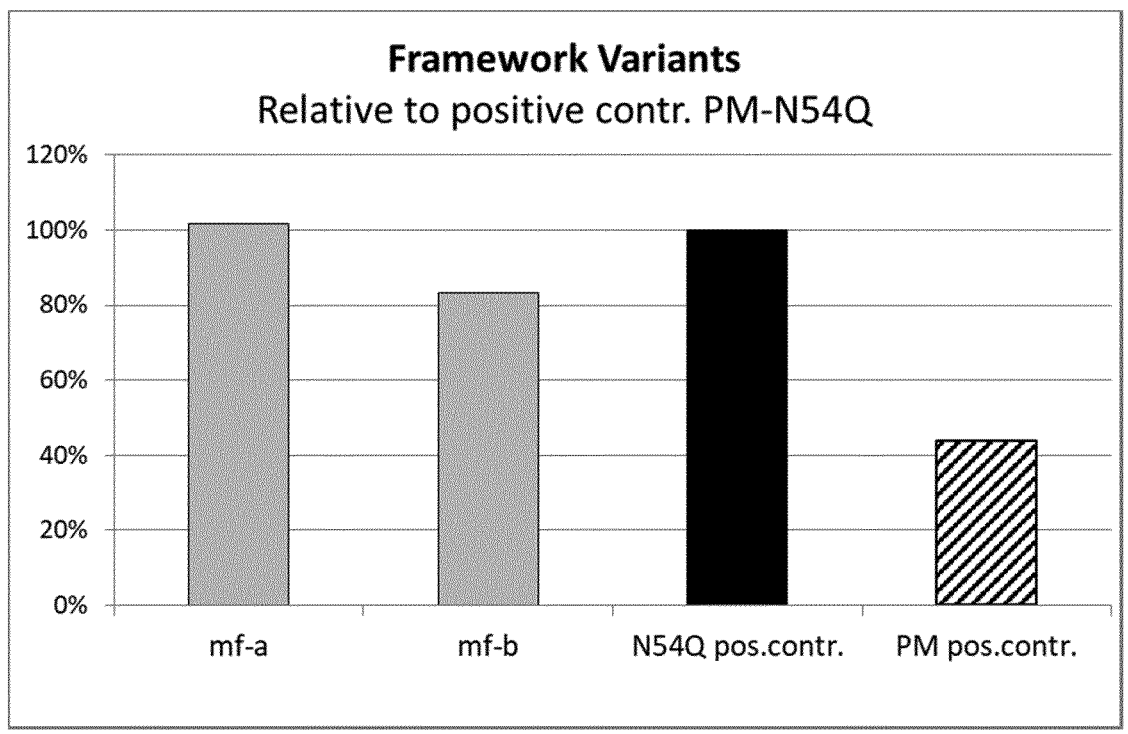
Figure 2
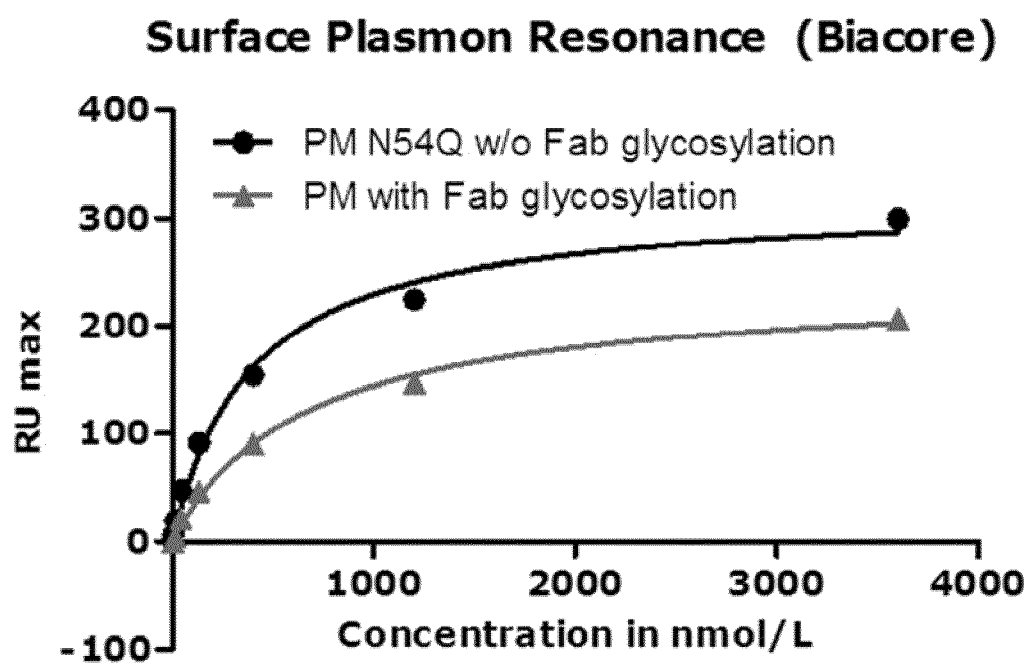

The amino acid sequence of the heavy chain of the humanized antibody N54Q (SEQ ID No: 22)

```
EVQLVESGGGLVQPGGSMRLSCVASGFPFSNYWMNWVRQAPGKGLEWVGEIRLKSNQYTTHY
AESVKGRFTISRDDSKNSLYLQMNSLKTEDTAVYYCTRHYYFDYWGQGTLVTVSSASTKGPS
VFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEGLHN
HYTQKSLSLSPGK
``` variable region: aa 1-117, constant region: aa 118-447

Figure 9

The amino acid sequence of the light chain of the humanized antibodies N54Q and PankoMab (SEQ ID No: 16)

```
DIVMTQSPLSNPVTPGEPASISCRSSKSLLHSNGITYFFWYLQKPGQSPQLLIYQMSNLASG
VPDRFSGSGSGTDFTLRISRVEAEDVGVYYCAQNLELPPTFGQGTKVEIKRTVAAPSVFIFP
PSDEQLKSGTASVVCLLNNFYPREAKVQWKVDNALQSGNSQESVTEQDSKDSTYSLSSTLTL
SKADYEKHKVYACEVTHQGLSSPVTKSFNRGEC
``` variable region: aa 1-113, constant region: aa 114-219

Figure 10

The amino acid sequence of the heavy chain of the humanized antibody PankoMab (SEQ ID No: 19)

```
EVQLVESGGGLVQPGGSMRLSCVASGFPFSNYWMNWVRQAPGKGLEWVGEIRLKSNNYTTHY
AESVKGRFTISRDDSKNSLYLQMNSLKTEDTAVYYCTRHYYFDYWGQGTLVTVSSASTKGPS
VFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEGLHN
HYTQKSLSLSPGK
```

Figure 11

The amino acid sequence of the heavy chain of chimeric antibody PM N54Q (SEQ ID No: 23)

```
MKHLWFFLLLVAAPRWVLSEVQLVESGGGLVQPGGSMRLSCVASGFPFSNYWMNWVRQAPGK
GLEWVGEIRLKSNQYTTHYAESVKGRFTISRDDSKNSLYLQMNSLKTEDTAVYYCTRHYYFD
YWGQGTLVTVSSAKTTPPSVYPLAPGSAAQTNSMVTLGCLVKGYFPEPVTVTWNSGSLSSGV
HTFPAVLQSDLYTLSSSVTVPSSTWPSQTVTCNVAHPASSTKVDKKIVPRDCGCKPCICTVP
EVSSVFIFPPKPKDVLTITLTPKVTCVVVDISKDDPEVQFSWFVDDVEVHTAQTKPREEQIN
STFRSVSELPIMHQDWLNGKEFKCRVNSAAFPAPIEKTISKTKGRPKAPQVYTIPPPKEQMA
KDKVSLTCMITNFFPEDITVEWQWNGQPAENYKNTQPIMDTDGSYFVYSKLNVQKSNWEAGN
TFTCSVLHEGLHNHHTEKSLSHSPGK
``` secretory signal sequence: aa 1-19, variable region: aa 20-136, constant region: aa 137-460

Figure 12

The amino acid sequence of the light chain of chimeric antibody PM N54Q (SEQ ID No: 21)

```
MVLQTQVFISLLLWISGAYGDIVMTQSPLSNPVTPGEPASISCRSSKSLLHSNGITYFFWYL
QKPGQSPQLLIYQMSNLASGVPDRFSGSGSGTDFTLRISRVEAEDVGVYYCAQNLELPPTFG
QGTKVEIKRADAAPTVSIFPPSSEQLTSGGASVVCFLNNFYPKDINVKWKIDGSERQNGVLN
SWTDQDSKDSTYSMSSTLTLTKDEYERHNSYTCEATHKTSTSPIVKSFNRNEC
``` secretory signal sequence: aa 1-20, variable region: aa 21-133, constant region: aa 134-239

ANTI-MUC1 ANTIBODY

CROSS-REFERENCE TO RELATED APPLICATIONS

The present application claims priority under 37 U.S.C. § 371 to International Patent Application No. PCT/EP2019/062756, filed May 17, 2019, which claims priority to and the benefit of European Patent Application No. 18173253.8, filed on May 18, 2018. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on May 18, 2018, is named 127273-0102_SL.txt and is 34 kb in size.

FIELD OF THE INVENTION

The present invention pertains to the field of antibodies. A mutated anti-MUC1 antibody with increased antigen binding affinity is provided. In particular, a mutated version of the humanized antibody PankoMab is provided wherein asparagine 57 of the heavy chain variable region is substituted by another amino acid. Thereby, the glycosylation site in the CDR2 region is deleted and the antigen binding affinity is increased. In specific embodiments, the present invention is directed to the therapeutic and diagnostic use of this antibody and to methods of producing such antibodies.

BACKGROUND OF THE INVENTION

Antibodies against tumor-associated antigens are widely used therapeutics against cancers. Today, many anti-cancer antibodies are approved for human therapy. Some of these antibodies act by blocking certain signaling pathways which are critical for survival or proliferation of specific cancer cells. Other anti-cancer antibodies activate the patient's immune response against the targeted cancer cells, for example by initiating antibody-dependent cellular cytotoxicity (ADCC) via natural killer cells. This mechanism is induced by binding of the antibody's Fc part to Fc receptors on the immune cells.

An interesting and important group of antibodies are those directed against mucin proteins. Mucins are a family of high molecular weight, heavily glycosylated proteins produced by many epithelial tissues in vertebrates. They can be subdivided into mucin proteins which are membrane-bound due to the presence of a hydrophobic membrane-spanning domain that favors retention in the plasma membrane, and mucins which are secreted onto mucosal surfaces or secreted to become a component of saliva. The human mucin protein family consists of many family members, including membrane bound MUC1.

Increased mucin production occurs in many adenocarcinomas, including cancer of the pancreas, lung, breast, ovary, colon, etc. Mucins are also overexpressed in lung diseases such as asthma, bronchitis, chronic obstructive pulmonary disease or cystic fibrosis. Two membrane mucins, MUC1 and MUC4 have been extensively studied in relation to their pathological implication in the disease process. Moreover, mucins are also being investigated for their potential as diagnostic markers. Several antibodies directed against mucin proteins (Clin. Cancer Res., 2011 Nov. 1; 17(21): 6822-30, PLoS One, 2011 Jan. 14; 6(1):e15921), in particular MUC1, are known in the art. However, their therapeutic efficacy could still be improved.

In view of this, there is a need in the art to provide therapeutic anti-MUC1 antibodies with improved properties.

SUMMARY OF THE INVENTION

The present inventors have found that deleting the glycosylation site in the heavy chain variable region of the anti-MUC1 antibody PankoMab did not abolish antigen binding, but rather unexpectedly increased the antigen affinity of the antibody. This was in particular surprising as the glycosylation site is located in the second complementarity-determining region of the heavy chain variable region (CDR-H2). The CDRs are those regions of an antibody which are directly involved in antigen binding and provide the contact to the epitope. Therefore, generally modifying the amino acids of a CDR is expected to be detrimental to the antigen binding affinity. The humanized PankoMab antibody additionally comprises a glycosylation site in CDR-H2, which carries a large carbohydrate structure. This carbohydrate structure is present directly at the binding interface to the antigen and hence, was considered to be involved in antigen binding. However, as demonstrated in the examples, the PankoMab variant (N54Q) wherein the glycosylation site is deleted by substituting the amino acid carrying the carbohydrate structure exhibits an increased antigen binding affinity.

Therefore, in a first aspect, the present invention is directed to an antibody capable of binding to MUC1, which comprises
  (i) a heavy chain variable region comprising the complementarity-determining regions (CDRs) CDR-H1 having the amino acid sequence of SEQ ID NO: 1, CDR-H2 having the amino acid sequence of SEQ ID NO: 2 and CDR-H3 having the amino acid sequence of SEQ ID NO: 3, and
  (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

In a second aspect, the present invention provides a nucleic acid encoding the antibody according to the invention. Furthermore, in a third aspect an expression cassette or vector comprising the nucleic acid according to the invention and a promoter operatively connected with said nucleic acid and, in a fourth aspect, a host cell comprising the nucleic acid or the expression cassette or vector according to the invention are provided.

In a fifth aspect, the present invention provides a conjugate comprising the antibody according to the invention conjugated to a further agent.

In a sixth aspect, the present invention is directed to a composition comprising the antibody according to the invention, the nucleic acid according to the invention, the expression cassette or vector according to the invention, the host cell according to the invention, or the conjugate according to the invention.

According to a seventh aspect, the invention provides the antibody, the nucleic acid, the expression cassette or vector, the host cell, the composition or the conjugate according to the invention for use in medicine, in particular in the treatment, prevention or diagnosis of cancer.

In an eighth aspect, the invention provides a method of increasing the MUC1 binding affinity of an antibody comprising
  (i) a heavy chain variable region comprising the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
  (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6,
the method comprising the step of substituting the amino acid residue at position 8 of CDR-H2 with any amino acid residue except asparagine, resulting in CDR-H2 having the amino acid sequence of SEQ ID NO: 2.

In a ninth aspect, the invention provides a method of producing an antibody with increased MUC1 binding affinity, comprising
  (a) providing a nucleic acid coding for an antibody which comprises
    (i) a heavy chain variable region comprising the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
    (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
  (b) introducing a mutation into said nucleic acid to produce a mutated nucleic acid, wherein the mutation is introduced in the codon coding for the amino acid residue at position 8 of CDR-H2 so that said codon codes for any amino acid residue except asparagine; and
  (c) producing the antibody with increased MUC1 binding affinity by expressing the mutated nucleic acid in a host cell.

In a tenth aspect, the present invention provides a method for treating cancer in a subject in need thereof comprising, administering to the subject with cancer a therapeutically effective amount of the antibody according to the invention, the nucleic acid according to the invention, the expression cassette or vector according to the invention, or the host cell according to the invention.

In a eleventh aspect, the present invention provides kits or devices comprising the antibody according to the invention, and associated methods that are useful in the diagnosis, detecting or monitoring of MUC1 associated disorders such as cancer.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

Definitions

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of". The term "consist essentially of", where possible, in particular refers to embodiments wherein the subject-matter comprises 20% or less, in particular 15% or less, 10% or less or especially 5% or less further elements in addition to the specifically listed elements of which the subject-matter consists essentially of.

The term "antibody" in particular refers to a protein comprising at least two heavy chains and two light chains connected by disulfide bonds. Each heavy chain is comprised of a heavy chain variable region ($V_H$) and a heavy chain constant region ($C_H$). Each light chain is comprised of a light chain variable region ($V_L$) and a light chain constant region ($C_L$). The heavy chain-constant region comprises three or—in the case of antibodies of the IgM- or IgE-type—four heavy chain-constant domains ($C_{H1}$, $C_{H2}$, $C_{H3}$ and $C_{H4}$) wherein the first constant domain $C_{H1}$ is adjacent to the variable region and may be connected to the second constant domain $C_{H2}$ by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The heavy chain constant regions may be of any type such as γ-, δ-, α-, μ- or ε-type heavy chains. Preferably, the heavy chain of the antibody is a γ-chain. Furthermore, the light chain constant region may also be of any type such as κ- or λ-type light chains. Preferably, the light chain of the antibody is a κ-chain. The terms "γ- (δ-, α-, μ- or ε-) type heavy chain" and "κ- (λ-) type light chain" refer to antibody heavy chains or antibody light chains, respectively, which have constant region amino acid sequences derived from naturally occurring heavy or light chain constant region amino acid sequences, especially human heavy or light chain constant region amino acid sequences. In particular, the amino acid sequence of the constant domains of a γ-type (especially γ1-type) heavy chain is at least 95%, especially at least 98%, identical to the amino acid sequence of the constant domains of a human γ (especially the human γ1) antibody heavy chain. Furthermore, the amino acid sequence of the constant domain of a κ-type light chain is in particular at least 95%, especially at least 98%, identical to the amino acid sequence of the constant domain of the human κ antibody light chain. The constant regions of the antibodies may mediate the binding of the immunoglobulin to host tissues or factors, including various cells of the immune system (e.g., effector cells) and the first component (C1q) of the classical complement system. The antibody can be e.g. a humanized, human or chimeric antibody.

The antigen-binding portion of an antibody usually refers to full length or one or more fragments of an antibody that retains the ability to specifically bind to an antigen. It has been shown that the antigen-binding function of an antibody can be performed by fragments of a full-length antibody. Examples of binding fragments of an antibody include a Fab fragment, a monovalent fragment consisting of the $V_L$, $V_H$, $C_L$ and $C_{H1}$ domains; a F(ab)$_2$ fragment, a bivalent fragment comprising two Fab fragments, each of which binds to the same antigen, linked by a disulfide bridge at the hinge region; a Fd fragment consisting of the $V_H$ and $C_{H1}$ domains; a Fv fragment consisting of the $V_L$ and $V_H$ domains of a single arm of an antibody; and a dAb fragment, which consists of a $V_H$ domain.

The "Fab part" of an antibody in particular refers to a part of the antibody comprising the heavy and light chain variable regions ($V_H$ and $V_L$) and the first domains of the heavy and light chain constant regions ($C_{H1}$ and $C_L$). In cases where the antibody does not comprise all of these regions, then the term "Fab part" only refers to those of the regions $V_H$, $V_L$, $C_{H1}$ and $C_L$ which are present in the antibody. Preferably, "Fab part" refers to that part of an antibody corresponding to the fragment obtained by digesting a natural antibody with papain which contains the antigen binding activity of the antibody. In particular, the Fab part of an antibody encompasses the antigen binding site or antigen binding ability thereof. Preferably, the Fab part comprises at least the $V_H$ region of the antibody.

The "Fc part" of an antibody in particular refers to a part of the antibody comprising the heavy chain constant regions 2, 3 and—where applicable—4 ($C_{H2}$, $C_{H3}$ and $C_{H4}$). In particular, the Fc part comprises two of each of these regions. In cases where the antibody does not comprise all of these regions, then the term "Fc part" only refers to those of the regions $C_{H2}$, $C_{H3}$ and $C_{H4}$ which are present in the antibody. Preferably, the Fc part comprises at least the $C_{H2}$ region of the antibody. Preferably, "Fc part" refers to that part of an antibody corresponding to the fragment obtained by digesting a natural antibody with papain which does not contain the antigen binding activity of the antibody. In particular, the Fc part of an antibody is capable of binding to the Fc receptor and thus, e.g. comprises an Fc receptor binding site or an Fc receptor binding ability.

The terms "antibody" and "antibody construct", as used herein, refer in certain embodiments to a population of antibodies or antibody constructs, respectively, of the same kind. In particular, all antibodies or antibody constructs of the population exhibit the features used for defining the antibody or antibody construct. In certain embodiments, all antibodies or antibody constructs in the population have the same amino acid sequence. Reference to a specific kind of antibody, such as an antibody capable of specifically binding to MUC1, in particular refers to a population of this kind of antibody.

The term "antibody" as used herein also includes fragments and derivatives of said antibody. A "fragment or derivative" of an antibody in particular is a protein or glycoprotein which is derived from said antibody and is capable of binding to the same antigen, in particular to the same epitope as the antibody. Thus, a fragment or derivative of an antibody herein generally refers to a functional fragment or derivative. In particularly preferred embodiments, the fragment or derivative of an antibody comprises a heavy chain variable region. It has been shown that the antigen-binding function of an antibody can be performed by fragments of a full-length antibody or derivatives thereof. Examples of fragments of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. Derivatives of an antibody in particular include antibodies which bind to or compete with the same antigen as the parent antibody, but which have a different amino acid sequence than the parent antibody from which it is derived. These antibody fragments and derivatives are obtained using conventional techniques known to those with skill in the art.

A target amino acid sequence is "derived" from or "corresponds" to a reference amino acid sequence if the target amino acid sequence shares a homology or identity over its entire length with a corresponding part of the reference amino acid sequence of at least 75%, more preferably at least 80%, at least 85%, at least 90%, at least 93%, at least 95%, at least 97%, at least 98% or at least 99%. The "corresponding part" means that, for example, framework region 1 of a heavy chain variable region (FRH1) of a target antibody corresponds to framework region 1 of the heavy chain variable region of the reference antibody. In particular embodiments, a target amino acid sequence which is "derived" from or "corresponds" to a reference amino acid sequence is 100% homologous, or in particular 100% identical, over its entire length with a corresponding part of the reference amino acid sequence. A "homology" or "identity" of an amino acid sequence or nucleotide sequence is preferably determined according to the invention over the entire length of the reference sequence or over the entire length of the corresponding part of the reference sequence which corresponds to the sequence which homology or identity is defined. An antibody derived from a parent antibody which is defined by one or more amino acid sequences, such as specific CDR sequences or specific variable region sequences, in particular is an antibody having amino acid sequences, such as CDR sequences or variable region sequences, which are at least 75%, preferably at least 80%, at least 85%, at least 90%, at least 93%, at least 95%, at least 97%, at least 98% or at least 99% homologous or identical, especially identical, to the respective amino acid sequences of the parent antibody. In certain embodiments, the antibody derived from (i.e. derivative of) a parent antibody comprises the same CDR sequences as the parent antibody, but differs in the remaining sequences of the variable regions.

The term "antibody" as used herein also refers to multivalent and multispecific antibodies, i.e. antibody constructs which have more than two binding sites each binding to the same epitope and antibody constructs which have one or more binding sites binding to a first epitope and one or more binding sites binding to a second epitope, and optionally even further binding sites binding to further epitopes.

"Specific binding" preferably means that an agent such as an antibody binds stronger to a target such as an epitope for which it is specific compared to the binding to another target. An agent binds stronger to a first target compared to a second target if it binds to the first target with a dissociation constant ($K_d$) which is lower than the dissociation constant for the second target. Preferably the dissociation constant for the target to which the agent binds specifically is more than 100-fold, 200-fold, 500-fold or more than 1000-fold lower than the dissociation constant for the target to which the agent does not bind specifically. Furthermore, the term "specific binding" in particular indicates a binding affinity between the binding partners with an affinity constant $K_a$ of at least $10^6 \, M^{-1}$, preferably at least $10^7 \, M^{-1}$, more preferably at least $10^8 \, M^{-1}$. An antibody specific for a certain antigen in particular refers to an antibody which is capable of binding to said antigen with an affinity having a $K_a$ of at least $10^6 \, M^{-1}$, preferably at least $10^7 \, M^{-1}$, more preferably at least $10^8 \, M^{-1}$. For example, the term "anti-MUC1 antibody" in particular refers to an antibody specifically binding MUC1 and preferably is capable of binding to MUC1 with an affinity having a $K_a$ of at least $10^6 \, M^{-1}$, preferably at least $10^7 \, M^{-1}$, more preferably at least $10^8 \, M^{-1}$.

The term "MUC1" refers to the protein MUC1, also known as mucin-1, polymorphic epithelial mucin (PEM) or cancer antigen 15-3, in particular to human MUC1 (Accession No. P15941). MUC1 is a member of the mucin family and encodes a membrane bound, glycosylated phosphoprotein. MUC1 has a core protein mass of 120-225 kDa which increases to 250-500 kDa with glycosylation. It extends 200-500 nm beyond the surface of the cell. The protein is anchored to the apical surface of many epithelial cells by a transmembrane domain. The extracellular domain includes a 20 amino acid variable number tandem repeat (VNTR) domain, with the number of repeats varying from 20 to 120 in different individuals. These repeats are rich in serine, threonine and proline residues which permits heavy O-glycosylation. In certain embodiments, the term "MUC1" refers to tumor-associated MUC1 ("TA-MUC1"). TA-MUC1 is MUC1 present on cancer cells. This MUC1 differs from MUC1 present on non-cancer cells MUC1 has a much higher expression level, its localization and its glycosylation. In particular, TA-MUC1 is present apolarly over the whole cell surface in cancer cells, while in non-cancer cells MUC1 has a strictly apical expression and hence, is not accessible for systemically administered antibodies. Furthermore, TA-MUC1 has an aberrant O-glycosylation which exposes new peptide epitopes on the MUC1 protein backbone and new carbohydrate tumor antigens such as the Thomsen-Friedenreich antigen alpha (TFα).

"TFα", also called Thomsen-Friedenreich antigen alpha or Core-1, refers to the disaccharide Gal-ß1,3-GalNAc which is O-glycosidically linked in an alpha-anomeric configuration to the hydroxy amino acids serine or threonine of proteins in carcinoma cells.

The term "sialic acid" in particular refers to any N- or O-substituted derivatives of neuraminic acid. It may refer to both 5-N-acetylneuraminic acid and 5-N-glycolylneuraminic acid, but preferably only refers to 5-N-acetylneuraminic acid. The sialic acid, in particular the 5-N-acetylneuraminic acid preferably is attached to a carbohydrate chain via a 2,3- or 2,6-linkage. Preferably, in the antibodies described herein both 2,3- as well as 2,6-coupled sialic acids are present.

A "relative amount of glycans" according to the invention refers to a specific percentage or percentage range of the glycans attached to the antibodies of an antibody preparation or in a composition comprising antibodies, respectively. In particular, the relative amount of glycans refers to a specific percentage or percentage range of all glycans comprised in the antibodies and thus, attached to the polypeptide chains of the antibodies in an antibody preparation or in a composition comprising antibodies. 100% of the glycans refers to all glycans attached to the antibodies of the antibody preparation or in a composition comprising antibodies, respectively. For example, a relative amount of glycans carrying bisecting GlcNAc of 10% refers to a composition comprising antibodies wherein 10% of all glycans comprised in the antibodies and thus, attached to the antibody polypeptide chains in said composition comprise a bisecting GlcNAc residue while 90% of all glycans comprised in the antibodies and thus, attached to the antibody polypeptide chains in said composition do not comprise a bisecting GlcNAc residue. The corresponding reference amount of glycans representing 100% may either be all glycan structures attached to the antibodies in the composition, or all N-glycans, i.e. all glycan structures attached to an asparagine residue of the antibodies in the composition, or all complex-type glycans. The reference group of glycan structures generally is explicitly indicated or directly derivable from the circumstances by the skilled person.

The term "N-glycosylation" refers to all glycans attached to asparagine residues of the polypeptide chain of a protein. These asparagine residues generally are part of N-glycosylation sites having the amino acid sequence Asn-Xaa-Ser/Thr, wherein Xaa may be any amino acid except for proline. Likewise, "N-glycans" are glycans attached to asparagine residues of a polypeptide chain. The terms "glycan", "glycan structure", "carbohydrate", "carbohydrate chain" and "carbohydrate structure" are generally used synonymously herein. N-glycans generally have a common core structure consisting of two N-acetylglucosamine (GlcNAc) residues and three mannose residues, having the structure Manα1,6-(Manα1,3-)Manβ1,4-GlcNAcβ1,4-GlcNAcβ1-Asn with Asn being the asparagine residue of the polypeptide chain. N-glycans are subdivided into three different types, namely complex-type glycans, hybrid-type glycans and high mannose-type glycans.

The numbers given herein, in particular the relative amounts of a specific glycosylation property, are preferably to be understood as approximate numbers. In particular, the numbers preferably may be up to 10% higher and/or lower, in particular up to 9%, 8%, 7%, 6%, 5%, 4%, 3%, 2% or 1% higher and/or lower.

In a "conjugate" two or more compounds are linked together. In certain embodiments, at least some of the properties from each compound are retained in the conjugate. Linking may be achieved by a covalent or non-covalent bond. Preferably, the compounds of the conjugate are linked via a covalent bond. The different compounds of a conjugate may be directly bound to each other via one or more covalent bonds between atoms of the compounds. Alternatively, the compounds may be bound to each other via a chemical moiety such as a linker molecule wherein the linker is covalently attached to atoms of the compounds. If the conjugate is composed of more than two compounds, then these compounds may, for example, be linked in a chain conformation, one compound attached to the next compound, or several compounds each may be attached to one central compound.

The term "nucleic acid" includes single-stranded and double-stranded nucleic acids and ribonucleic acids as well as deoxyribonucleic acids. It may comprise naturally occurring as well as synthetic nucleotides and can be naturally or synthetically modified, for example by methylation, 5'- and/or 3'-capping.

The term "expression cassette" in particular refers to a nucleic acid construct which is capable of enabling and regulating the expression of a coding nucleic acid sequence introduced therein. An expression cassette may comprise promoters, ribosome binding sites, enhancers and other control elements which regulate transcription of a gene or translation of an mRNA. The exact structure of expression cassette may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the operatively connected nucleic acid. Expression cassettes may also comprise enhancer sequences or upstream activator sequences.

According to the invention, the term "promoter" refers to a nucleic acid sequence which is located upstream (5') of the nucleic acid sequence which is to be expressed and controls expression of the sequence by providing a recognition and binding site for RNA-polymerases. The "promoter" may include further recognition and binding sites for further factors which are involved in the regulation of transcription of a gene. A promoter may control the transcription of a prokaryotic or eukaryotic gene. Furthermore, a promoter may be "inducible", i.e. initiate transcription in response to an inducing agent, or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and comprise primary cells and cell lines. A nucleic acid may be present in the host cell in the form of a single copy or of two or more copies and, in one embodiment, is expressed in the host cell.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The term "cancer" according to the invention in particular comprises leukemias, seminomas, melanomas, carcinomas, teratomas, lymphomas, sarcomas, mesotheliomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, bladder cancer, cancer of the uterus, ovarian cancer and lung cancer and the metastases thereof. The term cancer according to the invention also comprises cancer metastases.

By "tumor" is meant a group of cells or tissue that is formed by misregulated cellular proliferation. Tumors may show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and normally involves detachment of cancer cells from a primary tumor, entering the body circulation and settling down to grow within normal tissues elsewhere in the body. When tumor cells metastasize, the new tumor is called a secondary or metastatic tumor, and its cells normally resemble those in the original tumor. This means, for example, that, if breast cancer metastasizes to the lungs, the secondary tumor is made up of abnormal breast cells, not of abnormal lung cells. The tumor in the lung is then called metastatic breast cancer, not lung cancer.

The term "pharmaceutical composition" particularly refers to a composition suitable for administering to a human or animal, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

Numeric ranges described herein are inclusive of the numbers defining the range. The headings provided herein are not limitations of the various aspects or embodiments of this invention which can be read by reference to the specification as a whole. According to one embodiment, subject-matter described herein as comprising certain steps in the case of methods or as comprising certain ingredients in the case of compositions refers to subject-matter consisting of the respective steps or ingredients. It is preferred to select and combine preferred aspects and embodiments described herein and the specific subject-matter arising from a respective combination of preferred embodiments also belongs to the present disclosure.

DETAILED DESCRIPTION OF THE INVENTION

The present invention is based on the development of a variant of the humanized anti-MUC1 antibody PankoMab wherein the glycosylation site in the CDR-H2 is deleted. Deletion of the glycosylation site was achieved by substituting amino acid Asn (asparagine) 57 of the heavy chain variable region by another amino acid, especially Gln (glutamine). Asn 57 is the acceptor amino acid residue of the glycosylation site to which the carbohydrate structure is attached. Substituting this asparagine residue by another residue abolishes glycosylation because the carbohydrate structure can only be transferred to an asparagine residue by the enzymes of the host cell. It was surprisingly found that deletion of the glycosylation site in the CDR-H2 of PankoMab increased the antigen binding affinity of the antibody.

In view of these findings, the present invention provides an antibody capable of binding to MUC1, which comprises
  (i) a heavy chain variable region comprising the complementarity-determining regions (CDRs) CDR-H1 having the amino acid sequence of SEQ ID NO: 1, CDR-H2 having the amino acid sequence of SEQ ID NO: 2 and CDR-H3 having the amino acid sequence of SEQ ID NO: 3, and
  (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Binding to MUC1

The antibody specifically binds to an epitope of MUC1. "Specific binding" means binding which is not non-specific adsorption. Examples of criteria for determination on whether binding is specific or not can include a dissociation constant (herein referred to as "K"). The epitope is in the extracellular tandem repeats of MUC1. In certain embodiments, the antibody binds to MUC1 in a glycosylation-dependent manner. In particular, the antibody binds stronger if said tandem repeats are glycosylated at a threonine residue with N-acetyl galactosamine (Tn), sialyl α2-6 N-acetyl galactosamine (sTn), galactose ß1-3 N-acetyl galactosamine (TF) or galactose ß1-3 (sialyl α2-6)N-acetyl galactosamine (sTF), preferably with Tn or TF. Preferably, the carbohydrate moiety is bound to the threonine residue by an α-O-glycosidic bond. The epitope in the tandem repeat domain of MUC1 in particular comprises the amino acid sequence PDTR (SEQ ID NO: 13) or PESR (SEQ ID NO: 14). The binding to this epitope preferably is glycosylation dependent, as described above, wherein in particular the binding is increased if the carbohydrate moiety described above is attached to the threonine residue of the sequence PDTR or PESR (SEQ ID NOs: 13 and 14), respectively.

The epitope is a tumor-associated MUC1 epitope (TA-MUC1). A TA-MUC1 epitope in particular refers to an epitope of MUC1 which is present on tumor cells but not on normal cells and/or which is only accessible by antibodies in the host's circulation when present on tumor cells but not when present on normal cells. In certain embodiments, the binding of the antibody to cells expressing TA-MUC1 epitope is stronger than the binding to cells expressing normal, non-tumor MUC1. Preferably, said binding is at least 1.5-fold stronger, preferably at least 2-fold stronger, at least 5-fold stronger, at least 10-fold stronger or at least 100-fold stronger. For TA-MUC1 binding, the antibody preferably specifically binds the glycosylated MUC1 tumor epitope such that the strength of the bond is increased at least by a factor 2, preferably a factor of 4 or a factor of 10, most preferably a factor of 20 in comparison with the bond to the non-glycosylated peptide of identical length and identical peptide sequence. Said binding can be assayed or determined by ELISA, RIA, surface plasmon resonance (hereinafter, referred to as "SPR") analysis, or the like. Examples of equipment used in the SPR analysis can include BIAcore™ (manufactured by GE Healthcare Bio-Sciences Crop.), ProteOn™ (manufactured by Bio-Rad Laboratories, Inc.), DRX2 Biosensor (manufactured by Dynamic Biosensors GmbH), SPR-Navi™ (manufactured by BioNavis Oy Ltd.), Spreeta™ (manufactured by Texas Instruments Inc.), SPRi-PlexlI™ (manufactured by Horiba, Ltd.), and Autolab SPR™ (manufactured by Metrohm). The binding of the antibody to the antigen expressed on cell surface can be assayed by flow cytometry or the like.

Furthermore, the antibody may exhibit antigen binding properties similar to those of a reference antibody comprising a heavy chain variable region with the amino acid sequence of SEQ ID NO: 11 or SEQ ID NO:10 and a light chain variable region with the amino acid sequence of SEQ ID NO: 12. Preferably, the reference antibody is the humanized antibody PankoMab. In particular, the antibody according to the invention specifically binds to the same antigen as the reference antibody, and preferably binds to said antigen with a higher affinity. That is, the antibody preferably binds to the antigen with an affinity having a dissociation constant which is lower than that of the reference antibody, more preferably at least 10% lower, at least 20% lower, at least 30% lower or at least 50% lower. Moreover, the antibody preferably shows cross-specificity with the reference antibody comprising a heavy chain variable region with the amino acid sequence of SEQ ID NO: 11 and a light chain variable region with the amino acid sequence of SEQ ID NO: 12. In particular, the humanized antibody is able to block the binding of the reference antibody to MUC1 if present in a high enough concentration. This is possible if the binding of the reference antibody to MUC1 is hindered when the antibody according to the invention is already bound to the antigen MUC1.

The Anti-MUC1 Antibody

An antibody capable of binding to MUC1 of the present invention comprises a heavy chain variable region comprising the complementarity-determining regions (CDRs) CDR-H1 having the amino acid sequence of SEQ ID NO: 1, CDR-H2 having the amino acid sequence of SEQ ID NO: 2 and CDR-H3 having the amino acid sequence of SEQ ID NO: 3 and a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

In certain embodiments, the heavy chain variable region comprises an amino acid sequence which is at least 90% identical to the amino acid sequence of SEQ ID NO: 9. Especially, the heavy chain variable region comprises an amino acid sequence which is at least 95%, in particular at least 98% identical to the amino acid sequence of SEQ ID NO: 9. In these embodiments, the heavy chain variable region still comprises CDRs having the amino acid sequences of SEQ ID NOs: 1, 2 and 3. Hence, any sequence deviations to SEQ ID NO: 9 are located in the framework regions, but not in the CDRs. In particular, the heavy chain variable region comprises the amino acid sequence of SEQ ID NO: 9.

In certain embodiments, CDR-H2 has the amino acid sequence of SEQ ID NO: 2, wherein the amino acid at position 8 of SEQ ID NO: 2 is selected from the group consisting of glutamine, alanine, valine, histidine, tryptophan, tyrosine, lysine and arginine; especially glutamine, histidine, tryptophan, tyrosine, lysine and arginine. Preferably, the amino acid at position 8 of SEQ ID NO: 2 is glutamine, histidine, tryptophan, lysine or arginine, especially glutamine. In particular, CDR-H2 has the amino acid sequence of SEQ ID NO: 7.

In specific embodiments, the heavy chain variable region comprises an amino acid sequence which is at least 90% identical to the amino acid sequence of SEQ ID NO: 10. Especially, the heavy chain variable region comprises an amino acid sequence which is at least 95%, in particular at least 98% identical to the amino acid sequence of SEQ ID NO: 10. In these embodiments, the heavy chain variable region comprises the CDR-H1 having the amino acid sequence of SEQ ID NO: 1, CDR-H2 having the amino acid sequence of SEQ ID NO: 7 and CDR-H3 having the amino acid sequence of SEQ ID NO: 3. Hence, any sequence deviations to SEQ ID NO: 10 are located in the framework regions, but not in the CDRs. In particular, the heavy chain variable region comprises the amino acid sequence of SEQ ID NO: 10.

In certain embodiments, the light chain variable region comprises an amino acid sequence which is at least 90% identical to the amino acid sequence of SEQ ID NO: 12. Especially, the light chain variable region comprises an amino acid sequence which is at least 95%, in particular at least 98% identical to the amino acid sequence of SEQ ID NO: 12. In these embodiments, the light chain variable region still comprises CDRs having the amino acid sequences of SEQ ID NOs: 4, 5 and 6. Hence, any sequence deviations to SEQ ID NO: 12 are located in the framework regions, but not in the CDRs. In particular, the light chain variable region comprises the amino acid sequence of SEQ ID NO: 12.

In specific embodiments, the heavy chain variable region has an amino acid sequence which is at least 90% identical to the amino acid sequence of SEQ ID NO: 9, wherein the CDRs still have the amino acid sequences of SEQ ID NOs: 1, 2 and 3, and the light chain variable region has an amino acid sequence which is at least 90% identical to the amino acid sequence of SEQ ID NO: 12, wherein the CDRs still have the amino acid sequences of SEQ ID NOs: 4, 5 and 6. In particular, the heavy chain variable region has an amino acid sequence which is at least 95% identical to the amino acid sequence of SEQ ID NO: 9, wherein the CDRs still have the amino acid sequences of SEQ ID NOs: 1, 2 and 3, and the light chain variable region has an amino acid sequence which is at least 95% identical to the amino acid sequence of SEQ ID NO: 12, wherein the CDRs still have the amino acid sequences of SEQ ID NOs: 4, 5 and 6.

In specific embodiments, the heavy chain variable region has an amino acid sequence which is at least 90% identical to the amino acid sequence of SEQ ID NO: 10, wherein the CDRs still have the amino acid sequences of SEQ ID NOs: 1, 7 and 3, and the light chain variable region has an amino acid sequence which is at least 90% identical to the amino acid sequence of SEQ ID NO: 12, wherein the CDRs still have the amino acid sequences of SEQ ID NOs: 4, 5 and 6. In particular, the heavy chain variable region has an amino acid sequence which is at least 95% identical to the amino acid sequence of SEQ ID NO: 10, wherein the CDRs still have the amino acid sequences of SEQ ID NOs: 1, 7 and 3, and the light chain variable region has an amino acid sequence which is at least 95% identical to the amino acid sequence of SEQ ID NO: 12, wherein the CDRs still have the amino acid sequences of SEQ ID NOs: 4, 5 and 6.

In specific embodiments, the heavy chain variable region comprises an amino acid sequence which is at least 90% identical to the amino acid sequence represented by amino acid Nos 20 to 136 of SEQ ID NO: 20. Especially, the heavy chain variable region comprises an amino acid sequence which is at least 95%, in particular at least 98% identical to the amino acid sequence represented by amino acid Nos 20 to 136 of SEQ ID NO: 20. In these embodiments, the heavy chain variable region comprises the CDR-H1 having the amino acid sequence of SEQ ID NO: 1, CDR-H2 having the amino acid sequence of SEQ ID NO: 2 and CDR-H3 having the amino acid sequence of SEQ ID NO: 3. Hence, any sequence deviations to the amino acid sequence represented by amino acid Nos 20 to 136 of SEQ ID NO: 20 are located in the framework regions, but not in the CDRs. In particular, the heavy chain variable region comprises the amino acid sequence represented by amino acid Nos 20 to 136 of SEQ ID NO: 20. In certain embodiments, the amino acid at position 76 of SEQ ID NO: 20 is selected from the group consisting of glutamine, alanine, valine, histidine, tryptophan, tyrosine, lysine and arginine; especially glutamine, histidine, tryptophan, tyrosine, lysine and arginine.

Preferably, the amino acid at position 76 of SEQ ID NO: 20 is glutamine, histidine, tryptophan, lysine or arginine, especially glutamine. In particular, CDR-H2 has the amino acid sequence of SEQ ID NO: 7 and/or the heavy chain variable region comprises the amino acid sequence represented by amino acid Nos 20 to 136 of SEQ ID NO: 23.

In specific embodiments, the light chain variable region comprises an amino acid sequence which is at least 90% identical to the amino acid sequence represented by amino acid Nos 21 to 133 of SEQ ID NO: 21. Especially, the light chain variable region comprises an amino acid sequence which is at least 95%, in particular at least 98% identical to the amino acid sequence represented by amino acid Nos 21 to 133 of SEQ ID NO: 21. In these embodiments, the light chain variable region still comprises CDRs having the amino acid sequences of SEQ ID NOs: 4, 5 and 6. Hence, any sequence deviations to amino acid sequence represented by amino acid Nos 21 to 133 of SEQ ID NO: 21 are located in the framework regions, but not in the CDRs. In particular, the light chain variable region comprises the amino acid sequence represented by amino acid Nos 21 to 133 of SEQ ID NO: 21.

In specific embodiments, the heavy chain variable region has an amino acid sequence which is at least 90% identical to the amino acid sequence represented by amino acid Nos 20 to 136 of SEQ ID NO: 20, wherein the CDRs still have the amino acid sequences of SEQ ID NOs: 1, 7 and 3, and the light chain variable region has an amino acid sequence which is at least 90% identical to the amino acid sequence represented by amino acid Nos 21 to 133 of SEQ ID NO: 21, wherein the CDRs still have the amino acid sequences of SEQ ID NOs: 4, 5 and 6. In particular, the heavy chain variable region has an amino acid sequence which is at least 95% identical to the amino acid sequence represented by amino acid Nos 20 to 136 of SEQ ID NO: 20, wherein the CDRs still have the amino acid sequences of SEQ ID NOs: 1, 7 and 3, and the light chain variable region has an amino acid sequence which is at least 95% identical to the amino acid sequence represented by amino acid Nos 21 to 133 of SEQ ID NO: 21, wherein the CDRs still have the amino acid sequences of SEQ ID NOs: 4, 5 and 6.

In specific embodiments, the heavy chain comprises an amino acid sequence which is at least 90% identical to the amino acid sequence of SEQ ID NO: 15. Especially, the heavy chain comprises an amino acid sequence which is at least 95%, in particular at least 98% identical to the amino acid sequence of SEQ ID NO: 15. In these embodiments, the heavy chain comprises the CDR-H1 having the amino acid sequence of SEQ ID NO: 1, CDR-H2 having the amino acid sequence of SEQ ID NO: 2 and CDR-H3 having the amino acid sequence of SEQ ID NO: 3. Hence, any sequence deviations to SEQ ID NO: 15 are located in the framework regions, but not in the CDRs. In particular, the heavy chain comprises the amino acid sequence of SEQ ID NO: 15. In certain embodiments, the amino acid at position 57 of SEQ ID NO: 15 is selected from the group consisting of glutamine, alanine, valine, histidine, tryptophan, tyrosine, lysine and arginine; especially glutamine, histidine, tryptophan, tyrosine, lysine and arginine. Preferably, the amino acid at position 57 of SEQ ID NO: 15 is glutamine, histidine, tryptophan, lysine or arginine, especially glutamine. In particular, CDR-H2 has the amino acid sequence of SEQ ID NO: 7 and/or the heavy chain variable region comprises the amino acid sequence represented by amino acid Nos 20 to 136 of SEQ ID NO: 22.

In specific embodiments, the light chain comprises an amino acid sequence which is at least 90% identical to the amino acid sequence of SEQ ID NO: 16. Especially, the light chain comprises an amino acid sequence which is at least 95%, in particular at least 98% identical to the amino acid sequence of SEQ ID NO: 16. In these embodiments, the light chain still comprises CDRs having the amino acid sequences of SEQ ID NOs: 4, 5 and 6. Hence, any sequence deviations to SEQ ID NO: 16 are located in the framework regions, but not in the CDRs. In particular, the light chain comprises the amino acid sequence of SEQ ID NO: 16.

In specific embodiments, the heavy chain has an amino acid sequence which is at least 90% identical to the amino acid sequence of SEQ ID NO: 15, wherein the CDRs still have the amino acid sequences of SEQ ID NOs: 1, 7 and 3, and the light chain variable region has an amino acid sequence which is at least 90% identical to the amino acid sequence of SEQ ID NO: 16, wherein the CDRs still have the amino acid sequences of SEQ ID NOs: 4, 5 and 6. In particular, the heavy chain has an amino acid sequence which is at least 95% identical to the amino acid sequence of SEQ ID NO: 15, wherein the CDRs still have the amino acid sequences of SEQ ID NOs: 1, 7 and 3, and the light chain has an amino acid sequence which is at least 95% identical to the amino acid sequence of SEQ ID NO: 16, wherein the CDRs still have the amino acid sequences of SEQ ID NOs: 4, 5 and 6.

The antibody according to the present invention includes and encompasses modified forms thereof. The modified form of the antibody of the present invention means an antibody of the present invention provided with chemical or biological modification. The chemically modified form includes forms wherein the amino acid skeleton is conjugated with a chemical moiety, forms having a chemically modified N-linked or O-linked carbohydrate chain, and the like. Said chemical moiety or form can be toxic or cytotoxic. Biologically modified forms include forms that have undergone post-translational modification (e.g., N-linked or O-linked glycosylation, N-terminal or C-terminal processing, deamidation, isomerization of aspartic acid, or oxidation of methionine), forms containing a methionine residue added to the N-terminus by expression using prokaryotic host cells, and the like. Such a modified form is also meant to include a form labeled to permit detection or isolation of the antibody of the present invention or the antigen thereof, for example, enzyme-labeled forms, fluorescently labeled forms, and affinity-labeled forms. Such a modified form of the antibody of the present invention is useful in improvement in the stability or blood retention of the original antibody of the present invention, reduction in antigenicity, detection or isolation of the antibody or the antigen, etc.

In particular, the antibody may comprise one or more modifications selected from the group consisting of defucosylation, reduced fucose, N-linked glycosylation, O-linked glycosylation, N-terminal processing, C-terminal processing, deamidation, isomerization of aspartic acid, oxidation of methionine, substitutions of two leucine (L) residues to alanine (A) at position 234 and 235 of the heavy chain (LALA), amidation of a proline residue and deletion or lack of one, two, or three amino acids at the carboxyl terminus. In specific embodiments, the antibody lacks one, two, or three carboxyl-terminal amino acid(s) at one or both heavy chains, or it lacks one carboxyl-terminal amino acid and the carboxyl-terminal proline residues is amidated at one or both heavy chains.

Such a modification may be made at an arbitrary position or the desired position in the antibody thereof. Alternatively, the same or two or more different modifications may be made at one or two or more positions therein.

For example, antibodies produced by cultured mammalian cells are known to lack a carboxyl-terminal lysine residue in its heavy chain (Journal of Chromatography A, 705: 129-134 (1995)). It is also known that occasionally 2 carboxyl-terminal amino acid residues (i.e., glycine and lysine) of a heavy chain are missing and that a proline residue newly located at the carboxyl terminus is amidated (Analytical Biochemistry, 360: 75-83 (2007)). Such lack or modification in these heavy chain sequences, however, affects neither the ability of the antibody to bind to its antigen nor the effector functions (complement activation, antibody-dependent cytotoxicity, etc.) of the antibody.

In certain embodiments, the antibody comprises a deletion or lack of 1 or 2 amino acid(s) in the carboxyl terminus of the heavy chain, and has an amidated residue (e.g., an amidated proline residue at the carboxyl-terminal site of the heavy chain). However, the antibody according to the present invention is not limited to the types described above as long as the deletion mutant maintains the ability to bind to the antigen.

In certain embodiments, two heavy chains of the antibody according to the present invention may be composed of any one type of heavy chain selected from the group consisting of the full length heavy chains and the heavy chains of the deletion mutant or may be composed of the combination of any two types selected therefrom. The quantitative ratio of the deletion variant heavy chain(s) depends on the type of cultured mammalian cells producing the antibody according to the present invention, and the culture conditions of the cells.

In specific embodiments, the antibody according to the present invention can include two heavy chains, both of which lack one carboxyl-terminal amino acid residue.

In specific embodiments, the antibody comprises the heavy chain having an amino acid sequence represented by amino acid Nos 1 to 446 of SEQ ID NO: 15 or 22 and the light chain having an amino acid sequence represented by amino acid Nos 1 to 219 of SEQ ID NO: 16. In certain embodiments, the amino acid at position 57 of SEQ ID NO: 15 is selected from the group consisting of glutamine, alanine, valine, histidine, tryptophan, tyrosine, lysine and arginine; especially glutamine, histidine, tryptophan, tyrosine, lysine and arginine. Preferably, the amino acid at position 57 of SEQ ID NO: 15 is glutamine, histidine, tryptophan, lysine or arginine, especially glutamine.

In certain embodiments, the antibody according to the present invention competes for the binding to TA-MUC1 with an antibody comprising a heavy chain variable region having the amino acid sequence of SEQ ID NO: 10 and a light chain variable region having the amino acid sequence of SEQ ID NO: 12, or an antibody comprising a heavy chain variable region having the amino acid sequence of SEQ ID NO: 11 and a light chain variable region having the amino acid sequence of SEQ ID NO: 12.

In certain embodiments, the antibody has the following properties: (a) specifically binding to MUC1, and/or (b)

having the activity of being internalized into MUC1-expressing cells through binding to MUC1.

In certain embodiments, the antibody comprises at least one antibody heavy chain. Especially, the antibody comprises two antibody heavy chains. The antibody heavy chains in particular comprise a VH domain, a CH1 domain, a hinge region, a CH2 domain and a CH3 domain. In certain other embodiments, the antibody heavy chains comprise a CH2 domain and a CH3 domain, but do not comprise a CH1 domain. In further embodiments, one or more constant domains of the heavy chains may be replaced by other domains, in particular similar domains such as for example albumin. The antibody heavy chains may be of any type, including γ-, α-, ε-, δ- and μ-chains, and preferably are γ-chains, including γ1-, γ2-, γ3- and γ4-chains, especially γ1-chains. Hence, the antibody preferably is an IgG-type antibody such as an IgG1-, IgG3- or IgG4-type antibody, in particular an IgG1-type antibody.

In particular, the antibody further comprises at least one antibody light chain, especially two antibody light chains. The antibody light chains in particular comprise a VL domain and a CL domain. The antibody light chain may be a κ-chain or a λ-chain and especially is a κ-chain.

In certain embodiments, the antibody comprises two antibody heavy chains and two antibody light chains. In particular, the antibody comprises two antibody heavy chains of the γ1-type, each comprising a VH domain, a CH1 domain, a hinge region, a CH2 domain and a CH3 domain, and two antibody light chains of the κ-type, each comprising a VL domain and a CL domain.

In alternative embodiments, the antibody does not comprise an antibody light chain. In these embodiments, the light chain variable region may be fused to the N terminus of the heavy chain variable region or is inserted C terminal to the heavy chain variable region. Peptide linkers may be present to connect the light chain variable region with the remaining parts of the heavy chain.

In preferred embodiments, the antibody comprises an Fc region. The antibody may especially be a whole antibody, comprising two heavy chains each comprising the domains VH, CH1, hinge region, CH2 and CH3, and two light chains each comprising the domains VL and CL. The antibody in particular is capable of binding to one or more human Fcγ receptors, especially human Fcγ receptor IIIA. In alternative embodiments, the antibody does not or not significantly bind the human Fcγ receptor IIIA, and especially does not or not significantly bind to any human Fcγ receptor. In these embodiments the antibody in particular does not comprise a glycosylation site in the CH2 domain.

In alternative embodiments, the antibody does not comprise an Fc region. In these embodiments, the antibody in particular is a single chain variable region fragment (scFv) or another antibody fragment not comprising an Fc region.

Glycosylation of the Anti-MUC1 Antibody

The anti-MUC1 antibody may comprise a CH2 domain in one or more antibody heavy chains. Natural human antibodies of the IgG type comprise an N-glycosylation site in the CH2 domain. The CH2 domains present in the antibody may or may not comprise an N-glycosylation site. In certain embodiments, the antibody does not comprise a glycosylation site in the CH2 domain. In particular, the antibody does not comprise an asparagine residue at the position in the heavy chain corresponding to position 297 according to the IMGT/Eu numbering system. For example, the antibody may comprise an Ala297 mutation in the heavy chain. In these embodiments, the antibody preferably has a strongly reduced ability or completely lacks the ability to induce, via binding to Fcγ receptors, antibody-dependent cellular cytotoxicity (ADCC) and/or antibody-dependent cellular phagocytosis (ADCP) and/or complement-dependent cytotoxicity (CDC). Strongly reduced ability in this respect in particular refers to a reduction to 10% or less, especially 3% or less, 1% or less or 0.1% or less activity compared to the same antibody comprising an N-glycosylation site in its CH2 domains and having a common mammalian glycosylation pattern such as those obtainable by production in human cell lines or in CHO cell lines, for example a glycosylation pattern as described herein. In these embodiments, the antibody in particular is an IgG1-type antibody.

In alternative embodiments, the CH2 domains present in the antibody comprise an N-glycosylation site. This glycosylation site in particular is at an amino acid position corresponding to amino acid position 297 of the heavy chain according to the IMGT/Eu numbering system and has the amino acid sequence motive Asn Xaa Ser/Thr wherein Xaa may be any amino acid except proline. The N-linked glycosylation at Asn297 is conserved in mammalian IgGs as well as in homologous regions of other antibody isotypes. Due to optional additional amino acids which may be present in the variable region or other sequence modifications, the actual position of this conserved glycosylation site may vary in the amino acid sequence of the antibody. Preferably, the glycans attached to the antibody are biantennary complex type N-linked carbohydrate structures, preferably comprising at least the following structure:

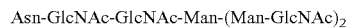

Asn-GlcNAc-GlcNAc-Man-(Man-GlcNAc)$_2$ wherein Asn is the asparagine residue of the polypeptide portion of the antibody; GlcNAc is N-acetylglucosamine and Man is mannose. The terminal GlcNAc residues may further carry a galactose residue, which optionally may carry a sialic acid residue. A further GlcNAc residue (named bisecting GlcNAc) may be attached to the Man nearest to the polypeptide. A fucose may be bound to the GlcNAc attached to the Asn. In these embodiments, the antibody in particular is an IgG1-type antibody.

In preferred embodiments, the antibody does not comprise N-glycolyl neuraminic acids (NeuGc) or detectable amounts of NeuGc. Furthermore, the antibody preferably also does not comprise Galili epitopes (Galα1,3-Gal structures) or detectable amounts of the Galili epitope. In particular, the relative amount of glycans carrying NeuGc and/or Galα1,3-Gal structures is less than 0.1% or even less than 0.02% of the total amount of glycans attached to the CH2 domains of the antibodies in the population of antibodies.

In particular, the antibody has a human glycosylation pattern. Due to these glycosylation properties, foreign immunogenic non-human structures which induce side effects are absent which means that unwanted side effects or disadvantages known to be caused by certain foreign sugar structures such as the immunogenic non-human sialic acids (NeuGc) or the Galili epitope (Gal-Gal structures), both known for rodent production systems, or other structures like immunogenic high-mannose structures as known from e.g. yeast systems are avoided.

In specific embodiments, the antibody comprises a glycosylation pattern having a detectable amount of glycans carrying a bisecting GlcNAc residue. In particular, the relative amount of glycans carrying a bisecting GlcNAc residue is at least 0.5%, especially at least 1% of the total amount of glycans attached to the glycosylation sites of the antibody in a composition. Furthermore, in certain embodiments the glycosylation pattern comprises a relative amount of glycans carrying at least one galactose residue of at least 25% of the total amount of glycans attached to the antibody in a composition. In particular, the relative amount of glycans carrying at least one galactose residue is at least 30%, especially at least 35% or at least 40% of the total amount of glycans attached to the antibody in a composition. In specific embodiments, the glycosylation pattern comprises a relative amount of glycans carrying at least one sialic acid residue of at least 1% of the total amount of glycans attached to the antibody in a composition. In particular, the relative amount of glycans carrying at least one sialic acid residue is at least 1.5%, especially at least 2% of the total amount of glycans attached to the antibody in a composition.

The antibody may have a glycosylation pattern having a high amount of core fucose or a low amount of core fucose. A reduced amount of fucosylation increases the ability of the antibody to induce ADCC. In certain embodiments, the relative amount of glycans carrying a core fucose residue is 40% or less, especially 30% or less or 20% or less of the total amount of glycans attached to the antibody in a composition. In alternative embodiments, the relative amount of glycans carrying a core fucose residue is at least 60%, especially at least 65% or at least 70% of the total amount of glycans attached to the antibody in a composition.

Via the presence or absence of the glycosylation site in the CH2 domain of the anti-MUC1 antibody and the presence or absence of fucose in the glycan structures at said glycosylation site, the ability of the antibody to induce ADCC and the strength of said ADCC induction can be controlled. The ADCC activity is increased by glycosylation of the Fc part of the antibody and further by reducing the amount of fucosylation in said glycosylation. In certain applications, fine tuning of the ADCC activity is important.

Therefore, in certain situations, the antibody without a glycosylation site in the CH2 domain, the antibody with a glycosylation site in the CH2 domain and with a high amount of fucosylation, or the antibody with a glycosylation site in the CH2 domain and with a low amount of fucosylation may be most advantageous.

Production of the Anti-MUC1 Antibody

The antibody is preferably recombinantly produced in a host cell. The host cell used for the production of the antibody may be any host cells which can be used for antibody production. Suitable host cells are in particular eukaryotic host cells, especially mammalian host cells. Exemplary host cells include yeast cells such as *Pichia pastoris* cell lines, insect cells such as SF9 and SF21 cell lines, plant cells, bird cells such as EB66 duck cell lines, rodent cells such as CHO, NS0, SP2/0 and YB2/0 cell lines, and human cells such as HEK293, PER.C6, CAP, CAP-T, AGE1.HN, Mutz-3 and KG1 cell lines.

In certain embodiments, the antibody is produced recombinantly in a human blood cell line, in particular in a human myeloid leukemia cell line. Preferred human cell lines which can be used for production of the antibody as well as suitable production procedures are described in WO 2008/028686 A2. In a specific embodiment, the antibody is obtained by expression in a human myeloid leukemia cell line selected from the group consisting of NM-H9D8, NM-H9D8-E6 and NM-H9D8-E6Q12 and cell lines derived therefrom. These cell lines were deposited under the accession numbers DSM ACC2806 (NM-H9D8; deposited on Sep. 15, 2006), DSM ACC2807 (NM-H9D8-E6; deposited on Oct. 5, 2006) and DSM ACC2856 (NM-H9D8-E6Q12; deposited on Aug. 8, 2007) according to the requirements of the Budapest Treaty at the Deutsche Sammlung von Mikroorganismen und Zellkulturen (DSMZ), Inhoffenstraße 7B, 38124 Braunschweig (DE) by Glycotope GmbH, Robert-Rössle-Str. 10, 13125 Berlin (DE). NM-H9D8 cells provide a glycosylation pattern with a high degree of sialylation, a high degree of bisecting GlycNAc, a high degree of galactosylation and a high degree of fucosylation. NM-H9D8-E6 and NM-H9D8-E6Q12 cells provide a glycosylation pattern similar to that of NM-H9D8 cells, except that the degree of fucosylation is very low. Other suitable cell lines include K562, a human myeloid leukemia cell line present in the American Type Culture Collection (ATCC CCL-243), as well as cell lines derived from the aforementioned.

In further embodiments, the antibody is produced recombinantly in CHO cells. Especially, the antibody may be produced recombinantly in a CHO dhfr- cell line such as the cell line of ATCC No. CRL-9096.

Conjugates of the Anti-MUC1 Antibody

In certain embodiments, the antibody comprises one or more further agents conjugated thereto. The further agent may be any agent suitable for conjugation to the antibody. If more than one further agent is present in the antibody, these further agents may be identical or different, and in particular are all identical. Conjugation of the further agent to the antibody can be achieved using any methods known in the art. The further agent may be covalently, in particular by fusion or chemical coupling, or non-covalently attached to the antibody. In certain embodiments, the further agent is covalently attached to the antibody, especially via a linker moiety. The linker moiety may be any chemical entity suitable for attaching the further agent to the antibody.

The further agent preferably is useful in therapy, diagnosis, prognosis, detecting and/or monitoring of a disease, in particular cancer. For example, the further agent may be selected from the group consisting of radionuclides, chemotherapeutic agents, antibodies or antibody fragments, in particular those of different specificity than the anti-MUC1 antibody, e.g. checkpoint antibodies which block or activate immunomodulatory targets, enzymes, interaction domains, detectable labels, toxins, cytolytic components, immunomodulators, immunoeffectors, MHC class I or class II antigens, and liposomes. A particular preferred further agent is a radionuclide or a cytotoxic agent capable of killing cancer cells, such as a chemotherapeutic agent. In certain preferred embodiments, a chemotherapeutic agent is attached to the anti-MUC1 antibody forming a conjugate.

Specific examples of chemotherapeutic agents that can be conjugated as further agent include alkylating agents such as cisplatin, anti-metabolites, plant alkaloids and terpenoids, vinca alkaloids, podophyllotoxin, taxanes such as taxol, topoisomerase inhibitors such as irinotecan and topotecan, antineoplastics such as doxorubicin or microtubule inhibitors such as auristatins and maytansin/maytansinoids.

The chemotherapeutic agent may in particular be selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansin, a maytansinoid, amatoxin, a methionine aminopeptidase, an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a DHFR inhibitor, an inhibitor of microtubule formation, a stabilizer of microtubule, a stabilizer of actin, a topoisomerase II inhibitor, a platinum compound, a ribosome inhibitor, an RNA polymerase II inhibitor and a bacterial toxin. In specific embodiments, the chemotherapeutic agent attached to the anti-MUC1 antibody is selected from the group consisting of an auristatin, a microtubule inhibitor such as a maytansinoid, a DNA damaging agent, a DNA alkylating agent and a DNA minor groove binder.

In some embodiments of the chemotherapeutic agent is a maytansin or maytansinoid. Specific examples of maytansinoids useful for conjugation include maytansinol, $N^{2'}$-deacetyl-$N^{2'}$-(3-mercapto-1-oxopropyl)-maytansine (DM1), $N^{2'}$-deacetyl-$N^{2'}$-(4-mercapto-1-oxopentyl)-maytansine (DM3), and $N^{2'}$-deacetyl-$N^{2'}$-(4-methyl-4-mercapto-1-oxopentyl)-maytansine (DM4). In particular, DM1 or DM4 is attached to the anti-MUC1 antibody. In some embodiments, the chemotherapeutic agent attached to the anti-MUC1 antibody is an auristatin, in particular monomethyl auristatin F (MMAF), monomethyl auristatin E (MMAE) or auristatin T. In some embodiments, the chemotherapeutic agent attached to the anti-MUC1 antibody is a DNA minor groove binder, in particular pyrrolobenzodiazepine (PBD), pyrrolobenzodiazepine dimer (PBD dimer), duocarmycin, duocarmycin-hydroxybenzamide-azaindole (DUBA), seco-duocarmycin-hydroxybenzamide-azaindole (seco-DUBA) or doxorubicin. In some embodiments, the chemotherapeutic agent attached to the anti-MUC1 antibody is a DNA alkylating agent, in particular indolinobenzodiazepine or oxazolidinobenzodiazepine. In some embodiments, the chemotherapeutic agent attached to the anti-MUC1 antibody is a DNA damaging agent, in particular calicheamicin. In some embodiments, the chemotherapeutic agent attached to the anti-MUC1 antibody is an inhibitor of microtubule formation, in particular a tubulysin, an ansamitocin, podophyllotoxin or vinblastine. In some embodiments, the chemotherapeutic agent attached to the anti-MUC1 antibody is a stabilizer of microtubuli, in particular paclitaxel or an epothilone. In some embodiments, the chemotherapeutic agent attached to the anti-MUC1 antibody is a stabilizer of actin, in particular a phallotoxin. In some embodiments, the chemotherapeutic agent attached to the anti-MUC1 antibody is a topoisomerase II inhibitor, in particular teniposide, XK469, razoxane, amsacrine, idarubicin or mebarone. In some embodiments, the chemotherapeutic agent attached to the anti-MUC1 antibody is a platinum compound, in particular cisplatin, carboplatin, oxaliplatin, nedaplatin, triplatin tetranitrate, phenanthriplatin, picoplatin or sattraplatin. In some embodiments, the chemotherapeutic agent attached to the anti-MUC1 antibody is a ribosome inhibitor, in particular ricin, saporin, abrin, diphtheria toxin or exotoxin A. In some embodiments, the chemotherapeutic agent attached to the anti-MUC1 antibody is an RNA polymerase II inhibitor, in particular an amatoxin, such as, for example, amanitin. In some embodiments, the chemotherapeutic agent attached to the anti-MUC1 antibody is a bacterial toxin, in particular anthrax toxin. Suitable antibody drug conjugates are also described in EP 16 151 774.3 and LU 92659, to which is explicitly referred to herewith.

In certain embodiments, the further agent is a polypeptide or protein. This polypeptide or protein may in particular be fused to a polypeptide chain of the antibody. In certain embodiments, the further agent being a polypeptide or protein is fused to the C terminus of an antibody light chain of the antibody. In embodiments wherein the antibody comprises two antibody light chains, a further agent being a polypeptide or protein may be fused to the C terminus of each of the two antibody light chains. In further embodiments, the further agent being a polypeptide or protein is fused to the C terminus of an antibody heavy chain of the antibody. In embodiments wherein the antibody comprises two antibody heavy chains, a further agent being a polypeptide or protein may be fused to the C terminus of each of the two antibody heavy chains. The further agents may be identical or different and in particular have the same amino acid sequence. Suitable examples of such further agents being a polypeptide or protein may be selected from the group consisting of cytokines, chemokines, antibodies, antigen binding fragments, enzymes, and interaction domains.

In certain embodiments, the further agent being a polypeptide or protein is a checkpoint antibody which blocks and/or triggers activating signals. Examples of respective targets include CD40, CD3, CD137 (4-1BB), OX40, GITR, CD27, CD278 (ICOS), CD154 (CD40 ligand), CD270 (HVEM) and CD258 (LIGHT) as activating targets, CTLA4, PD1, CD80, CD244, A2AR, B7-H3 (CD276), B7-H4 (VTCN1), BTLA, IDO, KIR, LAG3, TIM-3, VISTA and phosphatidylserine as inhibitory targets, and their respective ligands such as PDL1. In specific examples, the anti-MUC1 antibody comprises two heavy chains and two light chains as described herein, wherein a scFv fragment specifically binding to CD3 is fused to the C terminus of each heavy chain; or wherein a scFv fragment specifically binding to PDL1 is fused to the C terminus of each light chain.

In further embodiments, the further agent being a polypeptide or protein is an immunomodulatory compound such as a chemokine, cytokine or growth factor. Suitable cytokines in this respect include interferons such as interferon-a, interferon-p and interferon-y, and interleukins. Suitable growth factors include G-CSF and GM-CSF.

The Nucleic Acid, Expression Cassette, Vector, Cell Line and Composition

In a further aspect, the present invention provides a nucleic acid encoding the antibody. The nucleic acid sequence of said nucleic acid may have any nucleotide sequence suitable for encoding the antibody. However, preferably the nucleic acid sequence is at least partially adapted to the specific codon usage of the host cell or organism in which the nucleic acid is to be expressed, in particular the human codon usage. The nucleic acid may be double-stranded or single-stranded DNA or RNA, preferably double-stranded DNA such as cDNA or single-stranded RNA such as mRNA. It may be one consecutive nucleic acid molecule or it may be composed of several nucleic acid molecules, each coding for a different part of the antibody. In preferred embodiments, the present invention provides a nucleotide sequence of the heavy chain of PankoMab variant (PM-N54Q) represented by SEQ ID NO: 17 and a nucleotide sequence of the light chain of PankoMab variant (PM-N54Q) represented by SEQ ID NO: 18.

If the antibody is composed of more than one different amino acid chain, such as a light chain and a heavy chain of the antibody, the nucleic acid may, for example, be a single nucleic acid molecule containing several coding regions each coding for one of the amino acid chains of the antibody, preferably separated by regulatory elements such as IRES elements in order to generate separate amino acid chains, or the nucleic acid may be composed of several nucleic acid molecules wherein each nucleic acid molecule comprises one or more coding regions each coding for one of the amino acid chains of the antibody. In addition to the coding regions encoding the antibody, the nucleic acid may also comprise further nucleic acid sequences or other modifications which, for example, may code for other proteins, may influence the transcription and/or translation of the coding region(s), may influence the stability or other physical or chemical properties of the nucleic acid, or may have no function at all.

In a further aspect, the present invention provides an expression cassette or vector comprising a nucleic acid according to the invention and a promoter operatively connected with said nucleic acid. In addition, the expression cassette or vector may comprise further elements, in particular elements which are capable of influencing and/or regulating the transcription and/or translation of the nucleic acid, the amplification and/or reproduction of the expression cassette or vector, the integration of the expression cassette or vector into the genome of a host cell, and/or the copy number of the expression cassette or vector in a host cell. Suitable expression cassettes and vectors comprising respective expression cassettes for expressing antibodies are well known in the prior art and thus, need no further description here.

Furthermore, the present invention provides a host cell comprising the nucleic acid according to the invention or the expression cassette or vector according to the invention. The host cell may be any host cell. It may be an isolated cell or a cell comprised in a tissue. Preferably, the host cell is a cultured cell, in particular a primary cell or a cell of an established cell line, preferably a tumor-derived cell. Preferably, it is a bacterial cell such as *E. coli*, a yeast cell such as a *Saccharomyces* cell, in particular *S. cerevisiae*, an insect cell such as a Sf9 cell, or a mammalian cell, in particular a human cell such as a tumor-derived human cell, a hamster cell such as CHO, or a primate cell. In a preferred embodiment of the invention the host cell is derived from human myeloid leukaemia cells. Preferably, it is selected from the following cells or cell lines: K562, KG1, MUTZ-3, or a cell or cell line derived therefrom, or a mixture of cells or cell lines comprising at least one of those aforementioned cells. The host cell is preferably selected from the group consisting of NM-H9D8, NM-H9D8-E6, NM H9D8-E6012, and a cell or cell line derived from anyone of said host cells. These cell lines and their properties are described in detail in the PCT-application WO 2008/028686 A2. In further embodiments, the host cell is of a CHO dhfr- cell line such as the cell line of ATCC No. CRL-9096. In preferred embodiments, the host cell is optimized for expression of glycoproteins, in particular antibodies, having a specific glycosylation pattern. Preferably, the codon usage in the coding region of the nucleic acid according to the invention and/or the promoter and the further elements of the expression cassette or vector are compatible with and, more preferably, optimized for the type of host cell used. Preferably, the antibody is produced by a host cell or cell line as described above.

In a specific aspect, the present invention provides a method of producing the antibody in a host cells as described herein. The method in particular comprises the steps of providing a host cell comprising a nucleic acid encoding the antibody, culturing the host cell under conditions suitable for expression of the antibody, and obtaining the antibody expressed by the host cell. The antibody according to the invention may be obtained or obtainable by said method.

In another aspect, the present invention provides a composition comprising the antibody, the nucleic acid, the expression cassette or vector, or the host cell. The composition may also contain more than one of these components. Furthermore, the composition may comprise one or more further components selected from the group consisting of solvents, diluents, and excipients Preferably, the composition is a pharmaceutical composition. In this embodiment, the components of the composition preferably are all pharmaceutically acceptable. The composition may be a solid or fluid composition, in particular a—preferably aqueous—solution, emulsion or suspension or a lyophilized powder.

Use in Medicine

The antibody in particular is useful in medicine, in particular in therapy, diagnosis, prognosis, detecting and/or monitoring of a disease, in particular a disease as described herein, preferably cancer, infections, inflammatory diseases, graft-versus-host disease and immunodeficiencies.

Therefore, in a further aspect, the invention provides the antibody, the nucleic acid, the expression cassette or vector, the host cell, or the composition for use in medicine. Preferably, the use in medicine is a use in the treatment, prognosis, diagnosis, detecting and/or monitoring of a disease such as, for example, diseases associated with abnormal cell growth such as cancer, infections such as bacterial, viral, fungal or parasitic infections, inflammatory diseases such as autoimmune diseases and inflammatory bowel diseases, and diseases associated with a reduce immune activity such as immunodeficiencies. In a preferred embodiment, the disease is cancer.

Preferably, the cancer has a detectable expression of MUC1 or TA-MUC1, preferably detectable by immunohistochemistry, ELISA, RIA, enzyme-linked immunospot (ELISPOT) assay, dot blotting, Ouchterlony test or counterimmunoelectrophoresis (CIE), or in-situ hybridization. It especially includes cells having an MUC1 or TA-MUC1 expression which is detectable by immunohistochemistry or in-situ hybridization. The cancer may be tested on MUC1 or TA-MUC1 level prior to administration of the anti-MUC1 antibody.

The present invention further provides kits and devices comprising the antibody according to the invention, and associated methods that are useful in the diagnosis, detecting or monitoring of MUC1 associated disorders such as cancer. In some embodiments, a sandwich ELISA kit for testing, detecting or diagnosis comprising the antibody of the present invention is provided. This kit may further comprise one or more of a solution of MUC1 or TA-MUC1 protein standards, a coloring reagent, a buffer solution for dilution, an antibody for solid phase, an antibody for detection, and a washing solution, and the like. Preferably, the amount of the antibody bound to the antigen can be measured by the application of a method such as an absorbance, fluorescence, luminescence, or radioisotope (RI) method. Preferably, an absorbance plate reader, a fluorescence plate reader, a luminescence plate reader, an RI liquid scintillation counter, or the like is used in the measurement.

In some embodiments, the present invention provides the antibody according to the invention for use in immunohistochemistry (IHC) analysis, and a composition comprising the same.

The immunohistochemistry is not particularly limited as long as this approach involves reacting a tissue section with an antigen-binding antibody (primary antibody) and detecting the primary antibody bound with the antigen.

Different forms of cancers including metastases can be treated with the antibody according to the invention. The cancer can in particular be selected from the group consisting of colon cancer, lung cancer, ovarian cancer, breast cancer such as triple negative breast cancer, pancreatic cancer, cervical cancer, endometrial cancer, gastrointestinal cancer, kidney cancer, head and neck cancer, thyroid cancer and urothelial cancer. The cancer may further in particular be selected from stomach cancer, liver cancer, bladder cancer, skin cancer, prostate cancer and blood cancer. In certain embodiments, the cancer is a metastasizing cancer.

The cancer may include any type of metastases, such as skin metastases, lymph node metastases, lung metastases, liver metastases, peritoneal metastases, pleural metastases and/or brain metastases. In certain embodiments, the cancer has an inflammatory phenotype. In these embodiments, any of the cancer types described above may be an inflammatory cancer.

In certain embodiments, the viral infection is caused by human immunodeficiency virus, herpes simplex virus, Epstein Barr virus, influenza virus, lymphocytic choriomeningitis virus, hepatitis B virus or hepatitis C virus. The inflammatory disease may be selected from inflammatory bowel disease, pelvic inflammatory disease, ischemic stroke, Alzheimer's disease, asthma, pemphigus vulgaris and dermatitis/eczema. The autoimmune disease may be selected from the group consisting of celiac disease, diabetes mellitus type 1, Graves' disease, inflammatory bowel disease, multiple sclerosis, psoriasis, rheumatoid arthritis, systemic lupus erythematosus, vitiligo, psoriatic arthritis, atopic dermatitis, scleroderma, sarcoidosis, primary biliary cirrhosis, Guillain-Barre syndrome, autoimmune hepatitis and ankylosing spondylitis. In certain embodiments, the disease comprises or is associated with cells which express MUC1, especially TA-MUC1. For example, a cancer to be treated is MUC1 positive, especially TA-MUC1 positive, i.e. comprises cancer cells which express MUC1, especially TA-MUC1.

In specific embodiments, the antibody is used for treatment in combination with another therapeutic agent, especially for treatment of cancer in combination with another anti-cancer agent. Said further therapeutic agent may be any known anti-cancer agent. Suitable anti-cancer therapeutic agents which may be combined with the antibody according to the invention may be chemotherapeutic agents, other antibodies, immunostimulatory agents, cytokines, chemokines, and vaccines. Furthermore, therapy with the antibody may be combined with radiation therapy, surgery and/or traditional Chinese medicine.

Anti-cancer agents that can be used in combination with the anti-MUC1 antibody may be selected from any chemotherapeutic agent, in particular chemotherapeutic agents known to be effective for treatment of MUC1 positive cancers. The type of chemotherapeutic agent also depends on the cancer to be treated. The combination partner may be selected from the group consisting of taxanes such as paclitaxel (Taxol), docetaxel (Taxotere) and SB-T-1214; cyclophosphamide; imatinib; pazopanib; capecitabine; cytarabine; vinorelbine; gemcitabine; anthracyclines such as daunorubicin, doxorubicin, epirubicin, idarubicin, valrubicin and mitoxantrone; aromatase inhibitors such as aminoglutethimide, testolactone (Teslac), anastrozole (Arimidex), letrozole (Femara), exemestane (Aromasin), vorozole (Rivizor), formestane (Lentaron), fadrozole (Afema), 4-hydroxyandrostenedione, 1,4,6-androstatrien-3,17-dione (ATD) and 4-androstene-3,6,17-trione (6-OXO); topoisomerase inhibitors such as irinotecan, topotecan, camptothecin, lamellarin D, etoposide (VP-16), teniposide, doxorubicin, daunorubicin, mitoxantrone, amsacrine, ellipticines, aurintricarboxylic acid and HU-331; platinum based chemotherapeutic agents such as cis-diamminedichloroplatinum(II) (cisplatin), cis-diammine(1,1-cyclobutanedicarboxylato)platinum(II) (carboplatin) and [(1R,2R)-cyclohexane-1,2-diamine](ethanedioato-O,O')platinum(II) (oxaliplatin); PARP inhibitors such as olaparib, rucaparib and niraparib; TLR agonists such as imiquimod and resiquimod; and antimetabolites, in particular antifolates such as methotrexate, pemetrexed, raltitrexed and pralatrexate, pyrimidine analogues such as fluoruracil, gemcitabine, floxuridine, 5-fluorouracil and tegafur-uracil, and purine analogues, selective estrogen receptor modulators and estrogen receptor downregulators.

Furthermore, also therapeutic antibodies can be used as further combination partner. It may be any antibody that is useful in cancer therapy which is different from the anti-MUC1 antibody. In particular, the further antibody is approved for cancer treatment by an administration such as the U.S. Food and Drug Administration (FDA), the European Medicines Agency (EMA, formerly EMEA) and the Bundesinstitut für Arzneimittel und Medizinprodukte (BfArM). Examples of the further antibody that can be used for combination treatment are anti-EGFR antibodies such as Cetuximab, Tomuzotuximab, Panitumumab, Zalutumumab, Nimotuzumab, Matuzumab and Necitumumab; anti-HER2 antibodies such as Trastuzumab, Timigutuzumab and Pertuzumab; anti-VEGF antibodies such as bevacizumab (Avastin); anti-CD52 antibodies such as alemtuzumab (Campath); anti-CD30 antibodies such as brentuximab (Adcetris); anti-CD33 antibodies such as gemtuzumab (Mylotarg); and anti-CD20 antibodies such as rituximab (Rituxan, Mabthera), tositumomab (Bexxar) and ibritumomab (Zevalin). Further exemplary antibodies suitable for combination with the cancer therapy described herein include antibodies against antigens selected from the group consisting of Thomsen-Friedenreich antigen (TFα, TFβ), Tn, Lewis Y, CD44, folate receptor a, NeuGc-GM3 ganglioside, DLL-3, RANKL, PTK7, Notch-3, Ephrin A4, insulin-like growth factor receptor 1, activin receptor-like kinase-1, claudin-6, disialoganglioside GD2, endoglin, transmembrane glycoprotein NMB, CD56, tumor-associated calcium signal transducer 2, tissue factor, ectonucleotide pyrophosphatase/phosphodiesterase 3, CD70, P-cadherin, mesothelin, six transmembrane epithelial antigen of the prostate 1 (STEAP1), carcinoembryonic antigen-related cell adhesion molecule 5 (CEACAM5), nectin 4, guanylyl cyclase C, solute carrier family 44 member 4 (SLC44A4), prostate-specific membrane antigen (PSMA), zinc transporter ZIP6 (LIV1 (ZIP6)), SLIT and NTRK-like protein 6 (SLITRK6), trophoblast glycoprotein (TPBG; 5T4), Fyn3, carbonic anhydrase 9, NaPi2b, fibronectin extra-domain B, endothelin receptor ETB, VEGFR2 (CD309), tenascin c, collagen IV and periostin.

The anti-MUC1 antibody can further be combined with checkpoint antibodies, i.e. antibodies blocking or activating immunomodulatory targets. Thereby, inhibitory signals for an immune response can be blocked and/or activating signals can be triggered. Examples of respective targets include CD40, CD3, CD137 (4-1BB), OX40, GITR, CD27, CD278 (ICOS), CD154 (CD40 ligand), CD270 (HVEM) and CD258 (LIGHT) as activating targets, CTLA4, PD1, CD80, CD244, A2AR, B7-H3 (CD276), B7-H4 (VTCN1), BTLA, IDO, KIR, LAG3, TIM-3, VISTA and phosphatidylserine as inhibitory targets, and their respective ligands such as PDL1.

In further embodiments, the anti-MUC1 antibody can be combined with the treatment with immunomodulatory compounds such as chemokines, cytokines, growth factors and vaccines. Suitable cytokines in this respect include interferons such as interferon-α, interferon-β and interferon-γ, and interleukins. Suitable growth factors include G-CSF and GM-CSF.

The anti-MUC1 antibody preferably is used for treatment of a primary tumor, a recurrent tumor and/or metastases of such tumors, and in particular is used for treatment before, during or after surgery and for the prevention or treatment of metastases. The anti-MUC1 antibody in particular is for the treatment of a patient as adjuvant therapy. In certain embodiments, the anti-MUC1 antibody is for the treatment of a patient as neoadjuvant therapy or in a combined neoadjuvant-adjuvant therapy. Furthermore, the anti-MUC1 antibody is for the treatment of a patient as palliative therapy.

The cancer therapy with the anti-MUC1 antibody preferably results in inhibition of tumor growth and in particular reduction of tumor size. Furthermore, the occurrence of further metastases is prevented and/or their number is reduced by the treatment. The treatment preferably results in an increase in progression-free survival; and/or an increase in lifespan and thus the overall survival.

The present invention further provides methods of therapy, diagnosis, prognosis, detecting and/or monitoring of a disease using the antibody according to the invention. The embodiments and examples of the use of the antibody in medicine also apply likewise to the medical methods. In particular, a method for treating a disease in a subject in need thereof comprising administering to the subject a therapeutically effective amount of the antibody according to the present invention is provided.

For example, the invention provides a method for treating cancer in a subject in need thereof comprising, administering to the subject with cancer a therapeutically effective amount of the antibody according to the invention. In specific embodiments, the cancer is characterized by expressing TA-MUC1. The cancer may be selected from the group consisting of ovarian cancer, breast cancer, pancreatic cancer, lung cancer, colon cancer, stomach cancer, liver cancer, kidney cancer, blood cancer, endometrial cancer, thyroid cancer, leukemia, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

Furthermore, the invention provides a method for diagnosis, detecting or monitoring cancer, comprising the step of contacting a test sample with an antibody according to the invention.

Methods of Increasing the MUC1 Binding Affinity

In a further aspect, the invention provides a method of increasing the MUC1 binding affinity of an antibody comprising (i) a heavy chain variable region comprising the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6, the method comprising the step of substituting the amino acid residue at position 8 of CDR-H2 with any amino acid residue except asparagine, resulting in CDR-H2 having the amino acid sequence of SEQ ID NO: 2.

The antibody which MUC1 binding affinity is to be increased in particular is an antibody capable of binding to MUC1 as described herein, except that it comprises an asparagine at position 8 of the CDR-H2 sequence.

In certain embodiments, the heavy chain variable region of the antibody which MUC1 binding affinity is to be increased comprises an amino acid sequence which is at least 90% identical to the amino acid sequence of SEQ ID NO: 11. Especially, the heavy chain variable region comprises an amino acid sequence which is at least 95%, in particular at least 98% identical to the amino acid sequence of SEQ ID NO: 11. In these embodiments, the heavy chain variable region still comprises CDRs having the amino acid sequences of SEQ ID NOs: 1, 8 and 3. Hence, any sequence deviations to SEQ ID NO: 11 are located in the framework regions, but not in the CDRs. In particular, the heavy chain variable region comprises the amino acid sequence of SEQ ID NO: 11.

In certain embodiments, the light chain variable region of the antibody which MUC1 binding affinity is to be increased comprises an amino acid sequence which is at least 90% identical to the amino acid sequence of SEQ ID NO: 12. Especially, the light chain variable region comprises an amino acid sequence which is at least 95%, in particular at least 98% identical to the amino acid sequence of SEQ ID NO: 12. In these embodiments, the light chain variable region still comprises CDRs having the amino acid sequences of SEQ ID NOs: 4, 5 and 6. Hence, any sequence deviations to SEQ ID NO: 12 are located in the framework regions, but not in the CDRs. In particular, the light chain variable region comprises the amino acid sequence of SEQ ID NO: 12.

In specific embodiments, the heavy chain variable region of the antibody which MUC1 binding affinity is to be increased has an amino acid sequence which is at least 90% identical to the amino acid sequence of SEQ ID NO: 11, wherein the CDRs still have the amino acid sequences of SEQ ID NOs: 1, 8 and 3, and the light chain variable region has an amino acid sequence which is at least 90% identical to the amino acid sequence of SEQ ID NO: 12, wherein the CDRs still have the amino acid sequences of SEQ ID NOs: 4, 5 and 6. In particular, the heavy chain variable region has an amino acid sequence which is at least 95% identical to the amino acid sequence of SEQ ID NO: 11, wherein the CDRs still have the amino acid sequences of SEQ ID NOs: 1, 8 and 3, and the light chain variable region has an amino acid sequence which is at least 95% identical to the amino acid sequence of SEQ ID NO: 12, wherein the CDRs still have the amino acid sequences of SEQ ID NOs: 4, 5 and 6.

For example, the antibody which MUC1 binding affinity is to be increased is an anti-MUC1 antibody as disclosed in WO 2004/065423 A2 or WO 2011/012309 A1. In particular, the antibody which MUC1 binding affinity is to be increased is gatipotuzumab or PankoMab.

The antibody which MUC1 binding affinity is increased in particular is an antibody capable of binding to MUC1 as described herein.

In certain embodiments, MUC1 binding is as described herein. Increasing the MUC1 or TA-MUC1 binding affinity in particular refers to an increase of at least 10%, at least 20%, at least 33% or at least 50%. In preferred embodiments, MUC1 binding affinity is increased by at least 50%. The MUC1 binding affinity may be determined as described in the examples, especially using surface plasmon resonance analysis or switchSENSE® Technology (DRX2 Biosensor, manufactured by Dynamic Biosensors GmbH), as described, e.g., in example 4a and b.

In certain embodiments, the step of substituting the amino acid residue at position 8 of CDR-H2 is achieved by introducing a mutation into the nucleic acid coding for the antibody, wherein the mutation is introduced in the codon coding for said amino acid residue. Introducing the mutation can be done by any method. Several suitable methods are known in the art and the skilled person is capable of performing the necessary tasks to introduce the mutation. The antibody with increased MUC1 binding affinity can then be obtained by expressing the mutated nucleic acid, for example in a host cell. Nucleic acids, host cells and methods for producing the antibody are described herein and can be used for the method for increasing the MUC1 binding affinity.

In specific embodiments, the method of increasing the MUC1 binding affinity of an antibody comprises the steps of
- (a) providing a nucleic acid coding for the antibody which MUC1 binding affinity is to be increased
- (b) introducing a mutation into said nucleic acid to produce a mutated nucleic acid, wherein the mutation is introduced in the codon coding for the amino acid residue at position 8 of CDR-H2 so that said codon codes for any amino acid residue except asparagine; and
- (c) expressing the mutated nucleic acid to produce an antibody with increased MUC1 binding affinity.

The present invention further provides a method of producing an antibody with increased MUC1 binding affinity, comprising
- (a) providing a nucleic acid coding for an antibody which comprises
  - (i) a heavy chain variable region comprising the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
  - (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
- (b) introducing a mutation into said nucleic acid to produce a mutated nucleic acid, wherein the mutation is introduced in the codon coding for the amino acid residue at position 8 of CDR-H2 so that said codon codes for any amino acid residue except asparagine; and
- (c) producing the antibody with increased MUC1 binding affinity by expressing the mutated nucleic acid in a host cell.

The embodiments, features and examples described herein for the other aspects, especially for the method of increasing the MUC1 binding affinity of an antibody, also likewise apply to the method of producing an antibody with increased MUC1 binding affinity.

In certain embodiments, the method of producing an antibody with increased MUC1 binding affinity further comprises a step (d) of processing the antibody with increased MUC1 binding affinity.

For example, processing the antibody with increased MUC1 binding affinity may include isolating the antibody from the cell culture. Isolation of the antibody in particular refers to the separation of the antibody from the remaining components of the cell culture. Separation of the antibody from the cell culture medium may be performed, for example, by chromatographic methods. Suitable methods and means for isolating antibodies are known in the art and can be readily applied by the skilled person.

The obtained antibody may optionally be subject to further processing steps such as e.g. modification steps such as chemical or enzymatic coupling of a further agent to the antibody, and/or formulation steps in order to produce the antibody in the desired quality and composition. Such further processing steps and methods are generally known in the art.

In further embodiments, step (d) additionally comprises the step of providing a pharmaceutical formulation comprising the antibody. Providing a pharmaceutical formulation comprising the antibody or formulating the antibody as a pharmaceutical composition in particular comprises exchanging the buffer solution or buffer solution components of the composition comprising the antibody. Furthermore, this step may include lyophilization of the antibody. In particular, the antibody is transferred into a composition only comprising pharmaceutically acceptable ingredients.

Specific Embodiments

In the following, specific embodiments of the present invention are described.

Embodiment 1. An antibody capable of binding to MUC1, which comprises
- (i) a heavy chain variable region comprising the complementarity-determining regions (CDRs) CDR-H1 having the amino acid sequence of SEQ ID NO: 1, CDR-H2 having the amino acid sequence of SEQ ID NO: 2 and CDR-H3 having the amino acid sequence of SEQ ID NO: 3, and
- (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 2. The antibody according to Embodiment 1, wherein the amino acid at position 8 of the CDR-H2 is selected from the group consisting of glutamine, alanine, valine, histidine, tryptophan, tyrosine, lysine and arginine, especially glutamine, histidine, tryptophan, tyrosine, lysine and arginine, in particular glutamine.

Embodiment 3. The antibody according to Embodiment 1, wherein the amino acid at position 8 of the CDR-H2 is glutamine, histidine, arginine, tryptophan, or lysine.

Embodiment 4. The antibody according to Embodiments 1 to 3, wherein the CDR-H2 has the amino acid sequence of SEQ ID NO: 7.

Embodiment 6. An antibody capable of binding to MUC1, which comprises
- (i) a heavy chain variable region, which
  - (a) has an amino acid sequence which is at least 90% identical to the amino acid sequence of SEQ ID NO: 9, and
  - (b) comprises the complementarity-determining regions (CDRs) CDR-H1 having the amino acid sequence of SEQ ID NO: 1, CDR-H2 having the amino acid sequence of SEQ ID NO: 2 and CDR-H3 having the amino acid sequence of SEQ ID NO: 3, and
- (ii) a light chain variable region, which
  - (a) has an amino acid sequence which is at least 90% identical to the amino acid sequence of SEQ ID NO: 12, and
  - (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 7. An antibody capable of binding to MUC1, which comprises
  (i) a heavy chain variable region, which
    (a) has an amino acid sequence which is at least 95% identical to the amino acid sequence of SEQ ID NO: 9, and
    (b) comprises the complementarity-determining regions (CDRs) CDR-H1 having the amino acid sequence of SEQ ID NO: 1, CDR-H2 having the amino acid sequence of SEQ ID NO: 2 and CDR-H3 having the amino acid sequence of SEQ ID NO: 3, and
  (ii) a light chain variable region, which
    (a) has an amino acid sequence which is at least 95% identical to the amino acid sequence of SEQ ID NO: 12, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 8. The antibody according to Embodiment 6 or 7, wherein the amino acid at position 8 of the CDR-H2 is selected from the group consisting of glutamine, alanine, valine, histidine, tryptophan, tyrosine, lysine and arginine, especially glutamine, histidine, tryptophan, tyrosine, lysine and arginine, in particular glutamine.

Embodiment 9. The antibody according to Embodiment 7 or 8, wherein the amino acid at position 8 of the CDR-H2 is glutamine, histidine, arginine, tryptophan, or lysine.

Embodiment 10. An antibody capable of binding to MUC1, which comprises
  (i) a heavy chain variable region, which
    (a) has an amino acid sequence which is at least 90% identical to the amino acid sequence of SEQ ID NO: 10, and
    (b) comprises the complementarity-determining regions (CDRs) CDR-H1 having the amino acid sequence of SEQ ID NO: 1, CDR-H2 having the amino acid sequence of SEQ ID NO: 7 and CDR-H3 having the amino acid sequence of SEQ ID NO: 3, and
  (ii) a light chain variable region, which
    (a) has an amino acid sequence which is at least 90% identical to the amino acid sequence of SEQ ID NO: 12, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 11. An antibody capable of binding to MUC1, which comprises
  (i) a heavy chain variable region, which
    (a) has an amino acid sequence which is at least 95% identical to the amino acid sequence of SEQ ID NO: 10, and
    (b) comprises the complementarity-determining regions (CDRs) CDR-H1 having the amino acid sequence of SEQ ID NO: 1, CDR-H2 having the amino acid sequence of SEQ ID NO: 7 and CDR-H3 having the amino acid sequence of SEQ ID NO: 3, and
  (ii) a light chain variable region, which
    (a) has an amino acid sequence which is at least 95% identical to the amino acid sequence of SEQ ID NO: 12, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 12. An antibody capable of binding to MUC1, which comprises
  (i) a heavy chain variable region, which has the amino acid sequence of SEQ ID NO: 9, and
  (ii) a light chain variable region, which has the amino acid sequence of SEQ ID NO: 12.

Embodiment 13. The antibody according to Embodiment 12, wherein the amino acid at position 57 of SEQ ID NO: 9 is selected from the group consisting of glutamine, alanine, valine, histidine, tryptophan, tyrosine, lysine and arginine, especially glutamine, histidine, tryptophan, tyrosine, lysine and arginine, in particular glutamine.

Embodiment 14. The antibody according to Embodiment 12, wherein the amino acid at position 57 of SEQ ID NO: 9 is glutamine, histidine, arginine, tryptophan, or lysine.

Embodiment 15. An antibody capable of binding to MUC1, which comprises
  (i) a heavy chain variable region, which has the amino acid sequence of SEQ ID NO: 10, and
  (ii) a light chain variable region, which has the amino acid sequence of SEQ ID NO: 12.

Embodiment 16. An antibody capable of binding to MUC1, which comprises
  (i) a heavy chain variable region, which
    (a) has an amino acid sequence which is at least 90% or at least 95% identical to the amino acid sequence represented by amino acid Nos 20 to 136 of SEQ ID NO: 20, and
    (b) comprises the complementarity-determining regions (CDRs) CDR-H1 having the amino acid sequence of SEQ ID NO: 1, CDR-H2 having the amino acid sequence of SEQ ID NO: 2 or 7 and CDR-H3 having the amino acid sequence of SEQ ID NO: 3, and
  (ii) a light chain variable region, which
    (a) has an amino acid sequence which is at least 90% or at least 95% identical to the amino acid sequence represented by amino acid Nos 21 to 133 of SEQ ID NO: 21, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 17. An antibody capable of binding to MUC1, which comprises
  (i) a heavy chain variable region, which has the amino acid sequence represented by amino acid Nos 20 to 136 of SEQ ID NO: 20 or 23, and
  (ii) a light chain variable region, which has amino acid sequence represented by amino acid Nos 21 to 133 of SEQ ID NO: 21.

Embodiment 18. An antibody capable of binding to MUC1, which comprises
  (i) a heavy chain, which
    (a) has an amino acid sequence which is at least 90% or at least 95% identical to the amino acid sequence of SEQ ID NO: 15, and
    (b) comprises the complementarity-determining regions (CDRs) CDR-H1 having the amino acid sequence of SEQ ID NO: 1, CDR-H2 having the amino acid sequence of SEQ ID NO: 2 or 7 and CDR-H3 having the amino acid sequence of SEQ ID NO: 3, and (ii) a light chain variable region, which
  (a) has an amino acid sequence which is at least 90% or 95% identical to the amino acid sequence of SEQ ID NO: 16, and
  (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 19. An antibody capable of binding to MUC1, which comprises
  (i) a heavy chain variable region, which has the amino acid sequence of SEQ ID NO: 15 or SEQ ID NO: 22, and
  (ii) a light chain variable region, which has the amino acid sequence of SEQ ID NO: 16.

Embodiment 20. An antibody capable of binding to MUC1, which comprises
  (i) a heavy chain variable region, which
    (a) has an amino acid sequence which is at least 90% or at least 95% identical to the amino acid sequence represented by amino acid Nos 20 to 460 of SEQ ID NO: 20, and
    (b) comprises the complementarity-determining regions (CDRs) CDR-H1 having the amino acid sequence of SEQ ID NO: 1, CDR-H2 having the amino acid sequence of SEQ ID NO: 2 or 7 and CDR-H3 having the amino acid sequence of SEQ ID NO: 3, and
  (ii) a light chain variable region, which
    (a) has an amino acid sequence which is at least 90% or 95% identical to the amino acid sequence represented by amino acid Nos 21 to 239 of SEQ ID NO: 21, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

Embodiment 21. An antibody capable of binding to MUC1, which comprises
  (i) a heavy chain, which has the amino acid sequence represented by amino acid Nos 20 to 460 of SEQ ID NO: 20 or 23, and
  (ii) a light chain, which has amino acid sequence represented by amino acid Nos 21 to 239 of SEQ ID NO: 21.

Embodiment 22. The antibody according to any one of Embodiments 1 to 21, wherein the antibody comprises at least one heavy chain, comprising the heavy chain variable region, a CH1 domain, a hinge region, a CH2 domain and a CH3 domain.

Embodiment 23. The antibody according to any one of Embodiments 1 to 21, wherein the antibody comprises two heavy chains, each comprising the heavy chain variable region, a CH1 domain, a hinge region, a CH2 domain and a CH3 domain.

Embodiment 24. The antibody according to Embodiment 22 or 23, wherein the antibody is an IgG-type antibody, in particular an IgG1, IgG2 or IgG4-type antibody.

Embodiment 25. The antibody according to any one of Embodiments 1 to 24, wherein the antibody comprises at least one light chain, comprising the light chain variable region and a CL domain.

Embodiment 26. The antibody according to any one of Embodiments 1 to 24, wherein the antibody comprises two light chains, each comprising the light chain variable region and a CL domain.

Embodiment 274. The antibody according to Embodiment 25 or 26, wherein the light chain is a κ-type light chain.

Embodiment 28. The antibody according to any one of Embodiments 1 to 27, wherein the antibody does not comprise an N-glycosylation site in the CH2 domain.

Embodiment 29. The antibody according to any one of Embodiments 1 to 27, wherein the antibody comprises an N-glycosylation site in the CH2 domain of the antibody heavy chains.

Embodiment 30. The antibody according to Embodiment 29, wherein the antibody has a glycosylation pattern having one or more of the following characteristics
  (i) a relative amount of glycans carrying a bisecting GlcNAc residue of at least 0.5% of the total amount of glycans attached to the glycosylation sites of the antibody in a composition;
  (ii) a relative amount of glycans carrying at least one galactose residue of at least 30% of the total amount of glycans attached to the glycosylation sites of the antibody in a composition;
  (iii) a relative amount of glycans carrying a core fucose residue of at least 60% of the total amount of glycans attached to the glycosylation sites the antibody in a composition.

Embodiment 31. The antibody according to Embodiment 29, wherein the antibody has a glycosylation pattern having one or more of the following characteristics
  (i) a relative amount of glycans carrying a bisecting GlcNAc residue of at least 0.5% of the total amount of glycans attached to the glycosylation sites of the antibody in a composition;
  (ii) a relative amount of glycans carrying at least one galactose residue of at least 30% of the total amount of glycans attached to the glycosylation sites of the antibody in a composition;
  (iii) a relative amount of glycans carrying a core fucose residue of 40% or less of the total amount of glycans attached to the glycosylation sites of the antibody in a composition.

Embodiment 32. The antibody according to any one of Embodiments 1 to 31, comprising a further agent conjugated thereto.

Embodiment 33. The antibody according to Embodiment 32, wherein the further agent is a chemotherapeutic agent which is coupled to the antibody.

Embodiment 34. The antibody according to Embodiment 33, wherein the chemotherapeutic agent is selected from the group consisting of a maytansinoid, a DNA damaging agent, a DNA alkylating agent and a DNA minor groove binder.

Embodiment 35. The antibody according to Embodiment 33, wherein the chemotherapeutic agent is selected from the group consisting of maytansinol, $N^{2'}$-deacetyl-$N^{2'}$-(3-mercapto-1-oxopropyl)-maytansine (DM1), $N^{2'}$-deacetyl-$N^{2'}$-(4-mercapto-1-oxopentyl)-maytansine (DM3), and $N^{2'}$-deacetyl-$N^{2'}$-(4-methyl-4-mercapto-1-oxopentyl)-maytansine (DM4).

Embodiment 36. The antibody according to Embodiment 33, wherein the chemotherapeutic agent is selected from the group consisting of monomethyl auristatin F (MMAF), monomethyl auristatin E (MMAE) and auristatin T.

Embodiment 37. The antibody according to Embodiment 33, wherein the chemotherapeutic agent is selected from the group consisting of pyrrolobenzodiazepine (PBD), pyrrolobenzodiazepine dimer (PBD dimer), duocarmycin, duocarmycin-hydroxybenzamide-azaindole (DUBA), seco-duocarmycin-hydroxybenzamide-azaindole (seco-DUBA) and doxorubicin.

Embodiment 38. The antibody according to Embodiment 33, wherein the chemotherapeutic agent is selected from the group consisting of indolinobenzodiazepine and oxazolidinobenzodiazepine.

Embodiment 39. The antibody according to Embodiment 33, wherein the chemotherapeutic agent is calicheamicin.

Embodiment 40. The antibody according to Embodiment 32, wherein the further agent is a polypeptide or protein which is fused to a polypeptide chain of the antibody.

Embodiment 41. The antibody according to Embodiment 40, wherein the antibody comprises two antibody heavy chains and two antibody light chains and a further agent being a polypeptide or protein is fused to each of the C termini of said antibody heavy chains or to each of the C termini of said antibody light chains.

Embodiment 42. The antibody according to Embodiment 40 or 41, wherein the further agent is selected from the group consisting of cytokines, chemokines, other antibodies, antigen binding fragments, enzymes and binding domains.

Embodiment 43. The antibody according to Embodiment 41, wherein the further agent is a scFv fragment specifically binding to CD3, and one of said further agent is fused to the C terminus of each antibody heavy chain.

Embodiment 44. The antibody according to Embodiment 41, wherein the further agent is a scFv fragment specifically binding to PDL1, and one of said further agent is fused to the C terminus of each antibody light chain.

Embodiment 45. A nucleic acid encoding the antibody according to any one of Embodiments 1 to 44.

Embodiment 46. An expression cassette or vector comprising the nucleic acid according to Embodiment 75 and a promoter operatively connected with said nucleic acid.

Embodiment 47. A host cell comprising the nucleic acid according to Embodiment 45 or the expression cassette or vector according to Embodiment 46.

Embodiment 48. A pharmaceutical composition comprising the antibody or conjugate according to any one of Embodiments 1 to 44 and one or more further components selected from the group consisting of solvents, diluents, and excipients.

Embodiment 49. The antibody according to any one of Embodiments 1 to 44 or the pharmaceutical composition according to Embodiment 48 for use in medicine.

Embodiment 50. The antibody according to any one of Embodiments 1 to 44 or the pharmaceutical composition according to Embodiment 48 for use in the treatment, prognosis, diagnosis, detecting and/or monitoring of diseases associated with abnormal cell growth such as cancer; infections such as bacterial, viral, fungal or parasitic infections; inflammatory diseases such as autoimmune diseases and inflammatory bowel diseases; and diseases associated with a reduce immune activity such as immunodeficiencies.

Embodiment 51. The antibody or pharmaceutical composition according to Embodiment 50 for use in the treatment of cancer, in particular the cancer expressing TA-MUC1, wherein the cancer is selected from the group consisting of cancer of the ovarian cancer, breast cancer, pancreatic cancer, lung cancer, colon cancer, stomach cancer, liver cancer, kidney cancer, blood cancer, endometrial cancer, thyroid cancer, leukemia, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

Embodiment 52. The antibody or pharmaceutical composition according to Embodiment 50 for use in the treatment of infections, wherein the infection is selected from the group consisting of bacterial infections, viral infections, fungal infections and parasitic infections.

Embodiment 53. The antibody or pharmaceutical composition according to Embodiment 50 for use in the treatment of autoimmune diseases, wherein the autoimmune disease is selected from the group consisting of celiac disease, diabetes mellitus type 1, Graves disease, inflammatory bowel disease, multiple sclerosis, psoriasis, rheumatoid arthritis and systemic lupus erythematosus.

Embodiment 54. A method of increasing the MUC1 binding affinity of an antibody comprising
  (i) a heavy chain variable region, which
    (a) has an amino acid sequence which is at least 90% identical to the amino acid sequence of SEQ ID NO: 11, and
    (b) comprises the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
  (ii) a light chain variable region, which
    (a) has an amino acid sequence which is at least 90% identical to the amino acid sequence of SEQ ID NO: 12, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
the method comprising the step of substituting the amino acid residue at position 8 of CDR-H2 with any amino acid residue except asparagine, resulting in CDR-H2 having the amino acid sequence of SEQ ID NO: 2.

Embodiment 55. A method of increasing the MUC1 binding affinity of an antibody comprising
  (i) a heavy chain variable region, which
    (a) has an amino acid sequence which is at least 95% identical to the amino acid sequence of SEQ ID NO: 11, and
    (b) comprises the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
  (ii) a light chain variable region, which
    (a) has an amino acid sequence which is at least 95% identical to the amino acid sequence of SEQ ID NO: 12, and
    (b) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
the method comprising the step of substituting the amino acid residue at position 8 of CDR-H2 with any amino acid residue except asparagine, resulting in CDR-H2 having the amino acid sequence of SEQ ID NO: 2.

Embodiment 56. The method according to embodiment 54 or 55, wherein substituting the amino acid residue at position 8 of CDR-H2 is achieved by introducing a mutation into the nucleic acid coding for the antibody, wherein the mutation is introduced in the codon coding for said amino acid residue.

Embodiment 57. The method according to any one of Embodiments 54 to 56, comprising the steps of
(a) providing a nucleic acid coding for the antibody which MUC1 binding affinity is to be increased;
(b) introducing a mutation into said nucleic acid to produce a mutated nucleic acid, wherein the mutation is introduced in the codon coding for the amino acid residue at position 8 of CDR-H2 so that said codon codes for any amino acid residue except asparagine; and
(c) expressing the mutated nucleic acid to produce an antibody with increased MUC1 binding affinity.

Embodiment 58. A method of producing an antibody with increased MUC1 binding affinity, comprising
(a) providing a nucleic acid coding for an antibody which comprises
  (i) a heavy chain variable region, which
    (i1) has an amino acid sequence which is at least 90% identical to the amino acid sequence of SEQ ID NO: 11, and
    (i2) comprises the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
  (ii) a light chain variable region, which
    (ii1) has an amino acid sequence which is at least 90% identical to the amino acid sequence of SEQ ID NO: 12, and
    (ii2) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
(b) introducing a mutation into said nucleic acid to produce a mutated nucleic acid, wherein the mutation is introduced in the codon coding for the amino acid residue at position 8 of CDR-H2 so that said codon codes for any amino acid residue except asparagine; and
(c) producing the antibody with increased MUC1 binding affinity by expressing the mutated nucleic acid in a host cell.

Embodiment 59. A method of producing an antibody with increased MUC1 binding affinity, comprising
(a) providing a nucleic acid coding for an antibody which comprises
  (i) a heavy chain variable region, which
    (i1) has an amino acid sequence which is at least 95% identical to the amino acid sequence of SEQ ID NO: 11, and
    (i2) comprises the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
  (ii) a light chain variable region, which
    (ii1) has an amino acid sequence which is at least 95% identical to the amino acid sequence of SEQ ID NO: 12, and
    (ii2) comprises the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
(b) introducing a mutation into said nucleic acid to produce a mutated nucleic acid, wherein the mutation is introduced in the codon coding for the amino acid residue at position 8 of CDR-H2 so that said codon codes for any amino acid residue except asparagine; and
(c) producing the antibody with increased MUC1 binding affinity by expressing the mutated nucleic acid in a host cell.

Embodiment 60. The method according to any one of Embodiments 54 to 59, wherein the antibody comprises two heavy chains, each comprising the heavy chain variable region, a CH1 domain, a hinge region, a CH2 domain and a CH3 domain.

Embodiment 61. The method according to Embodiment 60, wherein the antibody is an IgG-type antibody, in particular an IgG1, IgG2 or IgG4-type antibody.

Embodiment 62. The method according to any one of Embodiments 54 to 60, wherein the antibody comprises two light chains, each comprising the light chain variable region and a CL domain.

Embodiment 63. The method according to Embodiment 62, wherein the light chain is a κ-type light chain.

Embodiment 64. The method according to any one of Embodiments 54 to 63, wherein the antibody with increased MUC1 binding affinity is an antibody as defined in any one of Embodiments 1 to 44.

Embodiment 65. A method for treating cancer in a subject in need thereof comprising, administering to the subject with cancer, in particular cancer expressing TA-MUC1, a therapeutically effective amount of the antibody according to any one of Embodiments 1 to 44 or the composition according to Embodiment 48.

Embodiment 66. The method for treating cancer according to Embodiment 65, wherein the cancer is selected from the group consisting of ovarian cancer, breast cancer, pancreatic cancer, lung cancer, colon cancer, stomach cancer, liver cancer, kidney cancer, blood cancer, endometrial cancer, thyroid cancer, leukemia, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

FIGURES

FIG. 1 shows ELISA binding curves of the anti-MUC1 antibodies to different MUC1 peptides. (A) shows antigen binding of PankoMab N54Q (PM-N54Q) lacking Fab glycosylation and PankoMab comprising Fab glycosylation (PM) to the MUC1 peptide comprising the epitope sequence PDTR. The threonine of the MUC1 peptide is glycosylated with Tn, sTn, TF or sTF. (B) shows binding of PankoMab and PankoMab N54Q to the MUC1 peptide comprising the epitope sequence variant PESR. The serine of the MUC1 peptide is glycosylated with Tn. (C) shows binding of PankoMab N54Q to the MUC1 peptide comprising the epitope sequence PDTR. The threonine of the MUC1 peptide is glycosylated with Tn or not glycosylated. (D) shows binding of several N54X variants to Tn-PDTR MUC1 peptide compared to PankoMab comprising Fab glycosylation diluted from cell culture supernatant of transiently transfected cells. (E) shows binding curves of three purified N54X variants without Fab glycosylation in comparison to PankoMab with Fab glycosylation on Tn-PDTR, TF-PDTR and non-glycosylated PDTR MUC1 peptide. (F) shows binding of two framework variants of PM-N54Q to Tn-PDTR MUC1 peptide compared to PankoMab with Fab glycosylation. For framework variant mf-a nine amino acids are mutated in the VH and three in the VL framework, for mf-b also nine amino acids are mutated in the VH and four in the VL framework.

FIG. 2 shows surface plasmon resonance (Biacore) binding of the anti-MUC1 antibodies PM and PM-N54Q to a Tn-glycosylated PDTR-MUC1 peptide. The maximal binding signal of different concentrations of PankoMab N54Q and PankoMab are plotted against the antibody concentration.

Figure 4:
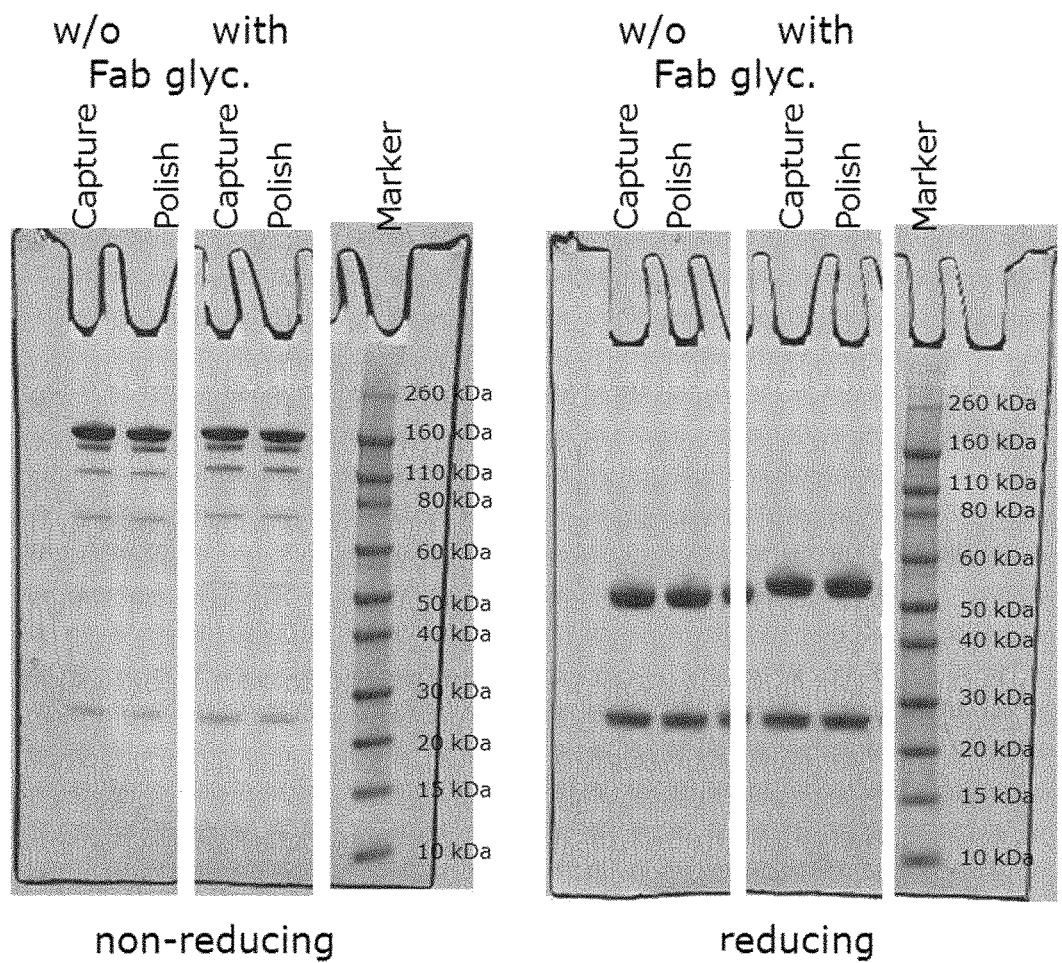

FIG. 4 shows an SDS acrylamide gel of an electrophoretic separation of PankoMab N54Q and PankoMab under non-reducing (left) and reducing (right) conditions. Lane 1: PankoMab N54Q after capture step; lane 2: PankoMab N54Q after polishing step; lane 3: PankoMab after capture step; lane 4: PankoMab after polishing step; lane 5: molecular weight marker.

Figure 5:
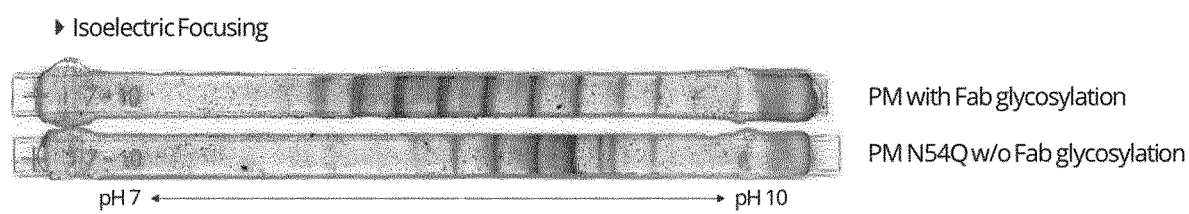

FIG. 5 shows the Coomassie blue stained gel of an isoelectric focusing assay with PankoMab N54Q lacking Fab glycosylation and PankoMab being Fab-glycosylated. Lane 1: PankoMab with Fab glycosylation; lane 2: PankoMab N54Q without Fab glycosylation.

Figure 6:
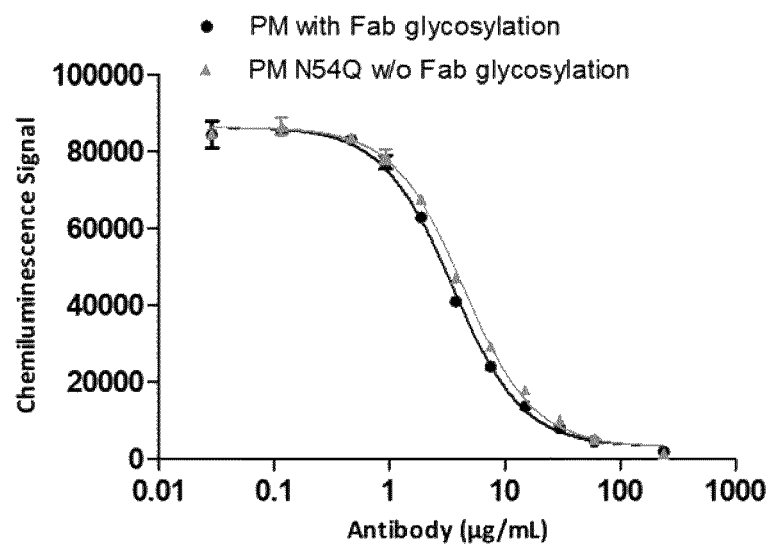
Figure 6:
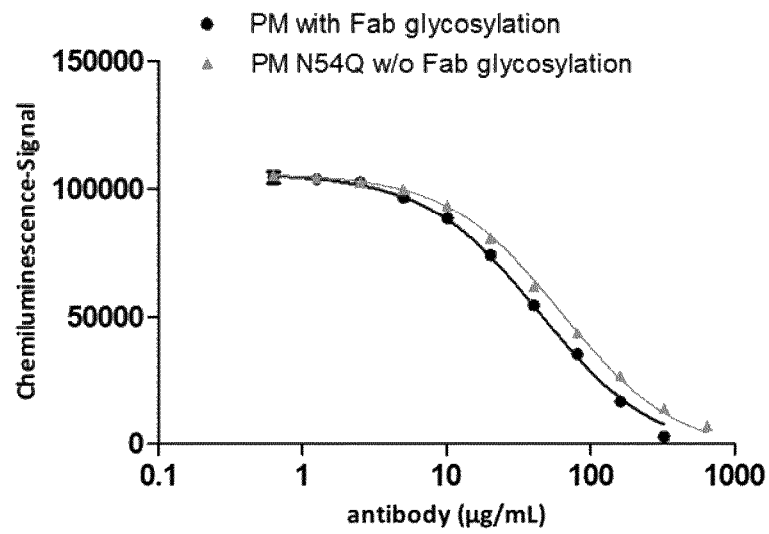

FIG. 6 shows anti-MUC1 antibody binding to Fcγ receptor IIIa. Increasing concentrations of the antibody PankoMab N54Q or PankoMab displace rabbit-anti-mouse coupled acceptor beads from FcγRIIIa loaded donor beads, thereby reducing the detected chemiluminescence. In FIG. 6A low-fucosylated antibodies and in FIG. 6B high-fucosylated antibodies were applied into the assay.

Figure 7:
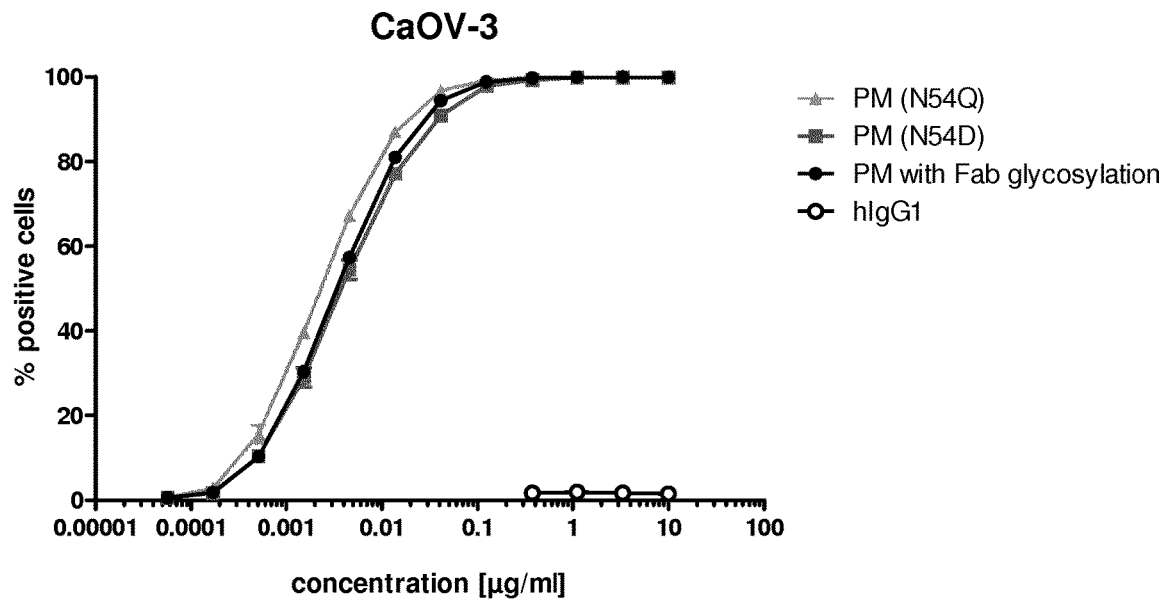
Figure 7:
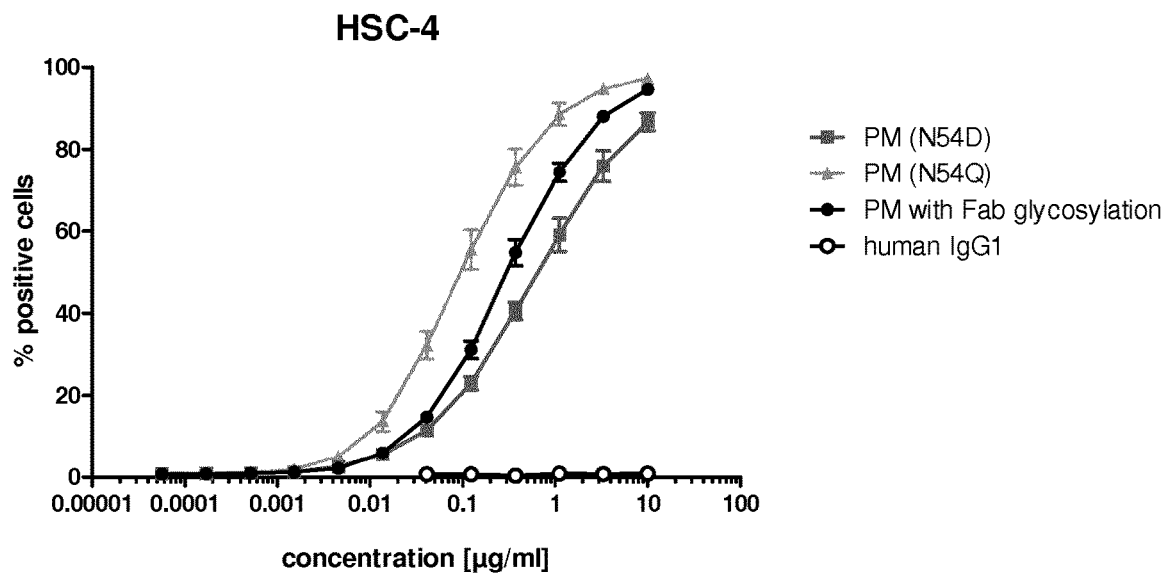

FIG. 7 shows binding of the anti-MUC1 antibodies PM-N54Q, PM-N54D and PM with Fab glycosylation to the tumor cell lines (A) CaOV-3 and (B) HSC-4 as analyzed by flow cytometry.

FIG. 8 shows the amino acid sequence of the heavy chain of the humanized antibody PankoMab N54Q (SEQ ID No: 15, wherein the amino acid at position 57 is Gln, namely SEQ ID No: 22).

FIG. 9 shows the amino acid sequence of the light chain of the humanized antibody PankoMab N54Q (SEQ ID No: 16).

FIG. 10 shows the amino acid sequence of the heavy chain of the humanized antibody PankoMab (SEQ ID No: 19).

FIG. 11 shows the amino acid sequence of the heavy chain of chimeric antibody PankoMab N54Q (SEQ ID No: 20, wherein the amino acid at position 76 is Gln, namely SEQ ID No: 23).

FIG. 12 shows the amino acid sequence of the light chain of chimeric antibody PankoMab N54Q (SEQ ID No: 21).

EXAMPLES

Example 1: Production of Anti-MUC1 Antibodies

The nucleic acid sequence of the heavy chain of humanized PankoMab antibody (see, e.g., WO 2011/012309) was modified by mutating the codon for Asn54 according to the Kabat/EU numbering system (amino acid position 57 in SEQ ID NO: 11) into the codon for any amino acid except Asn, especially for Gln.

1) Production of the Anti-MUC1 Antibodies in a Human Myeloid Leukemia Derived Cell Line Vectors comprising the coding sequences of the γ1-type heavy chain and the κ-type light chain of the mutated antibodies were transfected into the human myeloid leukemia derived cell line NM-H9D8 (DSM ACC2806). The different αMUC1-antibodies comprising the N54X mutation (PankoMab N54X/PM-N54X whereby X is any amino acid except N/Asn) or amino acid mutations in the framework sequences of the VH and VL were expressed in the obtained clones, producing the constructs with a human glycosylation pattern. The concentration of the αMUC1-antibodies in the supernatant was determined by Octet measurement using Protein A coated pins or were quantified by UV280 absorbance after purification by protein A chromatography. The binding characteristics of the different αMUC1-antibodies were determined by Antigen-ELISA (see example 2), and selected purified antibodies were also analyzed by Scatchard analysis (see example 3), by Biacore (see example 4a), by $DRX^2$ switchSENSE® technology (see example 4b), or by flow cytometry (example 7).

In addition, PM-N54Q and non-mutated PankoMab with Fab-glycosylation were also expressed in the human myeloid leukemia derived cell line NM-H9D8-E6Q12 (DSM ACC2856) expressing antibody with reduced fucose. Together with the same antibodies expressed in NM-H9D8, these antibodies were purified and analyzed in example 6 for their binding behavior to Fc gamma receptor Ill A.

2) Production of the Anti-MUC1 Antibody in CHO Cell Line

PM-N54Q encoding sequences (nucleotide sequence of heavy chain of PM-N54Q represented by SEQ ID NO: 17 and nucleotide sequence of light chain of PM-N54Q represented by SEQ ID NO: 18) which was synthesized by GeneArt™ of ThermoFisher scientific were cloned into expression vectors and resulting plasmids were electro-transfected into CHO cells. Pooled cells grown under selection pressure were applied to manufacture PM-N54Q mutant antibody with general procedures.

Example 2: Antigen ELISA

The antigen binding characteristics of PankoMab N54X, wherein the N-glycosylation site in the Fab part is knocked out, was compared to PankoMab having an N-glycosylation site in its Fab part.

Binding characteristics of the Fab-deglycosylated version of the MUC1-specific antibody PankoMab (PM-N54Q) compared to the (glycosylated) PankoMab-GEX® were analyzed using differently glycosylated and the non-glycosylated MUC1-derived tandem repeat peptides in ELISA studies. In principle, both antibodies show the same gradation by means of binding to glycosylated PDTR peptides (APPAHGVTSAPD-T(X)-RPAPGSTAPPAHGVTSA) with different glycosylations at T: Strongest binding was observed to the PDTR peptide carrying a Galß1-3GalNAc$_{alpha}$ (TF) followed by sialylated TF GalNAc$_{alpha}$ (Tn)

Figure 1:
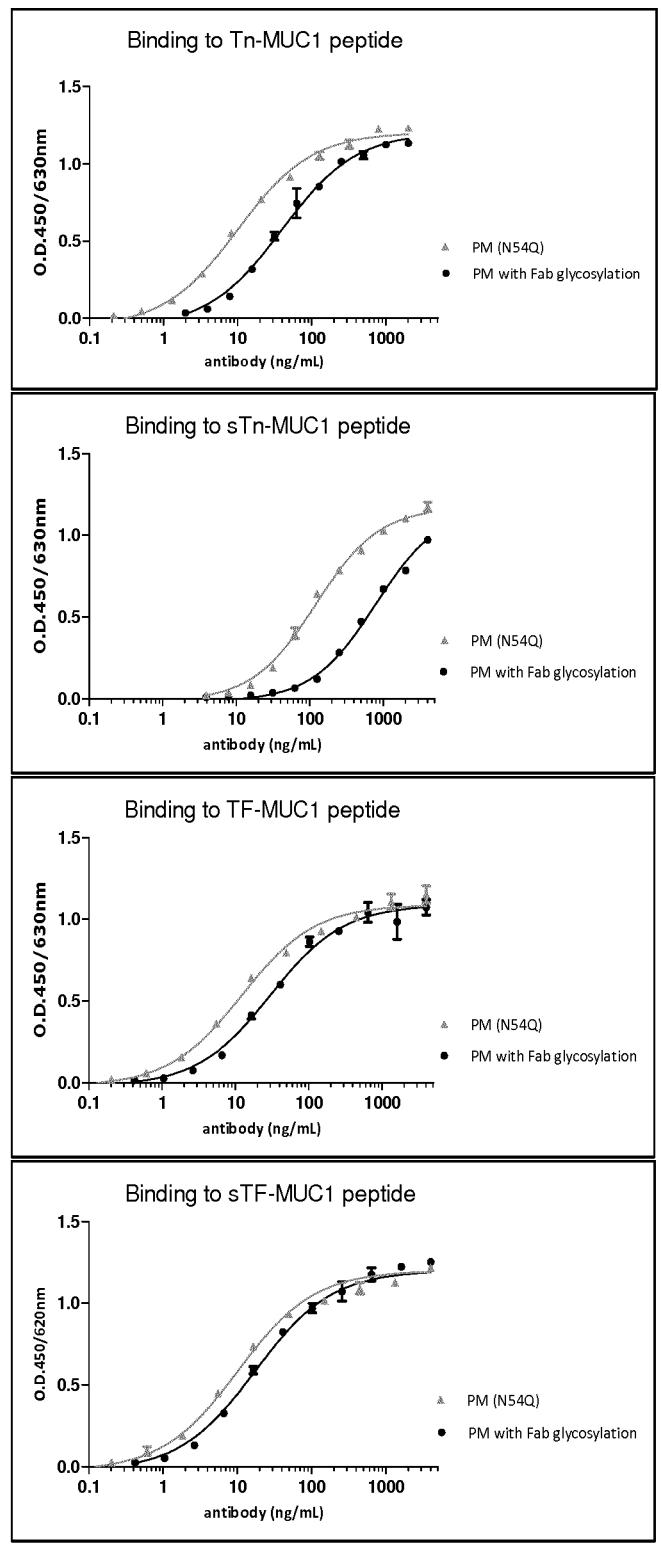

O-glycosylation. Binding to sialylated GalNAc$_{alpha}$(sTn)O-glycosylation was significantly lower. As PankoMab-GEX®, PM-N54Q showed only little binding activity to non-glycosylated MUC1 PDTR peptide indicating adequate tumor specificity (FIG. 1C).

However, in comparison to PankoMab-GEX® four-fold higher binding was found for PM-N54Q in the TA-MUC1 antigen ELISA using the biotinylated glycopeptide carrying a GalNAc$_{alpha}$ (Tn)O-glycan. PM-N54Q binds about seven-fold better to the same MUC1 peptide when glycosylated with sialylated GalNAc$_{alpha}$ (sTn). The binding to Galß1-3GalNAc$_{alpha}$ (TF) and sialylated TF (sTF) at the threonine of the PDTR-sequence (FIG. 1A) was two-fold better for PM-N54Q.

Both antibodies show strongly diminished binding to the MUC1 peptide variant APPAHGVTSAPE-S(Tn)-RPAPG-STAPPAHGVTSA with Tn glycosylation at the serine compared to that at PDT(Tn)R-peptide. However, also here the Fab-deglycosylated PM-N54Q binds significantly stronger than PankoMab-GEX® (FIG. 1B).

Different other Fab-deglycosylated PM-N54X variants were compared to PankoMab having an N-glycosylation in its Fab part. First, all variants were compared directly from the supernatant, without purification. The concentration was determined by Octet. All PM-N54X variants bound better than Fab-glycosylated PM. In addition, a clear trend depending on the chemical properties of the amino acid side chain was visible. Carboxylic acid groups at the side chain showed the lowest binding enhancement. Best binding was observed for amino acids with one or two nitrogens (as primary or secondary amines) (FIG. 1D).

In addition, selected Fab-deglycosylated variants (PM-N54H, -W and -Q) were purified by Protein A chromatography and analyzed on ELISA (FIG. 1E). The improvement of binding to TF-MUC1 peptide is about 5- to 8-fold and to Tn-MUC1 peptide about 2- to 3-fold compared to PankoMab with Fab-glycosylation, respectively.

Furthermore, two different framework variants of the PM-N54Q were analyzed for the binding to the Tn-glycosylated PDTR-MUC1 peptide in ELISA (see FIG. 1F). The framework variant mf-a carries nine amino acid mutations in the VH and three in the VL framework; the variant mf-b carries also nine amino acid mutations in the VH and four in the VL framework. Both mutated variants show similar binding compared to the PM-N54Q antibody.

Example 3: Saturation Binding Analyses of Anti-MUC1 Antibodies to MCF-7 and ZR-75-1 Cells Two factors are especially critical for the therapeutic suitability of an antibody: the affinity and number of binding sites of an antibody on tumor cells.

Binding of the Fab-deglycosylated version of the MUC1-specific antibody PankoMab (PM-N54Q) on TA-MUC-1 positive human tumor cell lines was evaluated using radiolabeled antibodies by saturated binding analysis on the human mamma carcinoma cell lines ZR-75-1 and MCF-7 in comparison to Fab-glycosylated PankoMab-GEX®. The antibodies were chelated with a 12-fold molar excess of p-SCN-Benzyl-DTPA in 50 mM sodium carbonate, 150 mM NaCl, pH 8.7, for 2 h at 37° C., followed by over-night incubation at 2-8° C. Free chelator was removed over desalting columns and dead-end filtration (50 kDa cut-off, 6× buffer exchange to PBS). The chelated antibodies were radiolabeled with carrier-free $^{111}$In (2 μCi/μg antibody) for 1 h at 37° C. in 6 mM phosphate, 1.6 mM KCl, 80 mM NaCl, 0.2 M Na-acetate, 0.1 M HCl. The preparations were neutralized by addition of 8-9fold volume of 10× concentrated PBS. About 1/50 volume of fetal bovine serum were added to the neutralized labelled antibody preparation. Per cell binding approach 1*10$^6$ cells were used. Several concentrations of labelled antibodies were added to the pelleted cells (30-1000 ng/200 μL in 1% BSA/PBS). The resuspended cell-antibody mixtures were measured in a gamma-counter and incubated 1 h at 4° C. Cells with bound antibodies were separated by centrifugation and washed with 1% BSA/PBS for another hour at 4° C. The cell pellet was then measured for bound $^{111}$In-labelled antibody in a gamma counter. Evaluation was performed by "one-site specific ka" in GraphPad Prism. The obtained data are summarized in Table 1. The data show the high affinity and very high number of binding sites of PM-N54Q on these tumor cells. The binding was more than 2.5-fold higher than for PankoMab-GEX® and also the number of binding sites was slightly increased.

TABLE 1

| Association constant and antigen binding sites on MUC1$^+$ tumor cells | | |
|---|---|---|
| | ZR-75-1 | MCF-7 |
| K$_{ass}$ [1/M] | | |
| PM w Fab glyc. | 1.2 × 10$^7$ | 3 × 10$^7$ |
| PM N54Q w/o Fab glyc. | 3.4 × 10$^7$ | 7.8 × 10$^7$ |
| Binding sites | | |
| PM w Fab glyc. | 20 × 10$^5$ | 0.6 × 10$^5$ |
| PM N54Q w/o Fab glyc. | 30 × 10$^5$ | 0.9 × 10$^5$ |

Example 4a: Surface Plasmon Resonance (BiaCore) Analysis

Binding of the Fab-deglycosylated version of the MUC1-specific antibody PankoMab (PM-N54Q) on TA-MUC-1 derived glycosylated peptide was evaluated by surface plasmon resonance analysis (Biacore). A streptavidin sensor chip was coated with biotinylated TA-MUC1 peptide (Tn glycosylated or not glycosylated). PankoMab and PM-N54Q were diluted sequentially 1:3 from 3,600 to 4.9 nM in HPS-EP. The dilutions were injected at 50 μL/min. Maximal binding of each concentration was determined as response units (RU), respectively, and evaluated with GraphPad Prism using "one-site specific binding". FIG. 2 shows the obtained binding curves with PM-N54Q compared to PankoMab-GEX®. Affinities (K) of 388 nM and 652 nM were calculated for PM-N54Q and PankoMab-GEX®, respectively. Therefore, in this experimental setting a nearly two-fold increase in affinity was detectable.

Example 4b: Fluorescence Proximity Sensing (by DRX$^2$, Dynamic Biosensors)

A new method to determine binding constants and affinity is the fluorescence proximity sensing using single stranded DNA (96 mer) spotted on a chip and complementary DNA coupled to a ligand. In the present study streptavidin was used as a ligand to capture biotinylated TA-MUC1 peptides. Binding of PankoMab to the peptides resulted in a fluorescence change. On- and off-rates can be calculated during association and dissociation. Due to a higher sensitivity faster interactions can be monitored compared to surface plasmon resonance. This results in binding kinetics different from SPR but more comparable to the "gold standard" method KinExA, measured in a liquid system.

Figure 3A:
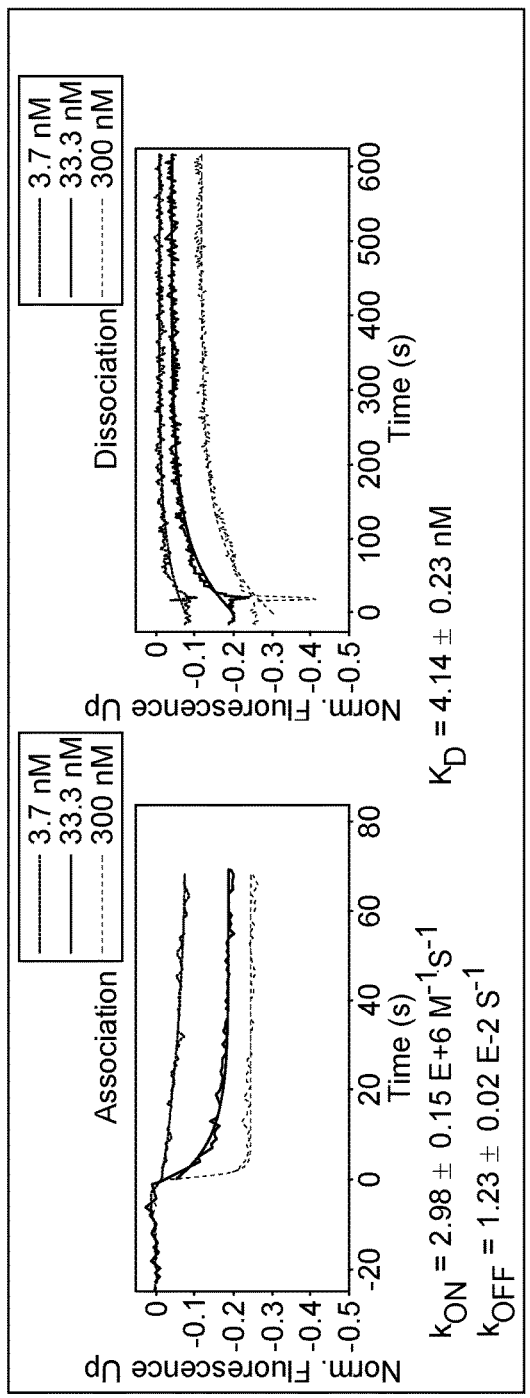
FIG. 3 shows results of Fluorescence Proximity Sensing on DRX instrument. Association and dissociation curves are shown. (A) PM with Fab glycosylation compared to (B) PM-N54Q without Fab glycosylation.
Figure 3B:
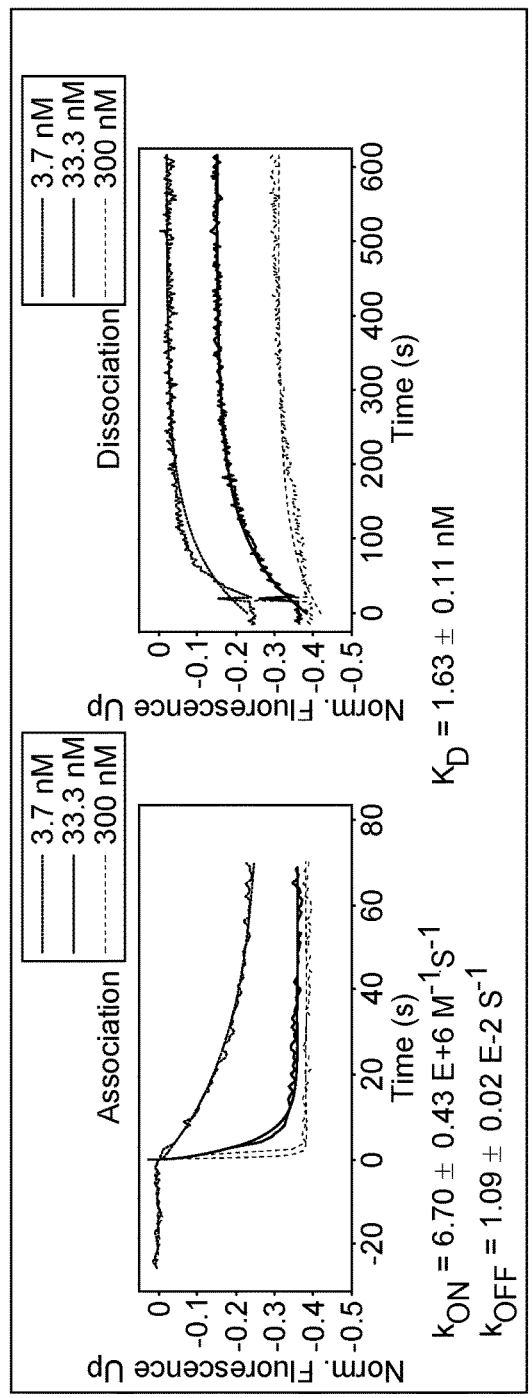

PankoMab and PM-N54Q were diluted from 300 nM in 1:9 steps to 3.67 nM in PE140 buffer and applied to the chip-bound peptides. Binding curves were evaluated by mono-exponential global fit (instrument software). Binding curves of PM and PM-N54Q are exemplarily shown in FIGS. 3A and B. Calculated affinities of PankoMab variants are shown in Table 2:

TABLE 2

Dissociation constants of PankoMab variants to antigen peptide

| PankoMab variant | $K_D$ |
|---|---|
| PM with Fab glycosylation | 4.1 nM |
| PM-N54D | 1.9 nM |
| PM-N54Q | 1.6 nM |
| PM-N54H | 0.6 nM |

Example 5: Biochemical Characterization

Non-reducing and reducing SDS-PAGE is used to analyze purity and identity of an antibody. The band pattern in non-reducing gels shows the major band at about 160 kDa and methodical artefacts of heavy and light chains and combinations thereof (25, 50-55, 75, 110, 135 kDa). Reducing gels show distinct light and heavy chain bands at 25 and 50-55 kDa. Due to lack of the Fab glycosylation PM-N54Q has a smaller heavy chain, as expected (see FIG. 4, right).

The charge profile is clearly different, as shown by isoelectric focusing (IEF; see FIG. 5). The Fab glycosylation is considerably sialylated, whereas the Fc glycosylation is only minimally sialylated. Thus PankoMab-GEX® has more charged isoforms than PM-N54Q, reflecting its higher level of negatively charged sialic acids in the Fab part.

Example 6: Fcγ Receptor Binding

FcγR binding assays for FcγRIIIa (CD16a) are based on the AlphaScreen® technology of PerkinElmer. The AlphaScreen® platform relies on simple bead-based technology of PerkinElmer and is a more efficient alternative to traditional ELISA since no washing steps are necessary.

For the receptor binding assays, His-tagged FcγRIIIa (Glycotope GmbH) is captured by Ni-chelate donor beads. Anti-MUC1 antibodies and rabbit-anti-mouse coupled acceptor beads compete for binding to FcγR. In case of interaction of FcγR with rabbit-anti-mouse-bound acceptor beads, donor and acceptor beads come into close proximity which leads, upon laser excitation at 680 nm, to light emission. A maximum signal is achieved (signal$_{max}$) without a competitor. In case of competition, where a test antibody binds to FcγR, the signal$_{max}$ is reduced in a concentration-dependent manner. Chemiluminescence was quantified by measurement at 520-620 nm (AlphaScreen® method) using an EnSpire 2300 multilabel reader (PerkinElmer). All results were expressed as the mean±standard deviation of duplicate samples. The data were evaluated and calculated using non-linear curve fitting (sigmoidal dose-response variable slope) with GraphPad Prism 5 software. As a result, a concentration dependent sigmoidal curve was obtained, which is defined by top-plateau, bottom-plateau, slope and $EC_{50}$.

As shown in FIGS. 6A and B, the FcγRIIIa binding affinity was comparable for PankoMab N54Q and PankoMab whereby in Figure A low-fucosylated antibodies and in Figure B high-fucosylated antibodies were applied into the assay. Hence, removal of the Fab glycosylation did not affect receptor interaction of the antibody.

Example 7: Binding to Cellular TA-MUC1

N54Q and N54D were transiently expressed and purified by protein A chromatography. Binding of the two variants to cell surface TA-MUC1 was compared to PM with Fab glycosylation using two different carcinoma cell lines. The tongue squamous cell carcinoma line HSC-4 expresses TA-MUC1 to a medium degree and the ovarian carcinoma cell line CaOV-3 to a high degree. Tumor cells were incubated with antibodies in serial dilutions and bound antibodies were detected using a Phycoerythrin-conjugated goat anti-human IgG (heavy and light chain) antibody. A human IgG control was included to control for background staining. Binding was analyzed by flow cytometry.

The analyzed constructs PM, PM-N54Q and PM-N54D show strong and specific binding to the TA-MUC1 expressing HSC-4 and CaOV-3 cells compared to a human IgG1 control (FIG. 7). The binding of PM-N54D to the TA-MUC1$^{high}$ CaOV-3 cells was comparable to PM with Fab glycosylation while PM-N54Q showed a slightly better binding (FIG. 7A). Using HSC-4 carcinoma cells that express TA-MUC1 at an intermediate level, the variant PM-N54Q was clearly superior in binding to cellular TA-MUC1 compared to PM while PM-N54D showed an inferior binding compared to PM with Fab glycosylation (FIG. 7B).

Identification of the Deposited Biological Material

The cell lines DSM ACC 2806, DSM ACC 2807 and DSM ACC 2856 were deposited at the DSMZ—Deutsche Sammlung von Mikroorganismen und Zellkulturen GmbH, Inhoffenstraße 7B, 38124 Braunschweig (DE) by Glycotope GmbH, Robert-Rössle-Str. 10, 13125 Berlin (DE) on the dates indicated in the following table.

| Name of the Cell Line | Accession Number | Depositor | Date of Deposition |
|---|---|---|---|
| NM-H9D8 | DSM ACC 2806 | Glycotope GmbH | Sep. 15, 2006 |
| NM-H9D8-E6 | DSM ACC 2807 | Glycotope GmbH | Oct. 5, 2006 |
| NM-H9D8-E6Q12 | DSM ACC 2856 | Glycotope GmbH | Aug. 8, 2007 |

The invention claimed is:

1. An antibody capable of binding to MUC1, which comprises
   (i) a heavy chain variable region comprising the complementarity-determining regions (CDRs) CDR-H1 having the amino acid sequence of SEQ ID NO: 1, CDR-H2 having the amino acid sequence of SEQ ID NO: 7 and CDR-H3 having the amino acid sequence of SEQ ID NO: 3, and
   (ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6; wherein the antibody is not part of a conjugate comprising a topoisomerase inhibitor.

2. The antibody according to claim 1, wherein the heavy chain variable region has the amino acid sequence of SEQ ID NO: 10 or an amino acid sequence which is at least 90% identical to the amino acid sequence of SEQ ID NO: 10.

3. The antibody according to claim 1, wherein the light chain variable region has the amino acid sequence of SEQ ID NO: 12 or an amino acid sequence which is at least 90% identical to the amino acid sequence of SEQ ID NO: 12.

4. The antibody according to claim 1, wherein the heavy chain variable region of the antibody has the amino acid sequence of SEQ ID NO: 10 and the light chain variable region of the antibody has the amino acid sequence of SEQ ID NO: 12.

5. The antibody according to claim 1, wherein the antibody comprises an Fc region and preferably is an IgG1, IgG2 or IgG4-type antibody.

6. The antibody according to claim 5, wherein the antibody comprises a glycosylation pattern having one or more of the following characteristics:
   (i) a detectable amount of glycans carrying a bisecting GlcNAc residue;
   (ii) a relative amount of glycans carrying at least one galactose residue of at least 25% of the total amount of glycans attached to the Fc glycosylation sites of the antibody in a composition.

7. The antibody according to claim 1, wherein the antibody comprises a heavy chain having the amino acid sequence of SEQ ID NO: 22, and a light chain having the amino acid sequence of SEQ ID NO: 16.

8. The antibody according to claim 1, wherein the antibody is obtainable by production in a mammalian cell.

9. The antibody according to claim 1, obtainable by production in a human cell line selected from the group consisting of NM-H9D8 (DSM ACC 2806), NM-H9D8-E6 (DSM ACC 2807), NM-H9D8-E6Q12 (DSM ACC 2856) and cell lines derived therefrom.

10. The antibody according to claim 1, wherein the antibody is obtainable by production in a CHO cell line or a cell line derived therefrom.

11. The antibody according to claim 1, wherein the antibody competes for the binding to TA-MUC1 with an antibody comprising a heavy chain variable region having the amino acid sequence of SEQ ID NO: 10 and a light chain variable region having the amino acid sequence of SEQ ID NO: 12.

12. A nucleic acid encoding the antibody according to claim 1.

13. An expression cassette or vector comprising the nucleic acid according to claim 12 and a promoter operatively connected with said nucleic acid.

14. A host cell comprising the nucleic acid according to claim 12.

15. A conjugate comprising the antibody according to claim 1 conjugated to a further agent, wherein the further agent is a polypeptide or protein.

16. The conjugate according to claim 15, wherein the further agent is a cytokine, an immunomodulatory compound, a tumor-specific antibody or an immune checkpoint blocking or activating antibody.

17. A method for the treatment of cancer, an infection, an autoimmune disease or an immunodeficiency disorder, comprising the step of administering the conjugate according to claim 15.

18. The method of treatment according to claim 17, wherein the cancer is characterized by expressing TA-MUC1.

19. The method of treatment according to claim 17, wherein the cancer is selected from the group consisting of ovarian cancer, breast cancer, pancreatic cancer, lung cancer, colon cancer, stomach cancer, liver cancer, kidney cancer, blood cancer, endometrial cancer, thyroid cancer, leukemias, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

20. The method of treatment according to claim 17, wherein the conjugate is used in combination with a further agent.

21. A method for the diagnosis, detecting and/or monitoring of cancer, an infection, an autoimmune disease or an immunodeficiency disorder, comprising the step of contacting a test sample with the conjugate according to claim 15.

22. The method according to claim 21, wherein the cancer is characterized by expressing TA-MUC1.

23. The method according to claim 21, wherein the cancer is selected from the group consisting of ovarian cancer, breast cancer, pancreatic cancer, lung cancer, colon cancer, stomach cancer, liver cancer, kidney cancer, blood cancer, endometrial cancer, thyroid cancer, leukemias, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

24. The method according to claim 21, wherein the conjugate is used in combination with a further agent.

25. A composition comprising the antibody according to claim 1.

26. A method for the treatment of cancer, an infection, an autoimmune disease or an immunodeficiency disorder, comprising the step of administering the antibody according to claim 1.

27. The method of treatment according to claim 26, wherein the cancer is characterized by expressing TA-MUC1.

28. The method of treatment according to claim 26, wherein the cancer is selected from the group consisting of ovarian cancer, breast cancer, pancreatic cancer, lung cancer, colon cancer, stomach cancer, liver cancer, kidney cancer, blood cancer, endometrial cancer, thyroid cancer, leukemias, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

29. The method of treatment according to claim 26, wherein the antibody is used in combination with a further agent.

30. A method for the diagnosis, detecting and/or monitoring of cancer, an infection, an autoimmune disease or an immunodeficiency disorder, comprising the step of contacting a test sample with the antibody according to claim 1.

31. The method according to claim 30, wherein the cancer is characterized by expressing TA-MUC1.

32. The method according to claim 30, wherein the cancer is selected from the group consisting of ovarian cancer, breast cancer, pancreatic cancer, lung cancer, colon cancer, stomach cancer, liver cancer, kidney cancer, blood cancer, endometrial cancer, thyroid cancer, leukemias, seminomas, melanomas, carcinomas, teratomas, lymphomas, sarcomas, mesotheliomas, neuroblastomas, gliomas, rectal cancer, adrenal cancer, skin cancer, cancer of the brain, cervical cancer, intestinal cancer, intestine cancer, head and neck cancer, gastrointestinal cancer, lymph node cancer, esophagus cancer, colorectal cancer, ear, nose and throat (ENT) cancer, prostate cancer, bladder cancer, cancer of the uterus and the metastases thereof.

33. The method according to claim 30, wherein the antibody is used in combination with a further agent.

34. A method of increasing the MUC1 binding affinity of an antibody comprising
(i) a heavy chain variable region comprising the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
(ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6,
the method comprising the step of substituting the amino acid residue at position 8 of CDR-H2 with glutamine, resulting in CDR-H2 having the amino acid sequence of SEQ ID NO: 7.

35. The method according to claim 34, wherein substituting the amino acid residue at position 8 of CDR-H2 is achieved by introducing a mutation into the nucleic acid coding for the antibody, wherein the mutation is introduced in the codon coding for said amino acid residue.

36. A method of producing an antibody with increased MUC1 binding affinity, comprising
(a) providing a nucleic acid coding for an antibody which comprises
(i) a heavy chain variable region comprising the complementarity-determining regions (CDRs) CDR-H1 having the amino acid sequence of SEQ ID NO: 1, CDR-H2 having the amino acid sequence of SEQ ID NO: 8 and CDR-H3 having the amino acid sequence of SEQ ID NO: 3, and
(ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6;
(b) introducing a mutation into said nucleic acid to produce a mutated nucleic acid, wherein the mutation is introduced in the codon coding for the amino acid residue at position 8 of CDR-H2 so that said codon codes for glutamine; and
(c) producing the antibody with increased MUC1 binding affinity by expressing the mutated nucleic acid in a host cell.

37. The method according to claim 36, wherein the antibody with increased MUC1 binding affinity comprises
(i) a heavy chain variable region comprising the complementarity-determining regions (CDRs) CDR-H1 having the amino acid sequence of SEQ ID NO: 1, CDR-H2 having the amino acid sequence of SEQ ID NO: 7 and CDR-H3 having the amino acid sequence of SEQ ID NO: 3, and
(ii) a light chain variable region comprising the complementarity-determining regions (CDRs) CDR-L1 having the amino acid sequence of SEQ ID NO: 4, CDR-L2 having the amino acid sequence of SEQ ID NO: 5 and CDR-L3 having the amino acid sequence of SEQ ID NO: 6.

* * * * *

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
```

<223> OTHER INFORMATION: CDR-H1

<400> SEQUENCE: 1

Asn Tyr Trp Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: CDR-H2
<220> FEATURE:
<221> NAME/KEY: VARIANT
<222> LOCATION: (8)..(8)
<223> OTHER INFORMATION: Xaa is any amino acid except Asn

<400> SEQUENCE: 2

Glu Ile Arg Leu Lys Ser Asn Xaa Tyr Thr Thr His Tyr Ala Glu Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: CDR-H3

<400> SEQUENCE: 3

His Tyr Tyr Phe Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: CDR-L1

<400> SEQUENCE: 4

Arg Ser Ser Lys Ser Leu Leu His Ser Asn Gly Ile Thr Tyr Phe Phe
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

Gln Met Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDR-L3

<400> SEQUENCE: 6

Ala Gln Asn Leu Glu Leu Pro Pro Thr
1               5

-continued

```
<210> SEQ ID NO 7
<211> LENGTH: 19
<212> TYPE: PRT
<213> ORGANISM: Artificial Sequence
<220> FEATURE:
<223> OTHER INFORMATION: CDR-H2

<400> SEQUENCE: 7

Glu Ile Arg Leu Lys Ser Asn Gln Tyr Thr Thr His Tyr Ala Glu Ser
1               5                   10                  15

Val Lys Gly

<210> SEQ ID NO 8
<211> LENGTH: 19
<212> TYPE: PRT
<213> ORGANISM: Artificial Sequence
<220> FEATURE:
<223> OTHER INFORMATION: CDR-H2

<400> SEQUENCE: 8

Glu Ile Arg Leu Lys Ser Asn Asn Tyr Thr Thr His Tyr Ala Glu Ser
1               5                   10                  15

Val Lys Gly

<210> SEQ ID NO 9
<211> LENGTH: 117
<212> TYPE: PRT
<213> ORGANISM: Artificial Sequence
<220> FEATURE:
<223> OTHER INFORMATION: heavy chain variable region
<220> FEATURE:
<221> NAME/KEY: VARIANT
<222> LOCATION: (57)..(57)
<223> OTHER INFORMATION: Xaa is any amino acid except Asn

<400> SEQUENCE: 9

Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Xaa Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: heavy chain variable region

<400> SEQUENCE: 10

Glu Val Gln Leu Val Glu Ser Gly Gly Gly Leu Val Gln Pro Gly Gly
1               5                   10                  15
```

Ser Met Arg Leu Ser Cys Val Ala Ser Gly Phe Pro Phe Ser Asn Tyr
            20                  25                  30

Trp Met Asn Trp Val Arg Gln Ala Pro Gly Lys Gly Leu Glu Trp Val
            35                  40                  45

Gly Glu Ile Arg Leu Lys Ser Asn Gln Tyr Thr Thr His Tyr Ala Glu
 50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
            115

<210> SEQ ID NO 11
<211> LENGTH: 117
<212> TYPE: PRT
<213> ORGANISM: Artificial Sequence
<220> FEATURE:
<223> OTHER INFORMATION: heavy chain variable region

<400> SEQUENCE: 11

Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser Asn Tyr
            20                  25                  30

Trp Met Asn Trp Val Arg Gln Ala Pro Gly Lys Gly Leu Glu Trp Val
            35                  40                  45

Gly Glu Ile Arg Leu Lys Ser Asn Asn Tyr Thr Thr His Tyr Ala Glu
 50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
            115

<210> SEQ ID NO 12
<211> LENGTH: 113
<212> TYPE: PRT
<213> ORGANISM: Artificial Sequence
<220> FEATURE:
<223> OTHER INFORMATION: light chain variable region

<400> SEQUENCE: 12

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Gln Ser
            35                  40                  45

Pro Gln Leu Leu Ile Tyr Gln Met Ser Asn Leu Ala Ser Gly Val Pro
 50                  55                  60

Asp Arg Phe Ser Gly Ser Gly Ser Gly Thr Asp Phe Thr Leu Arg Ile

```
                 65                  70                  75                  80
Ser Arg Val Glu Ala Glu Asp Val Gly Val Tyr Tyr Cys Ala Gln Asn
                 85                  90                  95

Leu Glu Leu Pro Pro Thr Phe Gly Gln Gly Thr Lys Val Glu Ile Lys
                100                 105                 110

Arg

<210> SEQ ID NO 13
<211> LENGTH: 4
<212> TYPE: PRT
<213> ORGANISM: Artificial Sequence
<220> FEATURE:
<223> OTHER INFORMATION: epitope

<400> SEQUENCE: 13

Pro Asp Thr Arg
1

<210> SEQ ID NO 14
<211> LENGTH: 4
<212> TYPE: PRT
<213> ORGANISM: Artificial Sequence
<220> FEATURE:
<223> OTHER INFORMATION: epitope

<400> SEQUENCE: 14

Pro Glu Ser Arg
1

<210> SEQ ID NO 15
<211> LENGTH: 447
<212> TYPE: PRT
<213> ORGANISM: Artificial Sequence
<220> FEATURE:
<223> OTHER INFORMATION: heavy chain
<220> FEATURE:
<221> NAME/KEY: VARIANT
<222> LOCATION: (57)..(57)
<223> OTHER INFORMATION: Xaa is any amino acid except Asn

<400> SEQUENCE: 15

Glu Val Gln Leu Val Glu Ser Gly Gly Gly Leu Val Gln Pro Gly Gly
1               5                  10                  15

Ser Met Arg Leu Ser Cys Val Ala Ser Gly Phe Pro Phe Ser Asn Tyr
                20                  25                  30

Trp Met Asn Trp Val Arg Gln Ala Pro Gly Lys Gly Leu Glu Trp Val
            35                  40                  45

Gly Glu Ile Arg Leu Lys Ser Asn Xaa Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Gly Leu
            420                 425                 430

His Asn His Tyr Thr Gln Lys Ser Leu Ser Leu Ser Pro Gly Lys
        435                 440                 445

<210> SEQ ID NO 16
<211> LENGTH: 219
<212> TYPE: PRT
<213> ORGANISM: Artificial Sequence
<220> FEATURE:
<223> OTHER INFORMATION: light chain

<400> SEQUENCE: 16

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

```
Ser Arg Val Glu Ala Glu Asp Val Gly Val Tyr Tyr Cys Ala Gln Asn
            85                  90                  95

Leu Glu Leu Pro Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 17
<211> LENGTH: 1401
<212> TYPE: DNA
<213> ORGANISM: Artificial Sequence
<220> FEATURE:
<223> OTHER INFORMATION: heavy chain

<400> SEQUENCE: 17
atgaagcacc tgtggttctt tctgctgctg gtggccgctc ctagatgggt gctgtctgaa      60
gtgcagctgg tggaatctgg cggaggattg gttcagcctg gcggctccat gagactgtct     120
tgtgtggcct ctggcttccc cttctccaac tactggatga actgggtccg acaggcccct     180
ggcaaaggac tggaatgggt cggagagatc cggctgaagt ccaaccagta caccacacac     240
tacgccgagt ccgtgaaggg cagattcacc atctctcggg acgactccaa gaactccctg     300
tacctgcaga tgaacagcct gaaaaccgag gacaccgccg tgtactactg cacccggcac     360
tactacttcg actactgggg ccagggcacc ctggtcacag tttcttccgc ttccaccaag     420
ggacccagcg tgttccctct ggctccttcc agcaagtcta cctctggcgg aacagctgct     480
ctgggctgcc tggtcaagga ctactttcct gagcctgtga ccgtgtcctg aactctggc     540 gctctgacat ctggcgtgca cccttccca gctgtgctgc agtcctccgg cctgtactct     600
ctgtcctctg tcgtgaccgt gccttccagc tctctgggaa cccagaccta catctgcaat     660
gtgaaccaca gccttccaa caccaaggtg gacaagaagg tggaacccaa gtcctgcgac     720
aagacccaca cctgtcctcc atgtcctgct ccagaactgc tcggcggacc ttccgtgttc     780
ctgtttcctc caaagcctaa ggacaccctg atgatcagca aaccctga agtgacctgc     840 gtggtggtgg atgtgtctca cgaggacccc gaagtgaagt tcaattggta cgtggacggc     900
gtggaagtgc acaacgccaa gaccaagcct agagaggaac agtacaactc cacctacaga     960
gtggtgtccg tgctgaccgt gctgcaccag gattggctga acggcaaaga gtacaagtgc    1020
aaggtgtcca acaaggccct gcctgctcct atcgaaaaga ccatctccaa ggccaagggc    1080
cagcctaggg aaccccaggt ttacaccttg cctccaagca gggacgagct gaccaagaac    1140
caggtgtccc tgacctgcct cgtgaaggga ttctacccct ccgatatcgc cgtggaatgg    1200
gagtctaatg ccagcctga gaacaactac aagacaaccc ctcctgtgct ggactccgac    1260
```

```
ggctcattct tcctgtactc caagctgaca gtggacaagt ccagatggca gcagggcaac    1320
gtgttctcct gctccgtgat gcatgagggc ctgcacaacc actacaccca gaagtccctg    1380
tctctgagcc ccggcaaatg a                                              1401
```

<210> SEQ ID NO 18
<211> LENGTH: 720
<212> TYPE: DNA
<213> ORGANISM: Artificial Sequence
<220> FEATURE:
<223> OTHER INFORMATION: light chain

<400> SEQUENCE: 18

```
atggttctgc agacacaggt gttcatctcc ctgctgctgt ggatctctgg cgcctacggc     60
gacatcgtga tgacccagtc tccactgagc aaccccgtga cacctggcga gcctgcctcc    120
atctcttgcc ggtcctctaa gtctctgctg cactccaacg gcatcaccta cttttctgg    180 tatctgcaga agcccggcca gtctcctcag ctgctgatct accagatgtc caacctggcc    240
tctggcgtgc ccgatagatt tccggctct ggctctggca ccgacttcac cctgagaatc    300
tccagagtgg aagccgagga cgtgggcgtg tactactgtg cccagaacct ggaactgcct    360
cctacctttg ccagggcac aaggtggaa atcaagcgga cagtggccgc tccttccgtg    420
tttatcttcc caccttccga cgagcagctg aagtccggca gcttctgt cgtgtgcctg    480 ctgaacaact ctacccctcg ggaagccaag gtgcagtgga aggtggacaa tgccctgcag    540
tccggcaact cccaagagtc tgtgaccgag caggactcca aggacagcac ctacagcctg    600
tcctccacac tgaccctgtc caaggccgac tacgagaagc acaaggtgta cgcctgcgaa    660
gtgacccatc agggcctgtc tagccctgtg accaagtctt caaccggggg cgagtgctga    720
```

<210> SEQ ID NO 19
<211> LENGTH: 447
<212> TYPE: PRT
<213> ORGANISM: Artificial Sequence
<220> FEATURE:
<223> OTHER INFORMATION: heavy chain

<400> SEQUENCE: 19

```
Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
```

| | | | 145 | | | | 150 | | | | 155 | | | | 160 |

Gly Ala Leu Thr Ser Gly Val His Thr Phe Pro Ala Val Leu Gln Ser
                165                              170                      175

Ser Gly Leu Tyr Ser Leu Ser Ser Val Val Thr Val Pro Ser Ser Ser
                180                              185                      190

Leu Gly Thr Gln Thr Tyr Ile Cys Asn Val Asn His Lys Pro Ser Asn
                195                              200                      205

Thr Lys Val Asp Lys Lys Val Glu Pro Lys Ser Cys Asp Lys Thr His
210                                215                              220

Thr Cys Pro Pro Cys Pro Ala Pro Glu Leu Leu Gly Gly Pro Ser Val
225                              230                            235                      240

Phe Leu Phe Pro Pro Lys Pro Lys Asp Thr Leu Met Ile Ser Arg Thr
                245                              250                      255

Pro Glu Val Thr Cys Val Val Val Asp Val Ser His Glu Asp Pro Glu
                260                              265                      270

Val Lys Phe Asn Trp Tyr Val Asp Gly Val Glu Val His Asn Ala Lys
                275                              280                      285

Thr Lys Pro Arg Glu Glu Gln Tyr Asn Ser Thr Tyr Arg Val Val Ser
290                                295                              300

Val Leu Thr Val Leu His Gln Asp Trp Leu Asn Gly Lys Glu Tyr Lys
305                                310                            315                      320

Cys Lys Val Ser Asn Lys Ala Leu Pro Ala Pro Ile Glu Lys Thr Ile
                325                              330                      335

Ser Lys Ala Lys Gly Gln Pro Arg Glu Pro Gln Val Tyr Thr Leu Pro
                340                              345                      350

Pro Ser Arg Asp Glu Leu Thr Lys Asn Gln Val Ser Leu Thr Cys Leu
                355                              360                      365

Val Lys Gly Phe Tyr Pro Ser Asp Ile Ala Val Glu Trp Glu Ser Asn
                370                              375                      380

Gly Gln Pro Glu Asn Asn Tyr Lys Thr Thr Pro Pro Val Leu Asp Ser
385                                390                            395                      400

Asp Gly Ser Phe Phe Leu Tyr Ser Lys Leu Thr Val Asp Lys Ser Arg
                405                              410                      415

Trp Gln Gln Gly Asn Val Phe Ser Cys Ser Val Met His Glu Gly Leu
                420                              425                      430

His Asn His Tyr Thr Gln Lys Ser Leu Ser Leu Ser Pro Gly Lys
                435                              440                      445

```
<210> SEQ ID NO 20
<211> LENGTH: 460
<212> TYPE: PRT
<213> ORGANISM: Artificial Sequence
<220> FEATURE:
<223> OTHER INFORMATION: heavy chain
<220> FEATURE:
<221> NAME/KEY: VARIANT
<222> LOCATION: (76)..(76)
<223> OTHER INFORMATION: Xaa is any amino acid except Asn

<400> SEQUENCE: 20
```

Met Lys His Leu Trp Phe Phe Leu Leu Leu Val Ala Ala Pro Arg Trp
1                    5                              10                      15

Val Leu Ser Glu Val Gln Leu Val Glu Ser Gly Gly Gly Leu Val Gln
                20                              25                      30

Pro Gly Gly Ser Met Arg Leu Ser Cys Val Ala Ser Gly Phe Pro Phe
                35                              40                      45

```
Ser Asn Tyr Trp Met Asn Trp Val Arg Gln Ala Pro Gly Lys Gly Leu
 50                  55                  60
Glu Trp Val Gly Glu Ile Arg Leu Lys Ser Asn Xaa Tyr Thr Thr His
 65                  70                  75                  80
Tyr Ala Glu Ser Val Lys Gly Arg Phe Thr Ile Ser Arg Asp Asp Ser
                 85                  90                  95
Lys Asn Ser Leu Tyr Leu Gln Met Asn Ser Leu Lys Thr Glu Asp Thr
                100                 105                 110
Ala Val Tyr Tyr Cys Thr Arg His Tyr Tyr Phe Asp Tyr Trp Gly Gln
            115                 120                 125
Gly Thr Leu Val Thr Val Ser Ser Ala Lys Thr Thr Pro Pro Ser Val
130                 135                 140
Tyr Pro Leu Ala Pro Gly Ser Ala Ala Gln Thr Asn Ser Met Val Thr
145                 150                 155                 160
Leu Gly Cys Leu Val Lys Gly Tyr Phe Pro Glu Pro Val Thr Val Thr
                165                 170                 175
Trp Asn Ser Gly Ser Leu Ser Ser Gly Val His Thr Phe Pro Ala Val
            180                 185                 190
Leu Gln Ser Asp Leu Tyr Thr Leu Ser Ser Ser Val Thr Val Pro Ser
        195                 200                 205
Ser Thr Trp Pro Ser Gln Thr Val Thr Cys Asn Val Ala His Pro Ala
210                 215                 220
Ser Ser Thr Lys Val Asp Lys Lys Ile Val Pro Arg Asp Cys Gly Cys
225                 230                 235                 240
Lys Pro Cys Ile Cys Thr Val Pro Glu Val Ser Ser Val Phe Ile Phe
                245                 250                 255
Pro Pro Lys Pro Lys Asp Val Leu Thr Ile Thr Leu Thr Pro Lys Val
            260                 265                 270
Thr Cys Val Val Val Asp Ile Ser Lys Asp Asp Pro Glu Val Gln Phe
        275                 280                 285
Ser Trp Phe Val Asp Asp Val Glu Val His Thr Ala Gln Thr Lys Pro
290                 295                 300
Arg Glu Glu Gln Ile Asn Ser Thr Phe Arg Ser Val Ser Glu Leu Pro
305                 310                 315                 320
Ile Met His Gln Asp Trp Leu Asn Gly Lys Glu Phe Lys Cys Arg Val
                325                 330                 335
Asn Ser Ala Ala Phe Pro Ala Pro Ile Glu Lys Thr Ile Ser Lys Thr
            340                 345                 350
Lys Gly Arg Pro Lys Ala Pro Gln Val Tyr Thr Ile Pro Pro Pro Lys
        355                 360                 365
Glu Gln Met Ala Lys Asp Lys Val Ser Leu Thr Cys Met Ile Thr Asn
370                 375                 380
Phe Phe Pro Glu Asp Ile Thr Val Glu Trp Gln Trp Asn Gly Gln Pro
385                 390                 395                 400
Ala Glu Asn Tyr Lys Asn Thr Gln Pro Ile Met Asp Thr Asp Gly Ser
                405                 410                 415
Tyr Phe Val Tyr Ser Lys Leu Asn Val Gln Lys Ser Asn Trp Glu Ala
            420                 425                 430
Gly Asn Thr Phe Thr Cys Ser Val Leu His Glu Gly Leu His Asn His
        435                 440                 445
His Thr Glu Lys Ser Leu Ser His Ser Pro Gly Lys
450                 455                 460
```

```
<210> SEQ ID NO 21
<211> LENGTH: 239
<212> TYPE: PRT
<213> ORGANISM: Artificial Sequence
<220> FEATURE:
<223> OTHER INFORMATION: light chain

<400> SEQUENCE: 21

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Leu Ser Asn Pro
                20                  25                  30

Val Thr Pro Gly Glu Pro Ala Ser Ile Ser Cys Arg Ser Ser Lys Ser
            35                  40                  45

Leu Leu His Ser Asn Gly Ile Thr Tyr Phe Phe Trp Tyr Leu Gln Lys
        50                  55                  60

Pro Gly Gln Ser Pro Gln Leu Leu Ile Tyr Gln Met Ser Asn Leu Ala
65                  70                  75                  80

Ser Gly Val Pro Asp Arg Phe Ser Gly Ser Gly Ser Thr Asp Phe
                85                  90                  95

Thr Leu Arg Ile Ser Arg Val Glu Ala Glu Asp Val Gly Val Tyr Tyr
                100                 105                 110

Cys Ala Gln Asn Leu Glu Leu Pro Pro Thr Phe Gly Gln Gly Thr Lys
            115                 120                 125

Val Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
210                 215                 220

Thr Ser Thr Ser Pro Ile Val Lys Ser Phe Asn Arg Asn Glu Cys
225                 230                 235

<210> SEQ ID NO 22
<211> LENGTH: 447
<212> TYPE: PRT
<213> ORGANISM: Artificial Sequence
<220> FEATURE:
<223> OTHER INFORMATION: heavy chain

<400> SEQUENCE: 22

Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser Asn Tyr
                20                  25                  30

Trp Met Asn Trp Val Arg Gln Ala Pro Gly Lys Gly Leu Glu Trp Val
            35                  40                  45

Gly Glu Ile Arg Leu Lys Ser Asn Gln Tyr Thr Thr His Tyr Ala Glu
        50                  55                  60

Ser Val Lys Gly Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Thr Arg His Tyr Phe Asp Tyr Trp Gly Gln Gly Thr Leu
        100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Gly Leu
            420                 425                 430

His Asn His Tyr Thr Gln Lys Ser Leu Ser Leu Ser Pro Gly Lys
        435                 440                 445

<210> SEQ ID NO 23
<211> LENGTH: 460
<212> TYPE: PRT
<213> ORGANISM: Artificial Sequence
<220> FEATURE:
<223> OTHER INFORMATION: heavy chain

<400> SEQUENCE: 23
```

-continued

```
Met Lys His Leu Trp Phe Phe Leu Leu Val Ala Ala Pro Arg Trp
  1               5                  10                  15

Val Leu Ser Glu Val Gln Leu Val Glu Ser Gly Gly Gly Leu Val Gln
             20                  25                  30

Pro Gly Gly Ser Met Arg Leu Ser Cys Val Ala Ser Gly Phe Pro Phe
                 35                  40                  45

Ser Asn Tyr Trp Met Asn Trp Val Arg Gln Ala Pro Gly Lys Gly Leu
 50                  55                  60

Glu Trp Val Gly Glu Ile Arg Leu Lys Ser Asn Gln Tyr Thr Thr His
 65                  70                  75                  80

Tyr Ala Glu Ser Val Lys Gly Arg Phe Thr Ile Ser Arg Asp Asp Ser
                 85                  90                  95

Lys Asn Ser Leu Tyr Leu Gln Met Asn Ser Leu Lys Thr Glu Asp Thr
                100                 105                 110

Ala Val Tyr Tyr Cys Thr Arg His Tyr Tyr Phe Asp Tyr Trp Gly Gln
                115                 120                 125

Gly Thr Leu Val Thr Val Ser Ser Ala Lys Thr Thr Pro Pro Ser Val
                130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
                180                 185                 190

Leu Gln Ser Asp Leu Tyr Thr Leu Ser Ser Ser Val Thr Val Pro Ser
                195                 200                 205

Ser Thr Trp Pro Ser Gln Thr Val Thr Cys Asn Val Ala His Pro Ala
210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
                260                 265                 270

Thr Cys Val Val Val Asp Ile Ser Lys Asp Asp Pro Glu Val Gln Phe
                275                 280                 285

Ser Trp Phe Val Asp Asp Val Glu Val His Thr Ala Gln Thr Lys Pro
                290                 295                 300

Arg Glu Glu Gln Ile Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
                340                 345                 350

Lys Gly Arg Pro Lys Ala Pro Gln Val Tyr Thr Ile Pro Pro Pro Lys
                355                 360                 365

Glu Gln Met Ala Lys Asp Lys Val Ser Leu Thr Cys Met Ile Thr Asn
                370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
```

```
                420                 425                 430
Gly Asn Thr Phe Thr Cys Ser Val Leu His Glu Gly Leu His Asn His
            435                 440                 445

His Thr Glu Lys Ser Leu Ser His Ser Pro Gly Lys
450                 455                 460
```